(12) United States Patent
Li et al.

(10) Patent No.: US 11,479,608 B2
(45) Date of Patent: Oct. 25, 2022

(54) ANTI-CTLA4 ANTIBODIES

(71) Applicant: Akeso Biopharma, Inc., Guangdong (CN)

(72) Inventors: Baiyong Li, Guangdong (CN); Yu Xia, Guangdong (CN); Peng Zhang, Guangdong (CN); Xinghua Pang, Guangdong (CN); Zhongmin Wang, Guangdong (CN)

(73) Assignee: Akeso Biopharma, Inc., Guangdong (CN)

( * ) Notice: Subject to any disclaimer, the term of this patent is extended or adjusted under 35 U.S.C. 154(b) by 382 days.

(21) Appl. No.: 16/327,615

(22) PCT Filed: Aug. 21, 2017

(86) PCT No.: PCT/US2017/047721
§ 371 (c)(1),
(2) Date: Feb. 22, 2019

(87) PCT Pub. No.: WO2018/039097
PCT Pub. Date: Mar. 1, 2018

(65) Prior Publication Data
US 2019/0177414 A1  Jun. 13, 2019

(30) Foreign Application Priority Data

Aug. 23, 2016 (WO) ............... PCT/CN2016/096357

(51) Int. Cl.
| | | |
|---|---|---|
| *A61K 39/395* | (2006.01) | |
| *C07K 16/28* | (2006.01) | |
| *C12N 5/12* | (2006.01) | |
| *C12N 15/63* | (2006.01) | |
| *C12N 15/85* | (2006.01) | |
| *G01N 33/52* | (2006.01) | |
| *G01N 33/53* | (2006.01) | |
| *G01N 33/68* | (2006.01) | |
| *A61K 39/00* | (2006.01) | |
| *A61P 35/00* | (2006.01) | |
| *G01N 33/541* | (2006.01) | |
| *A61K 38/00* | (2006.01) | |

(52) U.S. Cl.
CPC .. *C07K 16/2818* (2013.01); *A61K 39/001129* (2018.08); *A61K 39/395* (2013.01); *A61K 39/3955* (2013.01); *A61P 35/00* (2018.01); *C12N 5/12* (2013.01); *C12N 15/63* (2013.01); *C12N 15/85* (2013.01); *G01N 33/52* (2013.01); *G01N 33/53* (2013.01); *G01N 33/541* (2013.01); *G01N 33/6863* (2013.01); *A61K 38/00* (2013.01); *A61K 39/001111* (2018.08); *A61K 2039/505* (2013.01); *C07K 2317/24* (2013.01); *C07K 2317/56* (2013.01); *C07K 2317/565* (2013.01); *C07K 2317/76* (2013.01); *C07K 2317/92* (2013.01); *C07K 2319/30* (2013.01); *C07K 2319/40* (2013.01); *C12N 2015/8518* (2013.01)

(58) Field of Classification Search
CPC ............ A61K 2039/505; A61K 39/395; A61K 39/3955; C07K 16/2818; C07K 2317/76; C07K 2317/92; C07K 2317/24; C07K 2317/565; C07K 2317/56; C07K 2319/00; G01N 33/53; G01N 33/6863
See application file for complete search history.

(56) References Cited

U.S. PATENT DOCUMENTS

| | | | |
|---|---|---|---|
| 4,816,567 A | 3/1989 | Cabilly et al. | |
| 5,811,097 A | 9/1998 | Allison et al. | |
| 5,855,887 A | 1/1999 | Allison et al. | |
| 5,977,318 A | 11/1999 | Linsley et al. | |
| 6,051,227 A | 4/2000 | Allison et al. | |
| 6,682,736 B1 | 1/2004 | Hanson et al. | |
| 6,984,720 B1 | 1/2006 | Korman et al. | |
| 7,109,003 B2 | 9/2006 | Hanson et al. | |
| 7,132,281 B2 | 11/2006 | Hanson et al. | |
| 7,411,057 B2 | 8/2008 | Hanson et al. | |
| 7,452,535 B2 | 11/2008 | Davis et al. | |
| 7,465,446 B2 | 12/2008 | Lowy et al. | |
| 7,595,048 B2 | 9/2009 | Honjo et al. | |
| 7,605,236 B2 * | 10/2009 | Ruben ..................... | A61P 31/18 530/387.9 |
| 7,605,238 B2 | 10/2009 | Korman et al. | |
| 7,744,875 B2 | 6/2010 | Lowy et al. | |
| 7,807,797 B2 | 10/2010 | Hanson et al. | |
| 7,824,679 B2 | 11/2010 | Hanson et al. | |
| 8,008,449 B2 | 8/2011 | Korman et al. | |

(Continued)

FOREIGN PATENT DOCUMENTS

| | | |
|---|---|---|
| CN | 1328571 A | 12/2001 |
| CN | 101074264 A | 11/2007 |
| CN | 1753912 B | 11/2011 |
| CN | 103221544 A | 7/2013 |

(Continued)

OTHER PUBLICATIONS

Tiller, K. and Tessier, P. Advances in antibody design. Annual Reviews in Biomedical Engineering, 17, pp. 191-216, Aug. 14, 2015 (Year: 2015).*

(Continued)

*Primary Examiner* — Bridget E Bunner
(74) *Attorney, Agent, or Firm* — Mercedes K. Meyer

(57) ABSTRACT

The present invention belongs to the fields of tumor therapy and molecular immunology. The present invention relates to an anti-CTLA4 antibody, pharmaceutical composition and use thereof. The anti-CTLA4 antibody of the present invention can specifically bind CTLA4, and can very effectively block the binding of CLTA4 to B7.

24 Claims, 12 Drawing Sheets
Specification includes a Sequence Listing.

(56) References Cited

U.S. PATENT DOCUMENTS

| | | |
|---|---|---|
| 8,017,714 B2 | 9/2011 | Uhrich |
| 8,129,508 B2 | 3/2012 | Arunakumari et al. |
| 8,142,778 B2 | 3/2012 | Davis et al. |
| 8,143,379 B2 | 3/2012 | Hanson et al. |
| 8,168,170 B2 | 5/2012 | Myatt |
| 8,263,073 B2 | 9/2012 | Korman et al. |
| 8,318,916 B2 | 11/2012 | Korman et al. |
| 8,435,516 B2 | 5/2013 | Huang et al. |
| 8,491,895 B2 | 7/2013 | Hanson et al. |
| 8,697,847 B2 | 4/2014 | Arunakumari et al. |
| 8,728,474 B2 | 5/2014 | Honjo et al. |
| 8,765,415 B2 | 7/2014 | Arunakumari et al. |
| 8,779,105 B2 | 7/2014 | Korman et al. |
| 8,784,815 B2 | 7/2014 | Korman et al. |
| 8,883,984 B2 | 11/2014 | Hanson et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,119,839 B2 | 9/2015 | Huang et al. |
| 9,212,224 B2 | 12/2015 | Cogswell et al. |
| 9,320,811 B2* | 4/2016 | Jure-Kunkel .... A61K 39/39541 |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,492,539 B2 | 11/2016 | Korman et al. |
| 9,492,540 B2 | 11/2016 | Korman et al. |
| 9,714,290 B2 | 7/2017 | Jones et al. |
| 9,856,320 B2 | 1/2018 | Cogswell et al. |
| 9,963,508 B2 | 5/2018 | Hanson et al. |
| 10,030,064 B2 | 7/2018 | Jing et al. |
| 10,066,013 B2 | 9/2018 | Chen et al. |
| 10,072,082 B2 | 9/2018 | Cogswell et al. |
| 2003/0086930 A1 | 5/2003 | Mueller et al. |
| 2005/0042223 A1 | 2/2005 | Lee et al. |
| 2007/0065425 A1* | 3/2007 | Behrens ............. C07K 16/4241 424/131.1 |
| 2009/0252741 A1 | 10/2009 | Liu et al. |
| 2011/0091483 A1 | 4/2011 | Beall |
| 2014/0105914 A1 | 4/2014 | Jones et al. |
| 2014/0234331 A1 | 8/2014 | Korman et al. |
| 2014/0245692 A1 | 9/2014 | Bowers et al. |
| 2014/0302581 A1 | 10/2014 | Arunakumari et al. |
| 2015/0079100 A1 | 3/2015 | Roy et al. |
| 2015/0156025 A1 | 6/2015 | Zhu et al. |
| 2016/0000863 A1 | 1/2016 | Rodr guez Fern ndez-Alba et al. |
| 2016/0158356 A1 | 6/2016 | Honjo et al. |
| 2016/0222121 A1 | 8/2016 | Johnson et al. |
| 2016/0237154 A1 | 8/2016 | Gray et al. |
| 2016/0257753 A1 | 9/2016 | Korman et al. |
| 2016/0297885 A1* | 10/2016 | Kuo .................... A61K 31/454 |
| 2017/0088615 A1 | 3/2017 | Korman et al. |
| 2017/0088626 A1 | 3/2017 | Jure-Kunkel et al. |
| 2017/0158776 A1 | 6/2017 | Feltquate et al. |
| 2017/0216433 A1 | 8/2017 | Li et al. |
| 2018/0037651 A1* | 2/2018 | Attar ................. C07K 16/2809 |
| 2019/0161548 A1 | 5/2019 | Johnson et al. |
| 2019/0185569 A1 | 6/2019 | Li et al. |
| 2019/0321466 A1 | 10/2019 | Li et al. |

FOREIGN PATENT DOCUMENTS

| | | |
|---|---|---|
| CN | 103547595 A | 1/2014 |
| CN | 104479019 A | 4/2015 |
| CN | 104974253 A | 10/2015 |
| CN | 104987421 A | 10/2015 |
| CN | 105175544 A | 12/2015 |
| CN | 105175545 A | 12/2015 |
| CN | 105754990 A | 7/2016 |
| CN | 106967172 A | 7/2017 |
| CN | 106977602 A | 7/2017 |
| EP | 0865293 A1 | 9/1998 |
| EP | 1141028 A2 | 10/2001 |
| EP | 1212422 A2 | 6/2002 |
| EP | 1262193 A1 | 12/2002 |
| EP | 1513794 A2 | 3/2005 |
| EP | 1537878 A1 | 6/2005 |
| EP | 1639010 A2 | 3/2006 |
| EP | 1869067 A1 | 12/2007 |
| EP | 1896582 A1 | 3/2008 |
| EP | 2112166 A2 | 10/2009 |
| EP | 2161336 A1 | 3/2010 |
| EP | 2206517 A1 | 7/2010 |
| EP | 2240204 A1 | 10/2010 |
| EP | 2243493 A1 | 10/2010 |
| EP | 2418278 A2 | 2/2012 |
| EP | 2439272 A2 | 4/2012 |
| EP | 2439273 A2 | 4/2012 |
| EP | 2501822 A2 | 9/2012 |
| EP | 2850102 A1 | 3/2015 |
| EP | 3049442 A1 | 8/2016 |
| EP | 3114144 A1 | 1/2017 |
| EP | 3142697 A1 | 3/2017 |
| EP | 3214175 A1 | 9/2017 |
| EP | 3309175 A1 | 4/2018 |
| JP | 2008-074859 A | 4/2008 |
| JP | 2013-032387 A | 2/2013 |
| JP | 2014-500004 A | 1/2014 |
| JP | 2014-512809 A | 5/2014 |
| KR | 10-2014-0033013 A | 3/2014 |
| WO | WO-95/33770 A1 | 12/1995 |
| WO | WO-96/34090 A1 | 10/1996 |
| WO | WO-97/20574 A1 | 6/1997 |
| WO | WO-98/42752 A1 | 10/1998 |
| WO | WO-2000/037504 A2 | 6/2000 |
| WO | WO-01/14424 A2 | 3/2001 |
| WO | WO-01/54732 A1 | 8/2001 |
| WO | WO-03/086459 A1 | 10/2003 |
| WO | WO-04/004771 A1 | 1/2004 |
| WO | WO-04/029069 A2 | 4/2004 |
| WO | WO-05/003298 A2 | 1/2005 |
| WO | WO-05/092380 A2 | 10/2005 |
| WO | WO-06/110277 A1 | 10/2006 |
| WO | WO-06/121168 A1 | 11/2006 |
| WO | WO-07/113648 A2 | 10/2007 |
| WO | WO-09/100140 A1 | 8/2009 |
| WO | WO-2009/134776 A2 | 11/2009 |
| WO | WO-2010/036959 A2 | 4/2010 |
| WO | WO-11/044180 A1 | 4/2011 |
| WO | WO-11/045704 A1 | 4/2011 |
| WO | WO-11/062926 A2 | 5/2011 |
| WO | WO-2011/113019 A2 | 9/2011 |
| WO | WO-2012/038606 A1 | 3/2012 |
| WO | WO-2012/120125 A1 | 9/2012 |
| WO | WO-2012/135408 A1 | 10/2012 |
| WO | WO-2012/145493 A1 | 10/2012 |
| WO | WO-13/003761 A1 | 1/2013 |
| WO | WO-13/142796 A2 | 9/2013 |
| WO | WO-13/173223 A1 | 11/2013 |
| WO | WO-2014/022758 A1 | 2/2014 |
| WO | WO-2014/209804 A1 | 12/2014 |
| WO | WO-15/048312 A1 | 4/2015 |
| WO | WO-2015/085847 A1 | 6/2015 |
| WO | WO-2015/101587 A1 | 7/2015 |
| WO | WO-2015/112800 A1 | 7/2015 |
| WO | WO-15/134605 A1 | 9/2015 |
| WO | WO-15/176033 A1 | 11/2015 |
| WO | WO-2016/015675 A1 | 2/2016 |
| WO | WO-16/100561 A2 | 6/2016 |
| WO | WO-16/131769 A2 | 8/2016 |
| WO | WO-16/183469 A1 | 11/2016 |
| WO | WO-2016/180034 A1 | 11/2016 |
| WO | WO-2017/106061 A1 | 6/2017 |
| WO | WO-17/132508 A1 | 8/2017 |
| WO | WO-2017/128534 A1 | 8/2017 |
| WO | WO-2018/036472 A1 | 3/2018 |
| WO | WO-2018/036473 A1 | 3/2018 |

OTHER PUBLICATIONS

The Biology Project. Aspartic Acid D (ASP). www.biology.arizona. edu, 1 Page, Sep. 24, 2003 (Year: 2003).*

(56) References Cited

OTHER PUBLICATIONS

Omasa, T., et al. Cell engineering and cultivation of Chinese hamster ovary (CHO) cells. Current Pharmaceutical Biotechnology. 11 (3), Abstract, Apr. 2010 (Year: 2010).*
World Health Organization. General policies for monoclonal antibodies. Program on International Nonproprietary Names, 4 pages, Dec. 18, 2009 (Year: 2009).*
Woof, J and Burton D. Human antibody-Fc receptor interactions illuminated by crystal structures. Nature Reviews Immunology. 4, pp. 89-99, Feb. 1, 2004 (Year: 2004).*
Bever, C., et al. VHH antibodies: emerging reagents for the analysis of environmental chemicals. Analytical and Bioanalytical Chemistry. 408, pp. 5985-6002, May 21, 2006 (Year: 2006).*
Toughiri, R., et al. Comparing domain interactions within antibody Fabs with kappa and lambda light chains. MABS. 8(7) Abstract and pp. 1276-1285, published online Jul. 25, 2016 (Year: 2016).*
Smith and Crowe. Use of human hybridoma technology to isolate human monoclonal antibodies. Microbiology Spectrum. 3(1) 12 pages, Jan. 30, 2015 (Year: 2015).*
Buchbinder et al. CTLA-4 and PD-1 pathways. Am J Clin Oncol 39: 98-106, 2016.*
Mocellin et al. CTLA-4 blockade and the renaissance of cancer immunotherapy. Biochim Biophys Acta 1836: 187-196, 2013.*
Rowe et al. Cytotoxic T-lymphocyte antigen 4 blockade augments the T-cell response primed by attenuated Listeria monocytogenes resulting in more rapid clearance of virulent bacterial challenge. Immunol 128: e471-e478, 2008.*
Wykes et al. Immune checkpoint blockade in infectious diseases. Nature Rev Immunol 18: 91-104, 2018.*
Alfthan, Kaija et al., "Properties of a single-chain antibody containing different linker peptides," Protein Eng. 8:725-731 (1995).
Bird, Robert et al., "Single-chain antigen-binding proteins," Science 242:423-426 (1988).
Brummell, David A. et al., "Probing the combining site of an anti-carbohydrate antibody by saturation-mutagenesis: role of the heavy-chain CDR3 residues," Biochemistry 1993, 32:1180-1187.
Burks, Elizabeth A. et al., "In vitro scanning saturation mutagenesis of an antibody binding pocket," Proc. Natl Acad. Sci. USA 1997, vol. 94, pp. 412-417.
Calabró, Luana et al., "CTLA4 blockade in mesothelioma: finally a competing strategy over cytotoxic/target therapy?," Cancer Immunology Immunother, Springer, Berlin/Heidelberg, 2014, vol. 64, No. 1, pp. 105-112.
Choi, Ingrid et al., "Recombinant chimeric OKT3 scFv IgM antibodies mediate immune suppression while reducing T cell activation in vitro," Eur. J. Immunol. 2001, 31:94-106.
Chothia, Cyrus et al., "Conformations of immunoglobulin hypervariable regions," Nature vol. 342, 1989, pp. 878-883.
Chothia, Cyrus et al., "Canonical structures for the hypervariable regions of immunoglobulins," J. Mol. Biol., 1987. 196, pp. 901-917.
Clark, Mike et al., "Antibody humanization: a case of the 'Emperor's new clothes'?," Immunol. Today, 2000, vol. 21, pp. 397-402.
Du, T et al., "Tumor-specific oncolytic adenoviruses expressing granulocyte macrophage colony-stimulating factor for anti-CTLA4 antibody for the treatment of cancers," Cancer Gene Therapy, 2014, vol. 21, No. 8, pp. 340-348.
Examination Report No. 1 dated Oct. 26, 2017 in corresponding AU Appl. No. 2015295936.
Examination Report dated Oct. 5, 2018 in corresponding CL Appl. No. 00250-2017.
Fransen, Marieke F. et al., "Controlled local delivery of CTLA-4 blocking antibody induces CD8+ T-cell-dependent tumor eradication and decreases risk of toxic side effects," Clinical Cancer Research, 2013, vol. 19, No. 19 pp. 5381-5389.
Fransen et al., "Local immunomodulation for cancer therapy: providing treatment where needed," Oncoimmunology, 2013, vol. 2, No. 11, e26493, 4 pages.
Grosso, Joseph F. et al., "CTLA-4 blockade in tumor models: an overview of preclinical and translational research," Cancer Immunity, 2013, 13:5: 14 pages.
Hardcastle, Jayson J. et al., "Modulation of innate immunity with the anti-CTLA4 antibody ipilimumab (Ipi) in measles virotherapy for glioblastoma," Molecular Therapy, vol. 21, Suppl. 1, 2013, pp. S9.
Hodi, F. Stephen et al., "Improved survival with ipilimumab in patients with metastatic melanoma," New England Journal Of Medicine, 2010, vol. 363, No. 8, pp. 711-723.
Holliger, Philipp et al., "Diabodies: Small bivalent and bispecific antibody fragments," Proc. Natl. Acad. Sci. USA, Jul. 1993, 90(14): 6444-6448.
Hu, Shi-Zhen et al., "Minibody: a novel engineered anti-carcinoembryonic antigen antibody fragment (single-chain Fv-$C_H3$) which exhibits rapid, high-level targeting of Xenografts," Cancer Research, Jul. 1, 1996, 56:3055-3061.
Huston, James S. et al., "Protein engineering of antibody binding sites: recovery of specific activity in an anti-digoxin single-chain Fv analogue produced in Escherichia coli," Proc. Natl. Acad. Sci. USA, 1988, vol. 85, pp. 5879-5883.
International Search Report dated Nov. 20, 2015 in corresponding International Appl. No. PCT/CN2015/085721.
Jones, Peter T. et al., "Replacing the complementarity-determining regions in a human antibody with those from a mouse," Nature, 1986, vol. 321, pp. 522-525.
Kipriyanov, Sergey M. et al., "Bispecific tandem diabody for tumor therapy with improved antigen binding and pharmacokinetics," J. Mol. Biol., 1999, 293:41-56.
Kobayashi, Hiroyuki et al., "Tryptophan H33 plays an important role in pyrimidine (6-4) pyrimidone photoproduct binding by a high-affinity antibody," Protein Eng.1999, 12 (10):879-884.
Kohler et al., "Continuous cultures of fused cells secreting antibody of predefined specificity," Nature 256:495-497 (1975).
Lipson, Evan J. et al., "Ipilimumab: an anti-CTLA-4 antibody for metastatic melanoma," Clin. Cancer Res., 2011, 17(22), pp. 6958-6962.
Maki, Robert G. et al., "A pilot study of anti-CTLA4 antibody ipilimumab in patients with synovial sarcoma," Sarcoma, vol. 2013, Article ID 168145, 2013, 8 pages.
Mellman, Ira et al., "Cancer immunotherapy comes of age," Nature, vol. 480, No. 7378, 2011, pp. 480-489.
Menzies, Alexander M. et al., "Recent advances in melanoma systemic therapy. BRAF inhibitors, CTLA4 antibodies and beyond," European Journal of Cancer, 2013, vol. 49, No. 15, pp. 3229-3241.
Morrison, Sherie L. et al., "Chimeric human antibody molecules: mouse antigen-binding domains with human constant region domains," Proc. Natl. Acad. Sci. USA, 1984, 81:6851-6855.
Myers, Eugene W. et al., "Optimal alignments in linear space," Comput. Appl. Biosci., 1988, 4:11-17.
Needleman, Saul B. et al., "A general method applicable to the search for similarities in the amino acid sequence of two proteins," J. Mol. Biol., 1970, 48:443-453.
Office Action dated Mar. 14, 2017 in corresponding CO Appl. No. NC2017/0000754.
Office Action dated Apr. 11, 2017 in corresponding VN Appl. No. 1-2017-00481.
Office Action dated Dec. 28, 2017 in corresponding CA Appl. No. 2,956,000.
Office Action dated Jul. 3, 2018 in corresponding EA Appl. No. 201790288.
Office Action dated Jul. 30, 2018 in corresponding GE Appl. No. AP2015014437.
Office Action dated Sep. 4, 2018 in corresponding JP Appl. No. 2017-525666.
Office Action dated Sep. 6, 2017 in corresponding TH Appl. No. 1701000544.
Office Action dated May 9, 2018 in corresponding KR Appl. No. 10-2017-7005688.
Poljak, Roberto J. et al., "Production and structure of diabodies," Structure, 1994, 2:1121-1123.
Presta, Leonard G., "Antibody engineering," Curr. Op. in Struct. Biol., 1992, 2:593-596.
Previous Search Results dated Aug. 1, 2014 in priority application No. CN201410377352 (http://cpquery.sipo.gov.cn).

(56) References Cited

OTHER PUBLICATIONS

Riechmann, Lutz et al., "Reshaping human antibodies for therapy," Nature, 1988, vol. 332, pp. 323-327.
Search Report dated Jan. 30, 2017 in corresponding PA Appl. No. 91482-01.
Shao, Kun et al., "Nanoparticle-based immunotherapy for cancer," ACS Nano, 2015, vol. 9, No. 1, pp. 16-30.
Supplementary Search Report dated Feb. 13, 2018 in corresponding EP Appl. No. 15827441.5.
Ward, E. Sally et al., "Binding activities of a repertoire of single immunoglobulin variable domains secreted from Escherichia coli", Nature, 1989, vol. 341, pp. 544-546.
Written Opinion dated Feb. 5, 2018 in corresponding SG Appl. No. 11201700819Q.
Xu et al., "Preparation and characterization of a chimeric anti-human CTLA-4 monoclonal antibody," Second Military Medical University, Shanghai 200433, China (2012), pp. 359-364.
Office Action dated Dec. 28, 2018 in corresponding EA App. No. 201790288.
Marri et al., Human Biochemistry, "Mir" 1993, vol. 1, p. 34.
International Search Report dated Nov. 6, 2017 for PCT/US2017/047721.
Written Opinion dated Nov. 6, 2017 for PCT/US2017/047721.
International Preliminary Report on Patentability dated Feb. 26, 2019 for PCT/US2017/047721.
Extended European Search Report dated Apr. 7, 2020 in corresponding EP Appl. No. 17844198.6.
Hanaizi, Z., et al., "The European Medicines Agency review of ipilimumab (Yervoy) for the treatment of advanced (unresectable or metastatic) melanoma in adults who have received prior therapy: Summary of the scientific assessment of the Committee for Medicinal Products for Human Use," European Journal of Cancer, 2012, 48: 237-242.
Office Action dated Dec. 16, 2020 in corresponding EP Appl. No. 17844198.6.
Office Action dated Dec. 17, 2019 in corresponding CA Appl. No. 2,956,000.
Office Action dated Mar. 10, 2020 in corresponding SA Appl. No. 517380820.
Office Action dated Apr. 2, 2019 in corresponding NZ Appl. No. 729158.
Office Action dated Oct. 11, 2019 in corresponding NZ Appl. No. 729158.
Office Action dated Sep. 13, 2019 in corresponding EA Appl. No. 201790288.
Office Action dated Nov. 13, 2019 in corresponding IN Appl. No. 201747003171.
Office Action dated Jan. 21, 2020 in corresponding JP Appl. No. 2019-036646.
Office Action received Mar. 12, 2020 in corresponding PE Appl. No. 000155-2017/DIN.
Office Action dated Apr. 20, 2020 in corresponding CN Appl. No. 201580040171.X.
Zhou et al., "CTLA-4 monoclonal antibody-targeted passive immunotherapy for tumor," Chinese Clinical Oncology, 2013, 18(3): 268-272 [Partial translation].
Persson et al., "Intratumoral Expression of CTLA4 Monoclonal Antibody Induces Immunosuppressive NKT Cells in a Mouse Model of Breast Cancer with Tolerance to Her2/neu," Molecular Therapy, 2011, 19(Suppl 1): S88-S89.
Office Action dated Jun. 2, 2020 in corresponding BB Appl. No. 2001/1872.
Office Action dated Sep. 15, 2020 in corresponding BR Appl. No. BR112017002080.
Office Action dated May 29, 2020 in corresponding PH Appl. No. 1/2017/500190.
Office Action dated Nov. 13, 2020 in corresponding MD Appl. No. a20170022.
Office Action dated Dec. 23, 2020 in corresponding VN Appl. No. 1-2017-00481.
Office Action dated Oct. 23, 2020 in corresponding SA Appl. No. 517380820.
Office Action dated Jul. 16, 2020 in corresponding MX Appl. No. MX/a/2017/001446.
Office Action dated Dec. 18, 2020 in corresponding MX Appl. No. MX/a/2017/001446 [Translation only].
Office Action dated May 20, 2020 in corresponding MD Appl. No. a20170022.
Office Action dated Feb. 8, 2021 in corresponding CA Appl. No. 2,956,000.
Office Action dated Jan. 19, 2021 in corresponding HN Appl. No. 2017-000149.
Office Action dated Jan. 25, 2021 in corresponding CN Appl. No. 201580040171.X.
Okawa, S., et al., "Pembrolizumab-induced Autoimmune Hemolytic Anemia and Hemophagocytic Lymphohistiocytosis in Non-small Cell Lung Cancer," Intern. Med., 2019, 58: 699-702.
Tanios, G., et al., "Autoimmune hemolytic anemia associated with the use of immune checkpoint inhibitors for cancer: 68 cases from the Food and Drug Administration database and review," Eur. J. Haematol., 2019, 102(2): 157-162.
Altshuler, E. P., et al., "Generation of Recombinant Antibodies and Means for Increasing Their Affinity," Biochemistry (Moscow), 2010, 75(13): 1584-1605.
Hoogenboom, H., "Selecting and screening recombinant antibody libraries," Nature Biotechnology, 2005, 23(9): 1105-1116.
Orcutt, K. D., et al., "A modular IgG-scFv bispecific antibody topology," Protein Engineering, Design & Selection, 2010, 23(4): 221-228.
Brahmer, J., et al., "Nivolumab: targeting PD-1 to bolster antitumor immunity," Future Oncol., 2015, 11(9): 1307-1326.
McDermott, J., et al., "Pembrolizumab: PD-1 Inhibition as a Therapeutic Strategy in Cancer," Drugs of Today, 2015, 51(1): 7-20.
U.S. National Library of Medicine. (Mar. 9, 2015). "Study of REGN2810 (Anti-PD-1) in Patients With Advanced Malignancies," ClinicalTrials.gov, Identifier NCT02383212, https://clinicaltrials.gov/ct2/show/NCT02383212.
Miao, A., et al., "The role of immunosuppressive receptor PD-1 in patients with aplastic anemia," Jiangsu Medicine Journal, 2009, 35(6); 626-627. [Abstract only].
International Search Report for International Patent Application No. PCT/CN2017/098466, dated Nov. 14, 2017. [English translation].
Written Opinion for International Patent Application No. PCT/CN2017/098466, dated Nov. 14, 2017. [English translation].
International Search Report for International Patent Application No. PCT/CN2017/098465, dated Oct. 31, 2017. [English translation].
Written Opinion for International Patent Application No. PCT/CN2017/098465, dated Oct. 31, 2017. [English translation].
Chan, R., et al., "Abstract 5021: Regulatory T-cells and effects of anti-CTLA4 and anti-PD1 therapy in a transgenic murine model of neuroblastoma," Proceedings of the 105th Annual Meeting of the American Association for Cancer Research, Apr. 5-9, 2014, San Diego, CA; Cancer Res., 2014, 74(19 Suppl): Abstract nr 5021. doi:10.1158/1538-7445.AM2014-5021.
Blatter, S., et al., "Abstract 736: Combining PD1- and CTLA4-inhibiting antibodies with cisplatin or PARP inhibition in an attempt to eradicate BRCA1-deficient mouse mammary tumors," Proceedings of the 106th Annual Meeting of the American Association for Cancer Research, Apr. 18-22, 2015, Philadelphia, PA; Cancer Res., 2015, 75(15 Suppl): Abstract nr 736. doi:10.1158/1538-7445. AM2015-736.
Office Action dated Mar. 31, 2021 in U.S. Appl. No. 16/327,076.
Notice of Allowance dated Nov. 24, 2021 in U.S. Appl. No. 16/327,076 (corresponds to US Pub. 20190185569).
Office Action dated Apr. 12, 2022 in U.S. Appl. No. 16/327,076 (corresponds to US Pub. 20190185569).

\* cited by examiner

ANTI-CTLA4 ANTIBODIES

CROSS-REFERENCE TO RELATED APPLICATIONS

This application is a U.S. National Stage application under 35 U.S.C. § 371 of International Application PCT/US2017/047721, filed on Aug. 21, 2017, which claims priority to International Application PCT/CN2016/096357, filed on Aug. 23, 2016.

SEQUENCE LISTING

The instant application contains a Sequence Listing which has been submitted electronically in ASCII format and is hereby incorporated by reference in its entirety. Said ASCI copy, created on Feb. 21, 2019, is named 214572_0002_582624_SL_ST25 and is 35,764 bytes in size.

FIELD OF THE INVENTION

The present invention belongs to the fields of tumor therapy and molecular immunology. The present invention relates to an anti-CTLA4 antibody, pharmaceutical composition and use thereof.

BACKGROUND OF THE INVENTION

Cytotoxic T lymphocyte associated antigen 4 (abbreviated as CTLA4) has very close relationship with the CD28 molecule in gene structure, chromosome location, sequence homology and gene expression. Both of them are receptors for the co-stimulative molecule B7, mainly expressed on the surface of activated T cells. After binding to B7, CTLA4 can inhibit the activation of mouse and human T cells, playing a negative regulating role in the activation of T cells.

CTLA4 mAbs or CTLA4 ligands can prevent CTLA4 from binding to its native ligands, thereby blocking the transduction of the T cell negative regulating signal by CTLA4 and enhancing the responsiveness of Tcells to various antigens. In this aspect, results from in vivo and in vitro studies are substantially in concert. At present, there are some CTLA4 mAbs being tested in clinical trials for treating prostate cancer, bladder cancer, colorectal cancer, cancer of gastrointestinal tract, liver cancer, malignant melanoma, etc. (CTLA-4 blockade in tumor models: an overview of preclinical and translational research. Grosso J F., Jure-Kunkel M N., Cancer Immun. 2013; 13:5. Epub 2013 January 22).

Interleukin 2 (IL-2) is produced by T cells. It is a growth factor regulating a subgroup of T cells. It is also an important factor modulating immune response. It can promote and activate the expansion of B cells, and involves in antibody reaction, hematopoiesis and tumor surveillance. Recombinant human IL-2 has been approved by US FDA for the treatment of malignant tumors (including melanoma, kidney tumor, etc.). It is also under clinical studies of treating chronic viral infection (Pharmacologic administration of interleukin-2. Chavez, A. R., et al., Ann N Y Acad Sci, 2009. 1182: 14-27). In experiments in vitro, CTLA4 mAbs can specifically relieve the immunosuppression on the body by CTLA4, activate T cells, and induce IL-2 production, and thus has wide prospect in the gene therapy against tumor and the like.

As important factors affecting the function of T cells, CTLA4 and CTLA4 mAbs can produce specific therapeutic effect on diseases by interfering with the immune microenvironment in the body. They have high efficacy and remedy the deficiency of traditional medication, opening a novel pathway of gene therapy. CTLA4 and CTLA4 mAbs are being tested in experiments and various stages of clinical trials. For example, in autoimmune diseases, they effectively inhibited airway hyperresponsiveness in an animal model of asthma, prevented the development of rheumatic diseases, mediated immune tolerance to an allograft in the body, and the like. On the other hand, although biological gene therapy has not shown any adverse effect in short term clinical trials, attention should be paid to the potential effect after long term application. For example, excessive blockade of CTLA4-B7 signaling by CTLA4 mAbs may result in the development of autoimmune diseases. As antibodies can specifically bind to their antigens and induce the lysis of target cells or block the progress of pathology, development and utilization of drugs based on antibodies, especially humanized antibodies have important significance in the clinical treatment of malignant tumors and other immune diseases in humans.

SUMMARY OF THE INVENTION

The inventors identified the hybridoma cell line LT002 (CTLA4-4G10) and deposited it at China Center for Typical Culture Collection (CCTCC) on Jun. 16, 2015, under the deposit number CCTCC NO: C201587. The inventors surprisingly found that: the hybridoma cell line LT002 was capable of secreting and producing a specific monoclonal antibody specifically binding CTLA4 (designated as 4G10), and said monoclonal antibody could block the binding of CTLA4 to B7 very effectively. Furthermore, the inventor generated various anti-CTLA4 humanized antibodies, including antibodies designated 4G10H1L1, 4G10H3L3, 4G10H4L3 and 4G10H5L3.

Thus, the following inventions are provided.

In one embodiment, the invention provides an antibody or antigen binding fragment thereof that binds to human CTLA4, comprising a heavy chain variable region and/or a light chain variable region. In one embodiment, the invention comprises an antibody or antigen binding fragment thereof that binds to human CTLA4, comprising a heavy chain variable region and/or a light chain variable region, wherein the heavy chain variable region comprises:
  an HCDR1 comprising the amino acid sequence of SEQ ID NO: 21 or SEQ ID NO: 27,
  an HCDR2 comprising the amino acid sequence of SEQ ID NO: 22 or SEQ ID NO: 28, and
  an HCDR3 comprising the amino acid sequence of SEQ ID NO: 23 or SEQ ID NO: 29;
and/or the light chain variable region comprises:
  an LCDR1 comprising the amino acid sequence of SEQ ID NO: 24 or SEQ ID NO:30,
  an LCDR2 comprising the amino acid sequence of SEQ ID NO: 25 or SEQ ID NO:31, and
  an LCDR3 comprising the amino acid sequence of SEQ ID NO:26 or SEQ ID NO:32.

In one embodiment, the antibody or antigen binding fragment thereof comprises a heavy chain variable region comprising: an HCDR1 comprising the amino acid sequence of SEQ ID NO: 21, an HCDR2 comprising the amino acid sequence of SEQ ID NO: 22, and an HCDR3 comprising the amino acid sequence of SEQ ID NO: 23; and/or a light chain variable region comprising: an LCDR1 comprising the amino acid sequence of SEQ ID NO: 24, an LCDR2 comprising the amino acid sequence of SEQ ID NO: 25, and an LCDR3 comprising the amino acid sequence of SEQ ID NO:26.

In another embodiment, the antibody or antigen binding fragment thereof comprises a heavy chain variable region comprising: an HCDR1 comprising the amino acid sequence of SEQ ID NO: 21 (wherein $X_1$=M), an HCDR2 comprising the amino acid sequence of SEQ ID NO: 22 (wherein $X_1$=N or D, $X_2$=T or D, $X_3$=A and $X_4$=Q), and an HCDR3 comprising the amino acid sequence of SEQ ID NO: 23; and/or
a light chain variable region comprising: an LCDR1 comprising the amino acid sequence of SEQ ID NO: 24 (wherein $X_1$=P), an LCDR2 comprising the amino acid sequence of SEQ ID NO: 25 (wherein $X_1$=K and $X_2$=S), and an LCDR3 comprising the amino acid sequence of SEQ ID NO:26 (wherein $X_1$=W and $X_2$=W). In another embodiment, the antibody or antigen binding fragment thereof comprises a heavy chain variable region comprising: an HCDR1 comprising the amino acid sequence of SEQ ID NO: 21 (wherein $X_1$=M), an HCDR2 comprising the amino acid sequence of SEQ ID NO: 22 (wherein $X_1$=N, $X_2$=T, $X_3$=A and $X_4$=Q), and an HCDR3 comprising the amino acid sequence of SEQ ID NO: 23; and/or a light chain variable region comprising: an LCDR1 comprising the amino acid sequence of SEQ ID NO: 24 (wherein $X_1$=P), an LCDR2 comprising the amino acid sequence of SEQ ID NO: 25 (wherein $X_1$=K and $X_2$=S), and an LCDR3 comprising the amino acid sequence of SEQ ID NO:26 (wherein $X_1$=W and $X_2$=W). In another embodiment, the antibody or antigen binding fragment thereof comprises a heavy chain variable region comprising: an HCDR1 comprising the amino acid sequence of SEQ ID NO: 27, an HCDR2 comprising the amino acid sequence of SEQ ID NO: 28, and an HCDR3 comprising the amino acid sequence of SEQ ID NO: 29; and/or a light chain variable region comprising: an LCDR1 comprising the amino acid sequence of SEQ ID NO: 30, an LCDR2 comprising the amino acid sequence of SEQ ID NO: 31, and an LCDR3 comprising the amino acid sequence of SEQ ID NO:32. In another embodiment, the antibody or antigen binding fragment thereof comprises a heavy chain variable region comprising: an HCDR1 comprising the amino acid sequence of SEQ ID NO: 27, an HCDR2 comprising the amino acid sequence of SEQ ID NO: 28 (wherein $X_1$=N or D, $X_2$=T or D), and an HCDR3 comprising the amino acid sequence of SEQ ID NO: 29; and/or a light chain variable region comprising: an LCDR1 comprising the amino acid sequence of SEQ ID NO: 30, an LCDR2 comprising the amino acid sequence of SEQ ID NO: 31, and an LCDR3 comprising the amino acid sequence of SEQ ID NO:32 (wherein $X_1$=W and $X_2$=W). In another embodiment, the antibody or antigen binding fragment thereof comprises a heavy chain variable region comprising: an HCDR1 comprising the amino acid sequence of SEQ ID NO: 27, an HCDR2 comprising the amino acid sequence of SEQ ID NO: 28 (wherein $X_1$=N, $X_2$=T), and an HCDR3 comprising the amino acid sequence of SEQ ID NO: 29; and/or a light chain variable region comprising: an LCDR1 comprising the amino acid sequence of SEQ ID NO: 30, an LCDR2 comprising the amino acid sequence of SEQ ID NO: 31, and an LCDR3 comprising the amino acid sequence of SEQ ID NO:32 (wherein $X_1$=W and $X_2$=W). In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from a Fab, a Fab', an F(ab')$_2$, a Fd, an Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO: 4. In one embodiment, the invention provides an antibody or antigen binding fragment thereof that binds to human CTLA4, comprising a heavy chain variable region and/or a light chain variable region, wherein the light chain variable region comprises SEQ ID NO: 6. In one embodiment, the invention provides an antibody or antigen binding fragment thereof that binds to human CTLA4, comprising a heavy chain variable region and a light chain variable region, wherein the heavy chain variable region comprises SEQ ID NO: 4 and the light chain variable region comprises SEQ ID NO: 6. In one embodiment, the invention provides an antibody or antigen binding fragment thereof that binds to human CTLA4, comprising a heavy chain variable region and/or a light chain variable region, wherein the heavy chain variable region comprises at least 90%, 95%, 96%, 97%, 98% or 99% identity to SEQ ID NO: 4 and/or the light chain variable region comprises at least 90%, 95%, 96%, 97%, 98% or 99% identity to SEQ ID NO: 6. In one embodiment, the invention comprises an antibody or antigen binding fragment thereof that binds to human CTLA4, comprising a heavy chain variable region and/or a light chain variable region, wherein the heavy chain variable region comprises 1, 2, 3, 4, 5, 6, 7, 8, 9 or 10 amino acid substitutions in the variable heavy chain of SEQ ID NO: 4 and/or the light chain variable region comprises 1, 2, 3, 4, 5, 6, 7, 8, 9 or 10 amino acid substitutions in the variable light chain of SEQ ID NO: 6. In some embodiments, the sequence variation or amino acid substitutions in SEQ ID NO: 4 or SEQ ID NO: 6 occur outside of the CDR regions identified in SEQ ID NOs: 27-32. In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from a Fab, a Fab', a F(ab')$_2$, a Fd, a Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO:8. In one embodiment, the invention provides an antibody or antigen binding fragment thereof that binds to human CTLA4, comprising a heavy chain variable region and/or a light chain variable region, wherein the light chain variable region comprises SEQ ID NO:10. In one embodiment, the invention provides an antibody or antigen binding fragment thereof that binds to human CTLA4, comprising a heavy chain variable region and a light chain variable region, wherein the heavy chain variable region comprises SEQ ID NO:8 and the light chain variable region comprises SEQ ID NO:10. In one embodiment, the invention provides an antibody or antigen binding fragment thereof that binds to human CTLA4, comprising a heavy chain variable region and/or a light chain variable region, wherein the heavy chain variable region comprises at least 90%, 95%, 96%, 97%, 98% or 99% identity to SEQ ID NO: 8 and/or the light chain variable region comprises at least 90%, 95%, 96%, 97%, 98% or 99% identity to SEQ ID NO: 10. In one embodiment, the invention comprises an antibody or antigen binding fragment thereof that binds to human CTLA4, comprising a heavy chain variable region and/or a light chain variable region, wherein the heavy chain variable region comprises 1, 2, 3, 4, 5, 6, 7, 8, 9 or 10 amino acid substitutions in the variable heavy chain of SEQ ID NOs: 8 and/or the light chain variable region comprises 1, 2, 3, 4, 5, 6, 7, 8, 9 or 10 amino acid substitutions in the variable light chain of SEQ ID NOs: 10. In some embodiments, the sequence variation or amino acid substitutions in SEQ ID NO: 8 or SEQ ID NO:10 occur outside of the CDR regions identified in SEQ ID NOs: 27-32. In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from a Fab, a Fab', a F(ab')$_2$, a Fd, a Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO:12. In one embodiment, the invention provides an antibody or antigen binding fragment thereof that binds to human CTLA4, comprising a heavy chain variable region and/or a light chain variable region, wherein the light chain variable region comprises SEQ ID NO:14. In one embodiment, the invention provides an antibody or antigen binding fragment thereof that binds to human CTLA4, comprising a heavy chain variable region and a light chain variable region, wherein the heavy chain variable region comprises SEQ ID NO:12 and the light chain variable region comprises SEQ ID NO:14. In one embodiment, the invention provides an antibody or antigen binding fragment thereof that binds to human CTLA4, comprising a heavy chain variable region and/or a light chain variable region, wherein the heavy chain variable region comprises at least 90%, 95%, 96%, 97%, 98% or 99% identity to SEQ ID NO: 12 and/or the light chain variable region comprises at least 90%, 95%, 96%, 97%, 98% or 99% identity to SEQ ID NO: 14. In one embodiment, the invention comprises an antibody or antigen binding fragment thereof that binds to human CTLA4, comprising a heavy chain variable region and/or a light chain variable region, wherein the heavy chain variable region comprises 1, 2, 3, 4, 5, 6, 7, 8, 9 or 10 amino acid substitutions in the variable heavy chain of SEQ ID NO: 12 and/or the light chain variable region comprises 1, 2, 3, 4, 5, 6, 7, 8, 9 or 10 amino acid substitutions in the variable light chain of SEQ ID NO: 14. In some embodiments, the sequence variation or amino acid substitutions in SEQ ID NO: 12 or SEQ ID NO: 14 occur outside of the CDR regions identified in SEQ ID NOs: 27-32. In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from an Fab, an Fab', an F(ab')$_2$, an Fd, an Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO:16. In one embodiment, the invention provides an antibody or antigen binding fragment thereof that binds to human CTLA4, comprising a heavy chain variable region and a light chain variable region, wherein the heavy chain variable region comprises SEQ ID NO:16 and the light chain variable region comprises SEQ ID NO:14. In one embodiment, the invention provides an antibody or antigen binding fragment thereof that binds to human CTLA4, comprising a heavy chain variable region and/or a light chain variable region, wherein the heavy chain variable region comprises at least 90%, 95%, 96%, 97%, 98% or 99% identity to SEQ ID NO: 16 and/or the light chain variable region comprises at least 90%, 95%, 96%, 97%, 98% or 99% identity to SEQ ID NO: 14. In one embodiment, the invention comprises an antibody or antigen binding fragment thereof that binds to human CTLA4, comprising a heavy chain variable region and/or a light chain variable region, wherein the heavy chain variable region comprises 1, 2, 3, 4, 5, 6, 7, 8, 9 or 10 amino acid substitutions in the variable heavy chain of SEQ ID NO: 16 and/or the light chain variable region comprises 1, 2, 3, 4, 5, 6, 7, 8, 9 or 10 amino acid substitutions in the variable light chain of SEQ ID NO: 14. In some embodiments, the sequence variation or amino acid substitutions in SEQ ID NO: 16 or SEQ ID NO: 14 occur outside of the CDR regions identified in SEQ ID NOs: 27-32. In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from an Fab, an Fab', an F(ab')$_2$, an Fd, an Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO:18. In one embodiment, the invention provides an antibody or antigen binding fragment thereof that binds to human CTLA4, comprising a heavy chain variable region and a light chain variable region, wherein the heavy chain variable region comprises SEQ ID NO:18 and the light chain variable region comprises SEQ ID NO:14. In one embodiment, the invention provides an antibody or antigen binding fragment thereof that binds to human CTLA4, comprising a heavy chain variable region and/or a light chain variable region, wherein the heavy chain variable region comprises at least 90%, 95%, 96%, 97%, 98% or 99% identity to SEQ ID NO: 18 and/or the light chain variable region comprises at least 90%, 95%, 96%, 97%, 98% or 99% identity to SEQ ID NO: 14. In one embodiment, the invention comprises an antibody or antigen binding fragment thereof that binds to human CTLA4, comprising a heavy chain variable region and/or a light chain variable region, wherein the heavy chain variable region comprises 1, 2, 3, 4, 5, 6, 7, 8, 9 or 10 amino acid substitutions in the variable heavy chain of SEQ ID NO: 18 and/or the light chain variable region comprises 1, 2, 3, 4, 5, 6, 7, 8, 9 or 10 amino acid substitutions in the variable light chain of SEQ ID NO: 14. In some embodiments, the sequence variation or amino acid substitutions in SEQ ID NO: 18 or SEQ ID NO: 14 occur outside of the CDR regions identified in SEQ ID NOs: 27-32. In one embodiment, the antibody or antigen binding fragment thereof is a humanized antibody comprising two heavy chain and two light chains. In one embodiment, the antibody or antigen binding fragment thereof is a humanized antibody comprising a human IgG1 constant domain. In one embodiment, the antibody or antigen binding fragment thereof is a humanized antibody comprising a human IgG2 constant domain. In one embodiment, the antibody or antigen binding fragment thereof is a humanized antibody comprising a human IgG4 constant domain. In another embodiment, the antibody or antigen binding fragment thereof is humanized antibody comprising a human IgG1 constant domain and a human kappa constant domain. In another embodiment, the antibody or antigen binding fragment thereof is selected from an Fab, an Fab', an F(ab')$_2$, an Fd, an Fv, a dAb, a complementarity determining region fragment, a single chain antibody (e.g., an scFv), or a diabody.

In one embodiment, the invention provides an antibody or antigen binding fragment thereof that binds to human CTLA4, comprising a heavy chain variable region and/or a light chain variable region, wherein the heavy chain variable region comprises SEQ ID NO: 19. In one embodiment, the invention provides an antibody or antigen binding fragment thereof that binds to human CTLA4, comprising a heavy chain variable region and/or a light chain variable region, wherein the light chain variable region comprises SEQ ID NO: 20. In one embodiment, the invention provides an antibody or antigen binding fragment thereof that binds to human CTLA4, comprising a heavy chain variable region and a light chain variable region, wherein the heavy chain variable region comprises SEQ ID NO: 19 and the light chain variable region comprises SEQ ID NO: 20.

In one embodiment, the antibody or antigen binding fragment of the invention (described above) is isolated.

In one embodiment, the antibody or antigen binding fragment of the invention (described above) is an antibody produced in a CHO cell.

In one embodiment, the antibody or antigen binding fragment of the invention (described above) binds to the human CTLA4 with a $K_D$ less than about $10^{-5}$ M, e.g., less than about $10^{-6}$ M, $10^{-7}$ M, $10^{-8}$ M, $10^{-9}$ M, $10^{-10}$ M or less as determined by surface plasmon resonance (e.g., BIACORE) or a similar technique (e.g. KinExa or OCTET). In one embodiment, the antibody or antigen binding fragment described above binds to the human CTLA4 with a $K_D$ of about $1\times10^{-9}$ M to about $1\times10^{-12}$ M as determined by surface plasmon resonance (e.g., BIACORE) or a similar technique (e.g. KinExa or OCTET).

In one embodiment, the antibody or antigen binding fragment thereof of the invention (described above) optionally has at least one of the following characteristics: detects the level of CTLA4 in a sample, cross-reacts with cyno CTLA4, blocks the binding of CTLA4 to B7, regulates (e.g., down-regulates) the activity of CTLA4 or the level of CTLA4, relieves the immunosuppression on the body by CTLA4, activates T lymphocytes, increases the expression of IL-2 in T lymphocytes; and/or increases the expression of IFN-γ in T lymphocytes.

In one embodiment, the invention relates to the hybridoma cell line LT002 deposited at China Center for Typical Culture Collection (CCTCC) on Jun. 16, 2015, under the deposit number CCTCC C201587.

In one embodiment, the invention relates to the monoclonal antibody produced by the hybridoma cell line LT002 deposited at China Center for Typical Culture Collection (CCTCC) on Jun. 16, 2015, under the deposit number CCTCC C201587.

The invention also relates to isolated polypeptides comprising the amino acid sequence of any one of SEQ ID NOs: 4, 6, 8, 10, 12, 14, 16, 18, 19 or 20.

The invention also relates to pharmaceutical compositions comprising any one of the antibodies or antigen binding fragments of the invention. In one embodiment, the invention comprises any one of the antibodies or antigen binding fragments of the invention, and further comprises a pharmaceutically acceptable carrier and/or excipient. In one embodiment, the invention comprises any one of the antibodies or antigen binding fragments of the invention, and further comprises a second therapeutic agent. The second therapeutic agent can be selected from the group consisting of: an anti-PD1 antibody or an antigen binding fragment thereof; an anti-LAG3 antibody or an antigen binding fragment thereof; an anti-VISTA antibody or an antigen binding fragment thereof; an anti-TIGIT antibody or an antigen binding fragment thereof; an anti-TIM3 antibody or an antigen binding fragment thereof; an anti-HVEM antibody or an antigen binding fragment thereof; an anti-CD27 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-SIRPa antibody or an antigen binding fragment thereof; an anti-ILT2 antibody or an antigen binding fragment thereof; an anti-ILT3 antibody or an antigen binding fragment thereof; an anti-ILT4 antibody or an antigen binding fragment thereof; and an anti-ILT5 antibody or an antigen binding fragment thereof; an anti-CD73 antibody or an antigen binding fragment thereof; and an anti-CD47 antibody or an antigen binding fragment thereof. In one embodiment, the anti-PD1 antibody or an antigen binding fragment thereof is selected from the group consisting of: pembrolizumab or an antigen binding fragment thereof and nivolumab or an antigen binding fragment thereof.

The invention also comprises a conjugate comprising an antibody or antigen binding fragment thereof according to the invention and a conjugated moiety. In one embodiment, the conjugated moiety is a detectable label. In one embodiment, the conjugated moiety is a radioisotope, a fluorescent substance, a luminescent substance, a chromogenic substance, or an enzyme.

The invention also comprises a kit comprising an antibody or antigen binding fragment thereof according to the invention, or a conjugate according to the invention and a second antibody which specifically recognizes said antibody or antigen binding fragment thereof. In one embodiment, the second antibody further comprises a detectable label, e.g., a radioisotope, a fluorescent substance, a luminescent substance, a chromogenic substance, or an enzyme.

The invention also comprises nucleic acid molecules encoding the antibodies or antigen binding fragments of the invention, or the polypeptides of the invention. In one embodiment, the invention comprises the nucleic acid sequence of SEQ ID NO:3. In another embodiment, the invention comprises the nucleic acid sequence of SEQ ID NO:5. In another embodiment, the invention comprises the nucleic acid sequence of SEQ ID NO:7. In another embodiment, the invention comprises the nucleic acid sequence of SEQ ID NO:9. In another embodiment, the invention comprises the nucleic acid sequence of SEQ ID NO:11. In another embodiment, the invention comprises the nucleic acid sequence of SEQ ID NO:13. In another embodiment, the invention comprises the nucleic acid sequence of SEQ ID NO:15. In another embodiment, the invention comprises the nucleic acid sequence of SEQ ID NO:17. The invention also comprises vectors comprising the nucleic acids of the invention, and host cells comprising the nucleic acids or the vectors of the invention.

The invention also comprises a method of producing an antibody or antigen binding fragment comprising: (i) culturing a host cell comprising a polynucleotide encoding the heavy chain and/or the light chain of any one of the antibodies or antigen binding fragments of the invention under conditions favorable to expression of the polynucleotide; and (ii) optionally, recovering the antibody or antigen binding fragment from the host cell and/or culture medium.

The invention also comprises a method of treating cancer in a human subject, comprising administering to the subject an effective amount of an antibody or antigen binding fragment of the invention, optionally in association with a further therapeutic agent or therapeutic procedure. The further therapeutic agent can be selected from the group consisting of: an anti-PD1 antibody or an antigen binding fragment thereof an anti-LAG3 antibody or an antigen binding fragment thereof an anti-VISTA antibody or an antigen binding fragment thereof an anti-TIGIT antibody or an antigen binding fragment thereof an anti-TIM3 antibody or an antigen binding fragment thereof an anti-HVEM antibody or an antigen binding fragment thereof an anti-CD27 antibody or an antigen binding fragment thereof an anti-CD137 antibody or an antigen binding fragment thereof an anti-OX40 antibody or an antigen binding fragment thereof an anti-CD28 antibody or an antigen binding fragment thereof an anti-PDL1 antibody or an antigen binding fragment thereof an anti-PDL2 antibody or an antigen binding fragment thereof an anti-GITR antibody or an antigen binding fragment thereof an anti-ICOS antibody or an antigen binding fragment thereof an anti-SIRPa antibody or an antigen binding fragment thereof an anti-ILT2 antibody or an antigen binding fragment thereof; an anti-ILT3 antibody or an antigen binding fragment thereof; an anti-ILT4 antibody or an antigen binding fragment thereof an anti-ILT5 antibody or an antigen binding fragment thereof an anti-CD73 antibody or an antigen binding fragment thereof and an anti-CD47 antibody or an antigen binding fragment thereof. In one embodiment, the anti-PD1 antibody or an antigen binding fragment thereof is selected from the group consisting of: pembrolizumab or an antigen binding fragment thereof and nivolumab or an antigen binding fragment thereof.

The invention also comprises a method of treating an infection or infectious disease in a human subject, comprising administering to the subject an effective amount of an antibody or antigen binding fragment of the invention, optionally in association with a further therapeutic agent or therapeutic procedure. The further therapeutic agent can be selected from the group consisting of: an anti-PD1 antibody or an antigen binding fragment thereof an anti-LAG3 antibody or an antigen binding fragment thereof an anti-VISTA antibody or an antigen binding fragment thereof an anti-TIGIT antibody or an antigen binding fragment thereof an anti-TIM3 antibody or an antigen binding fragment thereof an anti-HVEM antibody or an antigen binding fragment thereof an anti-CD27 antibody or an antigen binding fragment thereof an anti-CD137 antibody or an antigen binding fragment thereof an anti-OX40 antibody or an antigen binding fragment thereof; an anti-CD28 antibody or an antigen binding fragment thereof an anti-PDL1 antibody or an antigen binding fragment thereof; an anti-PDL2 antibody or an antigen binding fragment thereof an anti-GITR antibody or an antigen binding fragment thereof an anti-ICOS antibody or an antigen binding fragment thereof an anti-SIRPa antibody or an antigen binding fragment thereof; an anti-ILT2 antibody or an antigen binding fragment thereof an anti-ILT3 antibody or an antigen binding fragment thereof; an anti-ILT4 antibody or an antigen binding fragment thereof an anti-ILT5 antibody or an antigen binding fragment thereof an anti-CD73 antibody or an antigen binding fragment thereof and an anti-CD47 antibody or an antigen binding fragment thereof. In one embodiment, the anti-PD1 antibody or an antigen binding fragment thereof is selected from the group consisting of: pembrolizumab or an antigen binding fragment thereof and nivolumab or an antigen binding fragment thereof.

The invention also comprises a vaccine comprising an antibody or antigen binding fragment of the invention and an antigen.

The invention also comprises a method for detecting the presence of a CTLA4 peptide or a fragment thereof in a sample comprising contacting the sample with an antibody or antigen binding fragment of the invention and detecting the presence of a complex between the antibody or fragment and the peptide; wherein detection of the complex indicates the presence of the CTLA4 peptide.

The invention also comprises a method of increasing the activity of an immune cell, comprising contacting the immune cell with any one of the antibodies or antigen binding fragments of the invention.

In one embodiment, the invention comprises a method of increasing the activity of an immune cell, comprising administering to a subject in need thereof an effective amount of an antibody or antigen binding fragment of the invention. In one embodiment, said method is used for: the treatment of cancer; the treatment of an infection or infectious disease; or as a vaccine adjuvant.

In one embodiment, the invention comprises the use of an antibody or antigen binding fragment of the invention for the preparation of a medicament to: increase immune cell activation; treat cancer; or treat an infection or infectious disease.

In one embodiment, the invention comprises the use of an antibody or antigen binding fragment of the invention for the manufacture of a medicament for the treatment of cancer for: increasing immune cell activation; treating cancer; or treating an infection or infectious disease.

A further aspect of the present invention relates to use of the antibody or antigen binding fragment thereof according to any one of the embodiments of the present invention in the preparation of a kit for use in detecting the presence or level of CTLA4 in a sample.

A further aspect of the present invention relates to use of the antibody or antigen binding fragment thereof according to any one of the embodiments of the present invention or the conjugate according to the present invention in the preparation of a medicament for use in the prevention and/or treatment and/or adjuvant therapy and/or diagnosis of a tumor, cancer, anemia, infection or infectious diseases.

A further aspect of the present invention relates to use of the antibody or antigen binding fragment thereof according to any one of the embodiments of the present invention or the conjugate according to the present invention in the preparation of an agent that:
  detects the level of CTLA4 in a sample,
  blocks the binding of CTLA4 to B7,
  regulates (e.g., down-regulates) the activity of CTLA4 or the level of CTLA4,
  relieves the immunosuppression on the body by CTLA4,
  activates T lymphocytes,
  increases the expression of IL-2 in T lymphocytes;
  increases the expression of IFN-γ in T lymphocytes; and/or
  cross-reacts with cyno CTLA4.

A further aspect of the present invention relates to an in vivo or in vitro method comprising the step of administrating to cells an effective amount of the antibody or antigen binding fragment thereof according to any one of the embodiments of the present invention or the conjugate according to the present invention, wherein the method is selected from the following:
  a method of detecting the level of CTLA4 in a sample,
  a method of blocking the binding of CTLA4 to B7,
  a method of regulating (e.g., down-regulating) the activity of CTLA4 or the level of CTLA4,
  a method of relieving the immunosuppression on the body by CTLA4,
  a method of activating T lymphocytes,
  a method of increasing the expression of IL-2 in T lymphocytes; and/or
  a method of increasing the expression of IFN-γ in T lymphocytes.

A further aspect of the present invention relates to a method of the prevention and/or treatment and/or adjuvant therapy and/or diagnosis of a tumor or cancer, comprising administrating to a subject an effective amount of the antibody or antigen binding fragment thereof according to any one of the embodiments of the present invention or the conjugate according to the present invention.

The antibody or antigen binding fragment thereof according to any one of the embodiments of the present invention for use in the prevention and/or treatment and/or adjuvant therapy and/or diagnosis of a tumor or cancer.

The antibody or antigen binding fragment thereof according to any one of the embodiments of the present invention for use in:
  blocking the binding of CTLA4 to B7,
  regulating (e.g., down-regulating) the activity of CTLA4 or the level of CTLA4,
  relieving the immunosuppression on the body by CTLA4,
  activating T lymphocytes,
  increasing the expression of IL-2 in T lymphocytes; and/or
  increasing the expression of IFN-γ in T lymphocytes.

DETAILED DESCRIPTION

Figure 1:
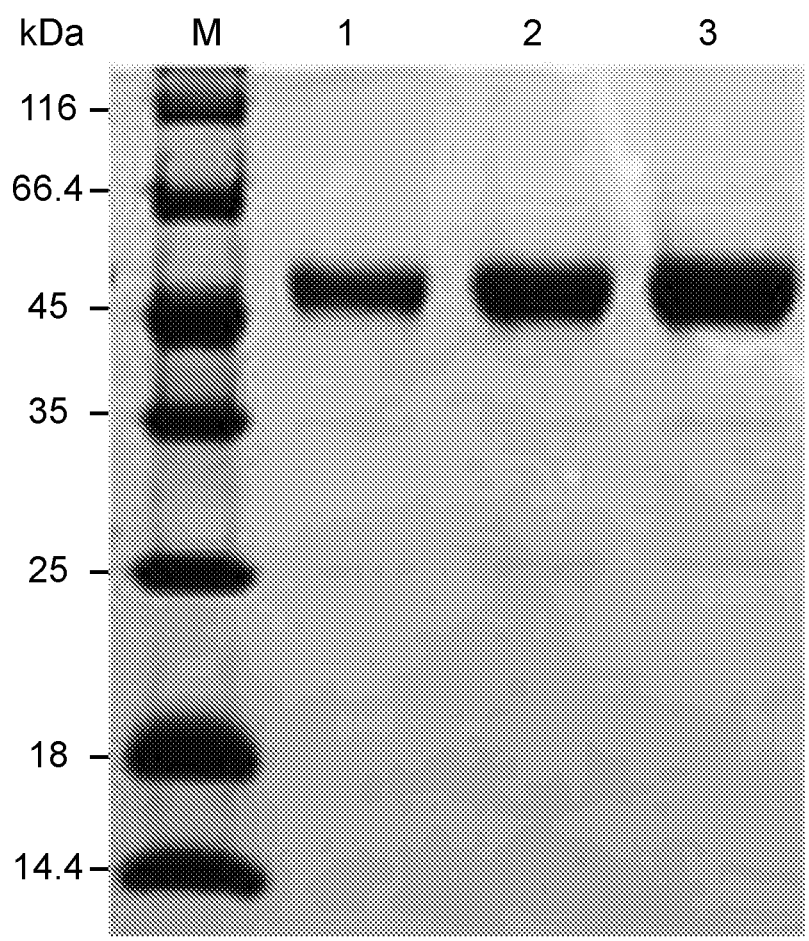
FIG. 1 shows results of SDS-PAGE of the CTLA4-mFc fusion protein. The samples and loading amounts in the 4 lanes, from left to right were: Marker, 10 μL; CTLA4-mFc fusion protein, 1 μg; CTLA4-mFc fusion protein, 2 μg; CTLA4-mFc fusion protein, 3 μg.

Unless stated otherwise, scientific and technical terms used herein have the same meaning as commonly understood by those skilled in the art. Moreover, procedures of cell culture, molecular genetics, nucleic acid chemistry, immunology used herein are the widely utilized methodologies in the relevant art. For purpose of better understanding the present invention, the definitions and explanations of relevant terms are provided below.

As used herein, when reference is made to the amino acid sequence of the CTLA4 protein (CytotoxicT-Lymphocyte-Antigen4), it includes the full length of the CTLA4 protein, or the extracellular fragment of CTLA4, CTLA4ECD (the portion of SEQ ID NO: 1 underlined with a wavy line), or a fragment comprising CTLA4ECD; it also includes a fusion protein of CTLA4ECD, e.g., the CTLA4ECD fragment fused to the Fc protein fragment of a mouse or human IgG (mFc or hFc) (see the description in Example 1). However, as understood by those skilled in the art, a mutation or variation (including, and not limited to, substitution, deletion and/or addition) may be naturally produced in or artificially introduced into the amino acid sequence of the CTLA4 protein, without affecting its biological functions. Therefore, in the present invention, the term "CTLA4 protein" should include all such sequences, including the sequence of the portion of SEQ ID NO: 1 underlined with a wavy line, as well as its native or artificial variants. Furthermore, when reference is made to a sequence fragment of the CTLA4 protein, it not only includes a sequence fragment of the portion of SEQ ID NO: 1 underlined with a wavy line, but also includes the corresponding sequence fragments of its native or artificial variants.

As used herein, unless specifically stated, said B7 refers to B7-1 and/or B7-2; and their specific proteins sequences refer to the sequences known in the art. Reference can be made to the sequences disclosed in the literatures of the prior art or GenBank, e.g., B7-1 (CD80, NCBI Gene ID: 941), B7-2 (CD86, NCBI Gene ID: 942).

As used herein, the term $EC_{50}$ refers to concentration for 50% of maximal effect, i.e., the concentration causing 50% of the maximal effect.

As used herein, the term "antibody" refers to an immunoglobulin molecule which generally consists of two pairs of polypeptide chains (each pair has a "light" (L) chain and a "heavy" (H) chain). Antibody light chains can be classified as κ and λ light chain. Heavy chains can be classified as μ, δ, γ, α or ε, and the isotype of antibody is defined as IgM, IgD, IgG, IgA and IgE, respectively. Within a light chain and heavy chain, a variable region and a constant region are joined via a "J" region of about 12 or more amino acids, and heavy chain further comprises a "D" region of about 3 or more amino acids. Each heavy chain consists of a heavy chain variable region ($V_H$) and a heavy chain constant region ($C_H$). The heavy chain constant region consists of 3 domains ($C_H1$, $C_H2$ and $C_H3$). Each light chain consists of a light chain variable region ($V_L$) and a light chain constant region($C_L$). The light chain constant region consists of a $C_L$ domain. The constant region of antibody can mediate the binding of the immunoglobulin to host tissues or factors, including various cells of the immune system (e.g., effector cells) and the first component of the classical complement system (C1q). $V_H$ and $V_L$ regions can further be subdivided into regions having high variability (referred to as complementarity determining region (CDR)), interspersed with regions called framework regions (FR) which are relatively conserved. Each $V_H$ or $V_L$ consists of 3CDRs and 4FRs, arranged by the following order from the amino terminal to the carboxy terminal: FR1, CDR1, FR2, CDR2, FR3, CDR3, and FR4. The variable regions ($V_H$ and $V_L$) of each pair of heavy chain/light chain form an antigen binding site, respectively. The assignment of amino acids to each region or domain follows the definition provided in Kabat, Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. The term "antibody" is not limited by any specific method for producing the antibody. For example, it includes, particularly, recombinant antibodies, monoclonal antibodies and polyclonal antibodies. Antibodies can be antibodies of different isotypes, e.g., IgG (e.g., IgG1, IgG2, IgG3 or IgG4 subtype), IgA1, IgA2, IgD, IgE or IgM antibodies.

As used herein, the term "antigen binding fragment" of antibody refers to a polypeptide comprising a fragment of a full length antibody, which retains the ability to specifically bind to the antigen bound by the full length antibody, and/or to compete with the full length antibody for specifically binding to the antigen. It is also referred to as "antigen binding portion". Generally, see Fundamental Immunology, Ch. 7 (Paul, W., ed., Second Edition, Raven Press, N.Y. (1989)), which is incorporated herein by reference in the entirety for all purposes. Antigen binding fragments of antibodies can be produced by recombinant DNA technique or enzymatic or chemical cleavage of intact antibodies. In some cases, antigen binding fragments include Fab, Fab', F(ab')$_2$, Fd, Fv, dAb and complementarity determining region (CDR) fragment, single chain antibody (e.g., scFv), chimeric antibody, diabody and such polypeptides which comprises at least a portion of the antibody sufficient to confer the ability of specific antigen binding to the polypeptide.

As used herein, the term "Fd fragment" refers to an antibody fragment consisting of the $V_H$ and $C_H1$ domains; the term "Fv fragment" refers to an antibody fragment consisting of the $V_L$ and $V_H$ domains of a single arm of antibody; the term "dAb fragment" refers to an antibody fragment consisting of the $V_H$ domain (Ward et al., Nature 341:544-546 (1989)); the term "Fab fragment" refers to an antibody fragment consisting of the $V_L$, $V_H$, $C_L$ and $C_H1$ domains; and the term "F(ab')$_2$ fragment" refers to an antibody fragment comprising two Fab fragments connected by disulfide bridges on the hinge region.

In some cases, the antigen binding fragment of antibody is a single chain antibody (e.g., scFv), wherein the $V_L$ and $V_H$ domains pair to each other via a linker which enables production of a single polypeptide chain to form a monovalent molecule (see, e.g., Bird et al., Science 242:423-426 (1988) and Huston et al., Proc. Natl. Acad. Sci. USA 85:5879-5883 (1988)). Such scFv molecule can have the general structure: NH$_2$—V$_L$-Linker-V$_H$-COOH or NH$_2$—V$_H$-Linker-V$_L$-COOH. Suitable linkers from the prior art consist of the repeated GGGGS amino acid sequence or its variants. For example, a linker having the amino acid sequence (GGGGS)$_4$ can be used, but its variants can also be used (Holliger et al. (1993)Proc. Natl. Acad. Sci. USA 90: 6444-6448). Other linkers useful in the present invention are described in Alfthan et al. (1995) *Protein Eng.* 8:725-731; Choi et al. (2001) *Eur. J. Immunol.* 31: 94-106; Hu et al. (1996) *Cancer Res.* 56:3055-3061; Kipriyanov et al. (1999) *J. Mol. Biol.* 293:41-56 and Roovers et al. (2001) *Cancer Immunol.*

In some cases, the antigen binding fragment of antibody is a diabody (a bivalent antibody), wherein the $V_H$ and $V_L$ domains are expressed on a single polypeptide chain. However, the linker exploited is too short that the two domains on the same chain cannot pair with each other, and are forced to pair with the complemental domain on another chain. By this way, two antigen binding sites are formed (see, e.g., Holliger P. et al., *Proc. Natl. Acad. Sci.* USA 90:6444-6448 (1993) and Poljak R. J. et al., *Structure* 2:1121-1123 (1994)).

Antigen binding fragments of antibodies (e.g., the above antibody fragments) can be obtained form given antibodies using conventional technologies which are known to those skilled in the art (e.g., recombinant DNA technique or enzymatic or chemical cleavage method), and can be screened for specificity in the same as that of intact antibodies.

Herein, unless explicitly indicated in the context, when reference is made to the term "antibody", it not only includes intact antibodies, but also includes antigen binding fragments of antibodies.

As used herein, the terms "mAb" or "monoclonal antibody" refers to an antibody or antibody fragment from a population of highly homogenous antibody molecules, i.e., the individual antibodies comprising the population are identical except for possible naturally occurring mutations. Monoclonal antibodies are highly specific to a single epitope on the antigen. In contrast to monoclonal antibodies, polyclonal antibody preparations typically include at least two or more different antibodies recognizing different epitopes on the antigen. Monoclonal antibodies can generally be obtained using the hybridoma technique first described by Kohler et al. (Nature, 256:495,1975), or can be obtained using the recombinant DNA technique (see U.S. Pat. No. 4,816,567, for example).

As used herein, the term "chimeric" antibodies refer to such antibodies, in which a portion of the light chain or/and heavy chain is derived from an antibody (which can be derived from a particular species or belonging to a particular antibody class or subclass), while another portion of the light chain or/and heavy chain is derived from another antibody (which can be derived from an identical or different species or belonging to an identical or different antibody class or subclass), as long as they retain the activity to bind to the target antigen (U.S. Pat. No. 4,816,567 awarded to Cabilly et al.; Morrison et al., Proc. Natl. Acad. Sci. USA, 81:6851-6855 (1984)).

As used herein, the term "humanized" antibodies refer to the antibodies or antibody fragments obtained after replacing all or some CDRs of a human immunoglobulin (recipient antibody) with CDRs of a non-human antibody (donor antibody), wherein the donor antibody can be a non-human (e.g., mouse, rat or rabbit) antibody having the desired specificity, affinity or reactivity. Furthermore, some amino acid residues of the framework regions (FRs) of the recipient antibody can be replaced with corresponding amino acid residues of the non-human antibody or amino acid residues of other antibodies so as to further improve or optimize the performance of the antibody. For more details about humanized antibodies, see, e.g., Jones et al., *Nature,* 321:522-525 (1986); Reichmann et al., *Nature,* 332:323-329 (1988); Presta, *Curr. Op. Struct. Biol.,* 2:593-596 (1992); and Clark, *Immunol. Today* 21: 397-402 (2000).

As used herein, the term "epitope" refers to the part on an antigen specifically bound by an immunoglobulin or antibody. In the art, "epitope" is also called "antigenic determinant".

An epitope or antigenic determinant generally consists of the active surface groups of the molecule, e.g., amino acid or carbohydrate compounds or sugar side chains, and generally has specific three-dimensional structural characteristics and specific charge characteristics. For example, an epitope generally comprises at least 3, 4, 5, 6, 7, 8, 9, 10, 11, 12, 13, 14 or 15 consecutive or inconsecutive amino acids in a distance spatial conformation. It can be a "linear" or "conformational" epitope. See, e.g., Epitope Mapping Protocols in Methods in Molecular Biology, Vol. 66, G. E. Morris, Ed. (1996). In a linear epitope, all the points of the interaction between the protein and the interacting molecule (e.g., antibody) are present along the primary amino acid sequence of the protein in a line. In a conformational epitope, the interacting points are present as spanning the amino acid residues of the protein which are separate from each other.

The present invention includes isolated anti-CTLA4 antibodies and antigen-binding fragments thereof and methods of use thereof "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

As used herein, the term "*E. coli* expression system" refers to an expression system consisting of *E. coli* (strain) and vector, wherein *E. coli* (strain) is derived from strains commercially available, e.g., but not limited to GI698, ER2566, BL21(DE3), B834(DE3), and BLR(DE3).

As used herein, the term "vector" refers to a nucleic acid carrying tool into which a polynucleotide can be inserted. When a vector enables the expression of the protein encoded by the inserted polynucleotide, the vector is called expression vector. A vector can be introduced into a host cell by transformation, transduction or transfection, such that the genetic substance component carried by the vector is expressed in the host cell. Vectors are well known to those skilled in the art, including, but not limited to: plasmid; phagemid; cosmid; artificial chromosome, e.g., yeast artificial chromosome (YAC), bacterial artificial chromosome (BAC) or P1-derived artificial chromosome (PAC); bacteriophage, e.g., λ phage or M13 phage as well as animal virus and the like. Animal viruses which can be used as a vector, include, but not limited to, retrovirus (including lentivirus), adenovirus, adeno-associated virus, herpes virus (e.g., herpes simplex virus), poxvirus, baculovirus, papilloma virus, papova virus (e.g., SV40). A vector can comprise several components for controlling the expression, including, but not limited to, promoter sequence, transcription initiation sequence, enhancer sequence, selection component and reporter gene. Moreover, a vector can also comprise a replication initiation site.

As used herein, the term "host cell" refers to cells which can be used for introduction of a vector, including, but not limited to, prokaryotic cells such as *E. coli* or *Bacillus subtilis*, fungal cells such as yeast cells or *Aspergillus*, insect cells such as S2 *Drosophila* cell or Sf9, or animal cells such as fibroblast, CHOcell, COScell, NSOcell, HeLacell, BHKcell, HEK 293cell or human cell.

As used herein, the term "identity" is used to describe the sequence matching between two polypeptides or between two nucleic acids. When the corresponding positions in two sequences compared are occupied by the same base or amino acid monomer subunit (for example, the corresponding positions in two DNA molecules are both occupied by adenine, or the corresponding positions in two polypeptides are both occupied by lysine), the molecules are identical at that position. The "percent identity" between two sequences is a function of the number of the matching positions shared by these two sequences divided by the number of the positions compared ×100. For example, if 6 among 10 positions of two sequences match, these two sequences have 60% identity. For example, DNA sequences CTGACT and CAGGTT share 50% identity (3 among 6 positions match in total). Generally, two sequences are compared after alignment to generate maximal identity. For example, such alignment can be conveniently achieved using a computer program, e.g., the Align program (DNAstar, Inc.), by the method of Needleman et al. (1970) *J Mol. Biol.* 48: 443-453. Furthermore, the algorithm of E. Meyers and W. Miller (Comput. Appl Biosci., 4:11-17 (1988)) incorporated into the ALIGN program (version 2.0) can be used to determine the percent identity between two amino acid sequences, using the PAM120 weight residue table, a Gap length penalty of 12 and a gap penalty of 4. Moreover, the algorithm of Needleman and Wunsch (J Mol Biol. 48:444-453 (1970)) incorporated into the GAP program of the GCG package (available at www.gcg.com) can be used to determine the percent identity between two amino acid sequences, using the Blossum 62 matrix or PAM250 matrix, a gap weight of 16, 14, 12, 10, 8, 6 or 4 and a length weight of 1, 2, 3, 4, 5 or 6.

As used herein, the term "specific binding" refers to the non-random binding reaction between two molecules, such as the reaction between an antibody and its targeted antigen. In some embodiments, an antibody specifically binding an antigen (or an antibody specific for an antigen) means the antibody binds the antigen at an affinity ($K_D$) less than about $10^{-5}$ M, e.g., less than about $10^{-6}$ M, $10^{-7}$ M, $10^{-8}$ M, $10^{-9}$ M or $10^{-10}$ M or less.

As used herein, the term "$K_D$" refers to the dissociation equilibration of a particular antibody-antigen interaction, which is used to describe the binding affinity between the antibody and the antigen. The less the equilibration dissociation constant is, the closer the antibody-antigen binding is and the higher the affinity between the antibody and antigen. Generally, an antibody binds the antigen at a dissociation equilibration constant ($K_D$) less than about $10^{-5}$ M, e.g., less than about $10^{-6}$ M, $10^{-7}$ M, $10^{-8}$ M, $10^{-9}$ M or $10^{-10}$ M or less, e.g., as determined using surface plasmon resonance (SPR) on a BIACORE instrument or a similar technique (e.g. OCTET or KINEXA).

As used herein, the terms "monoclonal antibody" and "mAb" have the same meaning, and can be used interchangeably. Also, the terms "polyclonal antibody" and "pub" have the same meaning, and can be used interchangeably. Again, the terms "polypeptide" and "protein" have the same meaning, and can be used interchangeably. Furthermore, in the present invention, amino acids are generally represented by single-letter or three-letter abbreviations well known in the art. For example, alanine can be represented by A or Ala.

As used herein, the terms "hybridoma" and "hybridoma cell line" can be used interchangeably. Moreover, when reference is made to the term "hybridoma" or "hybridoma cell line", it also comprises the subclonal and descendent cells of the hybridoma. For example, when reference is made to the hybridoma cell line LT002 or LT003, it also comprises the subclonal and descendent cells of the hybridoma cell line LT002 or LT003.

As used herein, the term "pharmaceutically acceptable carrier and/or excipient" refers to vector and/or excipient compatible to the subject and the active component in pharmacology and/or physiology, which are well known in the art (see, e.g., Remington's Pharmaceutical Sciences. Edited by Gennaro A R, 19th ed. Pennsylvania: Mack Publishing Company, 1995), and include but not limited to: pH adjusting agent, surfactant, adjuvant, ionic intensity enhancer. For example, pH adjusting agent includes but not limited to phosphate buffer; surfactant includes but not limited to cationic, anionic or nonionic surfactant, e.g., Tween-80; and ionic intensity enhancer includes but not limited to sodium chloride.

As used herein, the term "adjuvant" refers to non-specific immune enhancer, which can enhance the immune response of the body to the antigen or change the type of the immune response when delivered together with an antigen or in advance into the body. There are many adjuvants, including but not limited to aluminum adjuvant (e.g., aluminum hydroxide), Freund's adjuvant (e.g., complete Freund's adjuvant and incomplete Freund's adjuvant), *Corynebacterium parvum*, lipopolysaccharide, cytokine, and the like. Freund's adjuvant is the most commonly used one in animal experiments at present, and aluminum hydroxide is the widely used one in clinical trials.

As used herein, the term "effective amount" refers to an amount sufficient to achieve or at least partially achieve the desired effects. For example, prophylactically effective amount for a disease (e.g., a disease or tumor associated with excessive binding of CTLA4 to B7 or CTLA4 activity) refers to an amount sufficient to prevent, arrest, or delay the development of a disease (e.g., a disease or tumor associated with excessive binding of CTLA4 to B7 or CTLA4 activity); and therapeutically effective amount for a disease refers to an amount sufficient to cure or at least partially arrest a disease and its complications in a patient suffering from the disease. It is well within the skills of those skilled in the art to determine such effective amount. For example, a therapeutically effective amount will depend on the severity of the disease to be treated, the general status of the immune system of the patient, the general status of the patient, e.g., age, body weight and sex, administration mode of the agent, other therapies administered simultaneously, and the like.

As used herein, including the appended claims, the singular forms of words such as "a," "an," and "the", include their corresponding plural references unless the context clearly dictates otherwise.

"Administration" as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

Antibodies of the Invention

Therapeutic antibodies, especially monoclonal antibodies (MAB) have achieved excellent efficacy in the treatment of several diseases. The traditional method to obtain such therapeutic antibody is immunizing an animal with an antigen, obtaining antibodies against the antigen from the immunized animal, optionally, improving an antibody having low affinity to the antigen by affinity maturation. However, such method is time consuming and labor consuming, and often fails to target a specific epitope on the antigen.

Antigen binding is dependent on the variable regions of the light chain and heavy chain; the variable region of each chain comprises three hypervariable regions, also called complementarity determining region (CDR) (the heavy chain (H) comprises HCDR1, HCDR2 and HCDR3, and the light chain (L) comprises LCDR1, LCDR2 and LCDR3; for definition, see Kabat et al., Sequences of Proteins of Immunological Interest, Fifth Edition (1991), Vol. 1-3, NIH Publication 91-3242, Bethesda Md.).

The invention relates in part to anti-CTLA4 antibodies having the sequences described herein. The antibodies of the invention can specifically bind to CTLA4. They can block the binding of CLTA4 to B7, specifically relieve the immunosuppression on the body by CTLA4, and activate T lymphocytes very effectively.

In particular, the invention relates to the mouse antibody described herein as 4G10, comprising the heavy chain variable region (VH) of SEQ ID NO:4 and the light chain variable region (VL) of SEQ ID NO:6; and humanized versions of this antibody.

In some embodiments, the humanized VH sequences of the 4G10 antibody can comprise any one of the following VH regions:
 4G10H1 (SEQ ID NO:8)
 4G10H3 (SEQ ID NO:12)
 4G10H4 (SEQ ID NO:16)
 4G10H5 (SEQ ID NO:18)
 4G10 H consensus (SEQ ID NO:19).

In some embodiments, the humanized VH sequence of the 4G10 antibody can comprise the following CDR regions (determined according to Kabat):
 HCDR1: SEQ ID NO: 21,
 HCDR2: SEQ ID NO: 22,
 HCDR3: SEQ ID NO: 23, In alternative embodiments, the humanized VH sequence of the 4G10 antibody can comprise the following CDR regions (determined by VBASE2 database analysis):
 HCDR1: SEQ ID NO: 27,
 HCDR2: SEQ ID NO: 28
 HCDR3: SEQ ID NO: 29.

In some embodiments, the humanized VL sequences of the 4G10 antibody can comprise any one of the following VL regions:
 4G10L1 (SEQ ID NO: 10)
 4G10L3 (SEQ ID NO: 14)
 4G10 L consensus (SEQ ID NO: 20).

In some embodiments, the humanized VL sequence of the 4G10 antibody can comprise the following CDR regions (which CDR regions were determined according to Kabat):
 LCDR1: SEQ ID NO: 24,
 LCDR2: SEQ ID NO: 25,
 LCDR3: SEQ ID NO: 26, In alternative embodiments, the humanized VL sequence of the 4G10 antibody can comprise the following CDR regions (which CDR regions were determined according to VBASE database analysis):
 LCDR1: SEQ ID NO: 30,
 LCDR2: SEQ ID NO: 31,
 LCDR3: SEQ ID NO: 32.

Any of the above described humanized VH regions could be paired with any of the above described humanized VL regions. In preferred embodiments, the invention comprises an antibody comprising the VH region of SEQ ID NO: 19 and the VL region of SEQ ID NO: 20. In preferred embodiments, the invention comprises an antibody comprising the VH region of SEQ ID NO: 8 and the VL region of SEQ ID NO: 10. In preferred embodiments, the invention comprises an antibody comprising the VH region of SEQ ID NO: 12 and the VL region of SEQ ID NO: 14. In preferred embodiments, the invention comprises an antibody comprising the VH region of SEQ ID NO: 16 and the VL region of SEQ ID NO: 14. In preferred embodiments, the invention comprises an antibody comprising the VH region of SEQ ID NO: 18 and the VL region of SEQ ID NO: 14.

Antibody Expression

The antibodies and antibody fragments of the invention can be made using any method known to a person of skill in the art. The antibodies or antibody fragments of the invention can be made in any host cell. Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermo-* tolerans, Pichia salictaria, Pichia guercuum, Pichia ptjperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens and Neurospora crassa. Pichia sp., any Saccharomyces sp., Hansenula polymorpha, any Kluyveromyces sp., Candida albicans, any Aspergillus sp., Trichoderma reesei, Chrysosporium lucknowense, any Fusarium sp., Yarrowia lipolytica, and Neurospora crassa. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody or fragment or chain in the host cells or secretion of the same into the culture medium in which the host cells are grown.

Antibody Purification

Antibodies and antigen-binding fragments thereof and immunoglobulin chains can be recovered from the culture medium using standard protein purification methods. Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an antibody or antigen-binding fragment thereof of the present invention comprising introducing a sample comprising the antibody or fragment to a purification medium (e.g., cation exchange medium, anion exchange medium, hydrophobic exchange medium, affinity purification medium (e.g., protein-A, protein-G, protein-A/G, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium.

Antibody Engineering

In certain embodiments, the antibodies and antigen-binding fragments thereof of the invention are engineered to include modifications to in the framework and/or CDRs to improve their properties. Such engineered changes can be based on molecular modeling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) *Sequences of Proteins of Immunological Interest*, Kabat, et al.; National Institutes of Health, Bethesda, Md.; 5th ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J. Mol. Biol.* 196:901-917 or Chothia, et al., (1989) *Nature* 342:878-883. There are variations between regions classified as "CDRs" and "hypervariable loops". Later studies (Raghunathan et al, (2012) J Mol Recog. 25, 3, 103-113) analyzed several antibody—antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice, the potential antigen binding regions based on model differ from the conventional "CDR"s or "hyper variable" loops. Commercial scientific software such as MOE (Chemical Computing Group) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for CTLA4, or other desired biological activity to unacceptable levels.

Exemplary Stabilizing CDR Variants

| CDR Residue | Stabilizing Variant Sequence |
| --- | --- |
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

Antibody Engineering of the Fc Region

The antibodies (e.g., humanized antibodies) and antigen-binding fragments thereof disclosed herein can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein can be chemically modified (e.g., one or more chemical moieties can be attached to the antibody) or be modified to alter its glycosylation, again to alter one or more properties of the antibody or fragment.

Antibody Conjugates

The present invention also comprises antibody cojugates comprising the antibodies or antigen binding fragments of the invention. The antibodies of the invention may be conjugated to a chemical moiety. The chemical moiety may be, inter alia, a polymer, a radionucleotide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxy-polyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein may also be conjugated with labels such as $^{99}Tc$, $^{90}Y$, $^{111}In$, $^{32}F$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antibodies and antigen-binding fragments disclosed herein may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies and fragments are conventional and well known in the art.

Therapeutic Uses of Anti-CTLA4 Antibodies

Further provided are methods for treating subjects, including human subjects, in need of treatment with the isolated antibodies or antigen-binding fragments thereof disclosed herein. In one embodiment of the invention, such subject suffers from an infection or an infectious disease. In another embodiment of the invention, such subject suffers from cancer. In one embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating subjects using an antibody or antigen-binding fragment thereof of the invention wherein the subject suffers from a viral infection. In one embodiment, the viral infection is infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an antibody or antigen-binding fragment thereof of the invention, wherein the subject suffers from a bacterial infection. In one embodiment, the bacterial infection is an infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using an antibody or antigen-binding fragment thereof of the invention, wherein the subject suffers from a fungal infection. In one embodiment, the fungal infection is an infection with a fungus selected from the group consisting of *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitides, Paracoccidioides brasiliensis, Coccidioides immitis* and *Histoplasma capsulatum*.

In an embodiment, the invention provides methods for treating subjects using an anti-CTLA4 antibody or antigen-binding fragment thereof of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia micron, Trypanosoma brucei, Trypanosoma cruzi, Leishmania donovani, Toxoplasma gondii* and *Nippostrongylus brasiliensis*.

A "subject" may be a mammal such as a human, dog, cat, horse, cow, mouse, rat, monkey (e.g., cynomolgus monkey, e.g., *Macaca fascicularis*) or rabbit. In preferred embodiments of the invention, the subject is a human subject.

In particular embodiments, the antibodies or antigen-binding fragments thereof disclosed herein may be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also part of the present invention.

In particular embodiments, the antibodies or antigen-binding fragments thereof disclosed herein may be used alone, or in association with tumor vaccines.

In particular embodiments, the antibodies or antigen-binding fragments thereof disclosed herein may be used alone, or in association with chemotherapeutic agents.

In particular embodiments, the antibodies or antigen-binding fragments thereof disclosed herein may be used alone, or in association with radiation therapy.

In particular embodiments, the antibodies or antigen-binding fragments thereof disclosed herein may be used alone, or in association with targeted therapies. Examples of targeted therapies include: hormone therapies, signal transduction inhibitors (e.g., EGFR inhibitors, such as cetuximab (Erbitux) and erlotinib (Tarceva)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators, apoptosis inducers (e.g., bortezomib (Velcade) and carfilzomib (Kyprolis)), angiogenesis inhibitors (e.g., bevacizumab (Avastin) and ramucirumab (Cyramza), monoclonal antibodies attached to toxins (e.g., brentuximab vedotin (Adcetris) and ado-trastuzumab emtansine (Kadcyla)).

In particular embodiments, the antibodies or antigen-binding fragments thereof of the invention may be used in combination with an anti-cancer therapeutic agent or immunomodulatory drug such as an immunomodulatory receptor inhibitor, e.g., an antibody or antigen-binding fragment thereof that specifically binds to the receptor.

Thus, the present invention includes compositions comprising an antibody or antigen-binding fragment thereof of the present invention (in association with pembrolizumab; as well as methods for treating or preventing cancer in a subject comprising administering an effective amount of the anti-CTLA4 antibody of the invention, or antigen-binding fragment thereof, and pembrolizumab to the subject. Optionally, the subject is also administered a further therapeutic agent.

In an embodiment of the invention, an antibody or antigen-binding fragment thereof of the invention is in association with one or more of: anti-PD1 antibody (e.g., pembrolizumab, nivolumab, pidilizumab (CT-011)), anti-PDL1 antibody, anti-CTLA4 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD-L1 antibody (e.g., BMS-936559, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-SIRPa, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, IL-10 or PEGylated IL-10, or any small organic molecule inhibitor of such targets.

In an embodiment of the invention, an antibody or antigen-binding fragment thereof of the invention is in association with an anti-PD1 antibody.

In an embodiment of the invention, an antibody or antigen-binding fragment thereof of the invention is in association with an anti-PDL1 antibody (e.g., BMS-936559, MSB0010718C or MPDL3280A).

In an embodiment of the invention, an antibody or antigen-binding fragment thereof of the invention is in association with an anti-TIGIT antibody.

In an embodiment of the invention, antibody or antigen-binding fragment thereof of the invention is in association with an anti-CS1 antibody.

In an embodiment of the invention, an antibody or antigen-binding fragment thereof of the invention is in association with an anti-KIR2DL1/2/3 antibody.

In an embodiment of the invention, an antibody or antigen-binding fragment thereof of the invention is in association with an anti-CD137 (e.g., urelumab) antibody.

In an embodiment of the invention, an antibody or antigen-binding fragment thereof of the invention is in association with an anti-GITR (e.g., TRX518) antibody.

In an embodiment of the invention, an antibody or antigen-binding fragment thereof of the invention is in association with an anti-PD-L2 antibody.

In an embodiment of the invention, an antibody or antigen-binding fragment thereof of the invention is in association with an anti-ITL1 antibody.

In an embodiment of the invention, an antibody or antigen-binding fragment thereof of the invention is in association with an anti-ITL2 antibody.

In an embodiment of the invention, an antibody or antigen-binding fragment thereof of the invention is in association with an anti-ITL3 antibody.

In an embodiment of the invention, an antibody or antigen-binding fragment thereof of the invention is in association with an anti-ITL4 antibody.

In an embodiment of the invention, an antibody or antigen-binding fragment thereof of the invention is in association with an anti-ITL5 antibody.

In an embodiment of the invention, an antibody or antigen-binding fragment thereof of the invention is in association with an anti-ITL6 antibody.

In an embodiment of the invention, an antibody or antigen-binding fragment thereof of the invention is in association with an anti-ITL7 antibody.

In an embodiment of the invention, an antibody or antigen-binding fragment thereof of the invention is in association with an anti-ITL8 antibody.

In an embodiment of the invention, an antibody or antigen-binding fragment thereof of the invention is in association with an anti-CD40 antibody.

In an embodiment of the invention, an antibody or antigen-binding fragment thereof of the invention is in association with an anti-OX40 antibody.

In an embodiment of the invention, an antibody or antigen-binding fragment thereof of the invention is in association with an anti-KIR2DL1 antibody.

In an embodiment of the invention, an antibody or antigen-binding fragment thereof of the invention is in association with an anti-KIR2DL2/3 antibody.

In an embodiment of the invention, an antibody or antigen-binding fragment thereof of the invention is in association with an anti-KIR2DL4 antibody.

In an embodiment of the invention, an antibody or antigen-binding fragment thereof of the invention is in association with an anti-KIR2DL5A antibody.

In an embodiment of the invention, an antibody or antigen-binding fragment thereof of the invention is in association with an anti-KIR2DL5B antibody.

In an embodiment of the invention, an antibody or antigen-binding fragment thereof of the invention is in association with an anti-KIR3DL1 antibody.

In an embodiment of the invention, an antibody or antigen-binding fragment thereof of the invention is in association with an anti-KIR3DL2 antibody.

In an embodiment of the invention, an antibody or antigen-binding fragment thereof of the invention is in association with an anti-KIR3DL3 antibody.

In an embodiment of the invention, an antibody or antigen-binding fragment thereof of the invention is in association with an anti-NKG2A antibody.

In an embodiment of the invention, an antibody or antigen-binding fragment thereof of the invention is in association with an anti-NKG2C antibody.

In an embodiment of the invention, an antibody or antigen-binding fragment thereof of the invention is in association with an anti-ICOS antibody.

In an embodiment of the invention, an antibody or antigen-binding fragment thereof of the invention is in association with an anti-SIRPα antibody.

In an embodiment of the invention, an antibody or antigen-binding fragment thereof of the invention is in association with an anti-4-1BB antibody.

In an embodiment of the invention, an antibody or antigen-binding fragment thereof of the invention is in association with an anti-IL-10 antibody.

In an embodiment of the invention, an antibody or antigen-binding fragment thereof of the invention is in association with an anti-TSLP antibody.

In an embodiment of the invention, an antibody or antigen-binding fragment thereof of the invention is in association with IL-10 or PEGylated IL-10.

In an embodiment of the invention, an antibody or antigen-binding fragment thereof of the invention is in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, an antibody or antigen-binding fragment thereof of the invention is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, *Bacillus* Calmette-Guerin (BCG) vaccine, batabulin, BC-210, besodotox, bevacizumab, bicalutamide, Bio111, BIO140, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, Cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD121974, endostatin, enzalutamide, enzastaurin, epirubicin, epithilone B, ERA-923, Erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, INO1001, interferon, interleukin-12, ipilimumab, irinotecan, JNJ-16241199, ketoconazole, KRX-0402, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, Neratinib, neuradiab, nilotinib, nilutimide, nolatrexed, NVP-BEZ235, oblimersen, octreotide, ofatumumab, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PM-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, ticilimumab, tipifarnib, tivozanib, TM-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, ZSTK474.

In an embodiment of the invention, an antibody or antigen-binding fragment thereof of the invention is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an antibody or antigen-binding fragment thereof is in association with an agent which treats or prevents such a deficiency, such as, e.g., filgrastim, PEG-filgrastim, erythropoietin, epoetin alfa or darbepoetin alfa.

In an embodiment of the invention, an antibody or antigen-binding fragment thereof of the invention is administered in association with anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures. In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with an antibody or antigen-binding fragment thereof is surgical tumorectomy.

The term "in association with" indicates that the components administered in a method of the present invention can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

Pharmaceutical Compositions and Administration

To prepare pharmaceutical or sterile compositions of the antibodies and antigen-binding fragments of the invention, the antibody or antigen-binding fragment thereof is admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an antibody or antigen-binding fragment thereof of the invention in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the antibodies or antigen-binding fragments thereof of the invention can be administered by an invasive route such as by injection. In further embodiments of the invention, an antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention or a pharmaceutical composition thereof. The present invention also provides an injection device comprising any of the antibodies or antigen-binding fragments of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the antibody or antigen-binding fragment of the invention in a local rather than systemic manner, for example, via injection of the antibody or fragment directly into a tumor. Furthermore, one may administer the antibody or fragment in a targeted drug delivery system, for example, in a liposome coated with a tissue-specific antibody, targeting, for example, a tumor, e.g., characterized by immunopathology. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies are may be desirable.

Antibodies or antigen-binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, 10 μg/kg, 100 μg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:151-144). Doses may also be provided to achieve a pre-determined target concentration of anti-CTLA4 antibody in the subject's serum, such as 0.1, 0.3, 1, 3, 10, 30, 100, 300 μg/ml or more. In other embodiments, an anti-CTLA4 antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an antibody or antigen-binding fragment thereof of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an antibody or antigen-binding fragment, as discussed herein in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an antibody or antigen-binding fragment thereof of the invention or a pharmaceutical composition thereof in one container (e.g., in a sterile glass or plastic vial) and a pharmaceutical composition thereof and/or a therapeutic agent in another container (e.g., in a sterile glass or plastic vial).

In another embodiment, the kit comprises a combination of the invention, including an antibody or antigen-binding fragment thereof of the invention along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Detection Kits and Therapeutic Kits

Also provided is a kit comprising an antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-CTLA4 antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-CTLA4 antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-CTLA4 antibody or fragment. In certain embodiments, an anti-CTLA4 antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

Deposit of Biological Materials

The hybridoma cell line LT002 (CTLA4-4G10) was deposited at China Center for Typical Culture Collection (CCTCC; Address: Wuhan University, Wuhan, China, Post Code: 430072) on Jun. 16, 2015, under the deposit number CCTCC NO: C201587.

Specific Embodiments

The embodiments of the invention will be described below in details with reference to the Examples. Those skilled in the art will understand that the following Examples shall merely illustrate the invention. They shall not be construed, whatsoever, to limit the scope of the invention. Examples, for which specific techniques or conditions are not described, were performed using the technique or condition disclosed in the literatures of the art (e.g., written by J. Sambrook et al., translated by Peitang HUANG et al., Molecular Cloning: A Laboratory Manual, Third Edition, Science Press) or following the instructions provided with the products. Reagents and instruments, for which the supplier is not indicated, are conventional products which are commercially available.

In the following Examples, the T cells used were obtained from Akeso Biopharma Inc., Zhongshan, and the BALB/Cmice were purchased from Guangdong Medical Laboratory Animal Center.

Example 1: Preparation of the CTLA4-mFc Fusion Protein

1. Synthesis of the CTLA4-mFc Gene

According to the design, CTLA4-mFc (SEQ ID NO: 1) was obtained by fusing the extracellular fragment of the CTLA4 gene (Cytotoxic T-Lymphocyte Antigen 4, NCBI Genbank ID: NP_005205.2), CTLA4ECD with the Fc fragment of mouseIgG, mFc (Ig gamma-2A chain C region: ACCESSION: P01863, 99-330). In order to increase the expression efficiency of the gene of interest in the 293f cell expression system, the nucleic acid sequence encoding the CTLA4-mFc protein sequence was optimized at Genscript Co., mainly taking the factors such as codon preference, GC content, secondary structures of mRNA, and repeated sequences into consideration. The optimized gene encoding the CTLA4-mFc fusion protein was sequenced, and the fusion protein was produced at Genscript Co.

2. Construction of the pUC57simple-CTLA4-mFc Plasmid

The CTLA4-mFcfusion gene (SEQ ID NO: 2) was cloned into the pUC57simple expression vector (provided by Genscript Co.) via the restriction sites of the endonucleases Xba I and BamH I at Genscript Co., resulting in the pUC57simple-CTLA4-mFc plasmid.

3. Construction and Extraction of the pcDNA3.1-CTLA4-mFc Recombinant Plasmid

The pUC57simple-CTLA4-mFc plasmid was digested with the endonucleases Xba I and BamH I. The CTLA4-mFc fusion gene fragment was recovered via electrophoresis and was ligated into the pcDNA3.1 expression vector (purchased from Invitrogen Co.) via the restriction sites of the endonucleases Xba I and BamH I. The resultant pcDNA3.1-CTLA4-mFc plasmid was used to transfect the competent cells of the DH5a strain of *E. coli* (purchased from TIANGEN Co.). Transfection and culture were performed following the instructions. *E. coli* colonies positive for pcDNA3.1-CTLA4-mFc were screened out and propagated following conventional methods. Then, the pcDNA3.1-CTLA4-mFc recombinant plasmid was extracted using a kit (purchased from Tiangen Biotech (Beijing) Co. LTD, Cat. No. DP103-03) following the instructions provided with the kit.

Cells of 293F (purchased from Invitrogen Co.) were transfected with the pcDNA3.1-CTLA4-mFc recombinant plasmid using the lipofectamin transfection kit (purchased from Invitrogen Co.), and cultured at 37° C. under 5% $CO_2$ in an incubator. Seven days after transfecting 293F cells with the pcDNA3.1-CTLA4-mFc recombinant plasmid, the CTLA4-mFc fusion protein was purified from the culture liquid by high speed centrifugation, vacuum filtration through a microporous filter membrane, and HiTrap protein A HP column chromatography.

After purification, samples were taken, added into the reductive loading buffer for protein electrophoresis, and examined by SDS-PAGE electrophoresis. As shown in FIG. 1, the protein of interest is shown as a band at about 45 kD.

The amino acid sequence of the CTLA4-mFc fusion protein (364 aa) is: A MH V AQP AV V L ASSRGIASPYCE Y AS PGK ATE V RVIYLRQ ADSQVTE VC A ATY M MGN ELTFLDDSICTGTSSGNQVNLTIQGLRAMDTG-LYICKVELMYPPPYYLGIGNGTQIYVID PEPCPDSDE-NLYF0GPRGPTIKPCPPCKCPAPNLLGGPSVF1FPPK1-KDVLM1SLSP1VTCV VVDVSEDDPDVOISWFVNN-VEVHTAOTOTHREDYNSTLRVVSALPIOHODWMS-GKEF KCKVNNKPLPAPlERTISKPKPKigSYRAQVYVLfF-FEEEMTKKQYTLTCMVTPFMEPIY VEWTNNGK-TELNYKNTEPVLDSPGSYFMYSKLRVEKKNWVERN-SYSCSVVHEGLHN HHTTKSFSRTPGK(SEQ ID NO: 1). wherein the CTLA4 ECD portion is underlined with a wavy line and the mFc portion is underlined with a solid line.

The nucleotide sequence encoding the CTLA4-mFc fusion protein (1092 bp) is: GC A ATGC ATCTCGCAC AGCCTGC AGT GGTCCTGGC A AGCTCC AGGGG A AT CGCTAG
wherein the CTLA4 ECD portion is underlined with a wavy line and the mFc portion is underlined with a solid line.

Example 2: Generation of the Anti-CTLA4 Antibody 4G10

1. Generation of the Hybridoma Cell Line LT002

Using the CTLA4-mFc fusion protein prepared in Example 1 as the immunogen, hybridoma cells were obtained by fusing the splenic cells from the immunized BALB/C mice (purchased from Guangdong Medical Laboratory Animal Center) with mouse myeloma cells following an established method (e.g., Stewart, S. J., "Monoclonal Antibody Production", in Basic Methods in antibody Production and Characterization, Eds. G. C. Howard and D. R. Bethell, Boca Raton: CRC Press, 2000).

The CTLA4-mFc fusion protein was cleaved with the TEV protease, and the CTLA4 protein was obtained by purification on a column. The CTLA4 protein was used as the antigen to coat an ELISA plate, and hybridoma cells secreting novel antibodies specifically binding to CTLA4 were obtained by a primary indirect ELISA screening. Next, hybridoma cells secreting monoclonal antibodies which competed with the ligand B7-1 (CD80, NCBI Gene ID: 941) or B7-2 (CD86, NCBI Gene ID: 942) for binding to CTLA4 were obtained by a secondary competitive ELISA screening from the hybridoma cells obtained in the primary indirect ELISA screening. Then, a stable hybridoma cell line was obtained via limited dilution. The hybridoma cell line was designated as the hybridoma cell line LT002 (CTLA4-4G10), and the monoclonal antibody secreted by the hybridoma cell line was designated as 4G10.

The hybridoma cell line LT002 (CTLA4-4G10) was deposited at China Center for Typical Culture Collection (CCTCC; Address: Wuhan University, Wuhan, China, Post Code: 430072) on Jun. 16, 2015, under the deposit number CCTCC NO: C201587.

2. Preparation of the Anti-CTLA4 Antibody 4G10

The LT002 cell line obtained above was cultured in the IMDM medium supplemented with 10% fetal bovine serum with low IgG and 1% Penicillin-Streptomycin at 37° C. under 5% $CO_2$ in a cell incubator. Seven days later, the supernatant of the cell culture was collected to purify the antibody 4G10 (see Example 1 for the purification method).

Example 3: Sequence Analysis of the Anti-CTLA4 Antibody 4G10 and Generation of the Recombinant Antibody 4G10(Re)

1. Sequence Analysis of the 4G10Antibody

Following the instructions of the Cultured Cell/Bacteria Total RNA Extraction Kit (Tiangen, Cat. No. DP430), mRNA was extracted from the LT002 cell line cultured in Example 2. Following the instructions of the Invitrogen SuperScript® III First-Strand Synthesis System for RT-PCRkit, cDNA was synthesized and amplified by PCR. The PCR amplification product was immediately subjected to TA cloning, following the instructions of the pEASY-T1 Cloning Kit (TransGen, Cat. No. CT101).

The product of TA cloning was immediately subjected to sequencing, and the sequencing results of the following are provided in Table 5:

The nucleic acid sequence encoding the heavy chain variable region (372 bp):(SEQ ID NO: 3) and the encoded amino acid sequence (124 aa): (SEQ ID NO: 4). The nucleic acid sequence encoding the light chain variable region (378 bp): (SEQ ID NO: 5) and the encoded amino acid sequence (126 aa): (SEQ ID NO: 6).

2. Preparation of the Recombinant Antibody 4G10(Re)

The cDNA sequence of the heavy chain (SEQ ID NO: 3 and the sequence of the constant region Ig gamma-1 chain C region, ACCESSION: P01857) and the cDNA sequence of the light chain (SEQ ID NO: 5 and the constant region Ig kappa chain C region, ACCESSION: P01834) of 4G10 were separately cloned into the pUC57 simple vector (provided by Genscript Co.) via the restrictions sites of the endonucleases XbaI and BamHI, resulting in the plasmids pUC57simple-4G1OH and pUC57simple-4G10L, respectively.

The plasmids pUC57simple-4G1OH and pUC57simple-4G10L were digested with the endonuclease HindIII and EcoRI, respectively. The fragments encoding the heavy chain and light chain were recovered via electrophoresis and separately subcloned into the pcDNA3.1 vector. The recombinant plasmids were extracted and co-transfected into cells of 293F. After 7 days of cell culture, the recombinant antibody 4G10(Re) was purified from the culture liquid by high speed centrifugation, vacuum filtration through a microporous filter membrane, and HiTrap protein A HP column chromatography.

Example 4: Design and Generation of the Anti-CTLA4 Humanized Antibodies 4G10H1L1 and 4G10H3L3, 4G10H4L3 and 4G10H5L3

1. Design of the Light Chain and Heavy Chain Sequences of the Anti-CTLA4 Humanized Antibodies 4G10H1L1, 4G10H3L3, 4G10H4L3 and 4G10H5L3

Based on the three-dimensional crystal structure of the CTLA4 protein (*Nat. Struct. Biol.* (1997) 4, p. 527) and the sequences of the 4G10 antibody obtained in Example 2, the structure of the antibody was modeled on a computer. Mutations were designed based on the model, resulting in the variable region sequences of the antibodies 4G10H1L1, 4G10H3L3, 4G10H4L3, and 4G10H5L3. The constant region sequences of the antibodies were from the NCBI database. The heavy chain constant region was Ig gamma-1 chain C region, ACCESSION: P01857, and the light chain constant region was Ig kappa chain C region, ACCESSION: P01834.

The designed variable region sequences are provided below.

(1) The Heavy Chain and Light Chain Sequences of the Humanized Monoclonal Antibody 4G10H1L1

The nucleic acid sequence encoding the heavy chain variable region (345 bp):
 (SEQ ID NO: 7) and the encoded amino acid sequence (115 aa):(SEQ ID NO: 8).

The nucleic acid sequence encoding the light chain variable region (327 bp):
 (SEQ ID NO: 9) and the encoded amino acid sequence (109 aa):(SEQ ID NO: 10).

(2) The Heavy Chain and Light Chain Sequences of the Humanized Monoclonal Antibody 4G10H3L3

The nucleic acid sequence encoding the heavy chain variable region (345 bp):
 (SEQ ID NO: 11) and the encoded amino acid sequence (115 aa):(SEQ ID NO: 12).

The nucleic acid sequence encoding the light chain variable region (327 bp):
 (SEQ ID NO: 13) and the encoded amino acid sequence (109 aa):(SEQ ID NO: 14).

(3) The Heavy Chain and Light Chain Sequences of the Humanized Monoclonal Antibody 4G10H4L3

The nucleic acid sequence encoding the heavy chain variable region (345 bp):
 (SEQ ID NO: 15) and the encoded amino acid sequence (115 aa):(SEQ ID NO: 16).

The nucleic acid sequence encoding the light chain variable region (327 bp):
 (SEQ ID NO: 13) and the encoded amino acid sequence (109 aa):(SEQ ID NO: 14).

(4) The Heavy Chain and Light Chain Sequences of the Humanized Monoclonal Antibody 4G10H5L3

The nucleic acid sequence encoding the heavy chain variable region:
 (SEQ ID NO: 17) and the encoded amino acid sequence: (SEQ ID NO: 18).

The nucleic acid sequence encoding the light chain variable region (327 bp):
 (SEQ ID NO: 13) and the encoded amino acid sequence (109 aa):(SEQ ID NO: 14).

2. Preparation of the Humanized Antibodies 4G10H1L1, 4G10H3L3, 4G10H4L3 and 4G10H5L3

The humanized antibodies were prepared following the method described above in Example 2 for the preparation of 4G10(Re). The cDNA sequence of the heavy chain (SEQ ID NO: 7 and the constant region Ig gamma-1 chain C region, ACCESSION: P01857) and the cDNA sequence of the light chain (SEQ ID NO: 9 and the constant region Ig kappa chain C region, ACCESSION: P01834) of 4G10H1L1, the cDNA sequence of the heavy chain (SEQ ID NO: 11 and the constant region Ig gamma-1 chain C region, ACCESSION: P01857) and the cDNA sequence of the light chain (SEQ ID NO: 13 and the constant region Ig kappa chain C region, ACCESSION: P01834) of 4G10H3L3, and the cDNA sequence of the heavy chain (SEQ ID NO: 15 and the constant region Ig gamma-1 chain C region, ACCESSION: P01857) and the cDNA sequence of the light chain (SEQ ID NO: 13 and the constant region Ig kappa chain C region, ACCESSION: P01834) of 4G10H4L3 were cloned into the pUC57simple vector (provided by Genscript Co.), and the cDNA sequence of the heavy chain (SEQ ID NO: 17 and the constant region Ig gamma-1 chain C region, ACCESSION: P01857) and the cDNA sequence of the light chain (SEQ ID NO: 13 and the constant region Ig kappa chain C region, ACCESSION: P01834) of 4G10H5L3 were cloned into the pUC57simple vector (provided by Genscript Co.) respectively, resulting in the plasmids pUC57simple-4G10H1, pUC57simple-4G10L1; pUC57simple-4G10H3, and pUC57simple-4G10L3; and pUC57simple-4G10H4, and pUC57simple-4G10L3, and and pUC57simple-4G10H5, and pUC57simple-4G10L3. The plasmids were then subcloned into the pcDNA3.1 vector, respectively. After transfecting cells of 293F with the recombinant plasmids, the culture liquid was collected to purify the humanized antibodies 4G10H1L1, 4G10H3L3, 4G10H4L3 and 4G10H5L3.

Example 5: Determination of the Dynamic Parameters of the Antibodies

1. Determination of the Dynamic Parameters of the Binding of the Antibody 4G10 and its Humanized Antibodies 4G10H1L1, 4G10H3L3 and 4G10H4L3 to the Antigen CTLA4

The dynamic parameters of the antigen—antibody binding were determined using the ForteBio molecular interaction analyzer (Octet). The CTLA4-mFc fusion protein prepared in Example 1 was cleaved using the TEV protease, and the CTLA4 antigen was obtained by purification on a column. The 4G10 antibody was immobilized on the surface of the AR2G sensor by amino coupling, and blocked with ethanolamine. After equilibration in PBST, the CTLA4 antigen was added for binding. CTLA4 was serially 2× diluted in PBST, and the following concentrations were obtained: 268.1, 134.1, 67, 33.5, 16.8, 8.38, 4.19, 0 nM. Dissociation occurred in PBST. The humanized antibodies 4G10H1L1, 4G10H3L3 and 4G10H4L3 were detected by a method similar to that used by 4G10, and the antigen concentrations were 180, 90, 45, 22.5, 11.25, 5.625, 2.813, and 0 nM.

Figure 2:
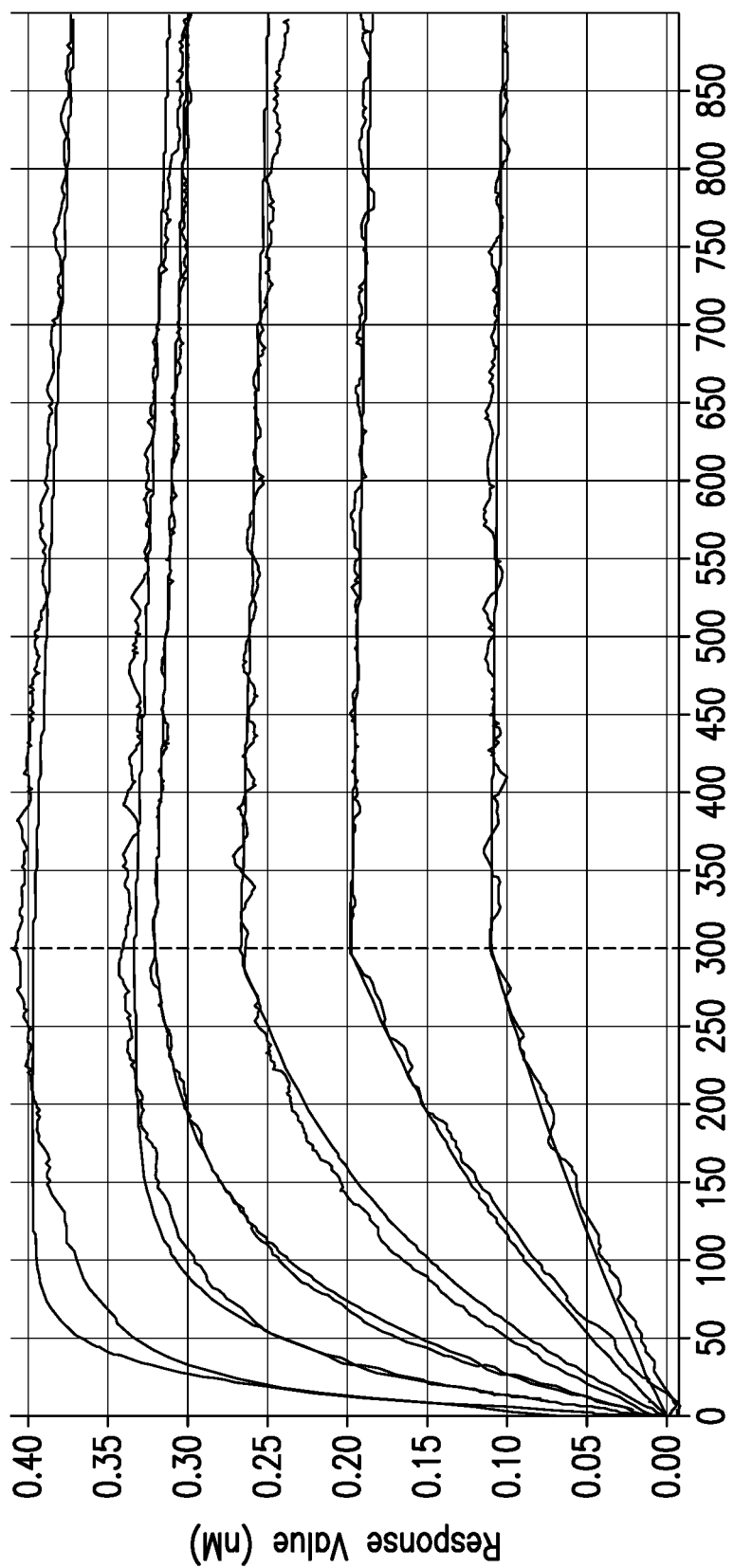
FIG. 2 shows results of determining the dynamic characteristic parameters of the 4G10 antibody.
Figure 3:
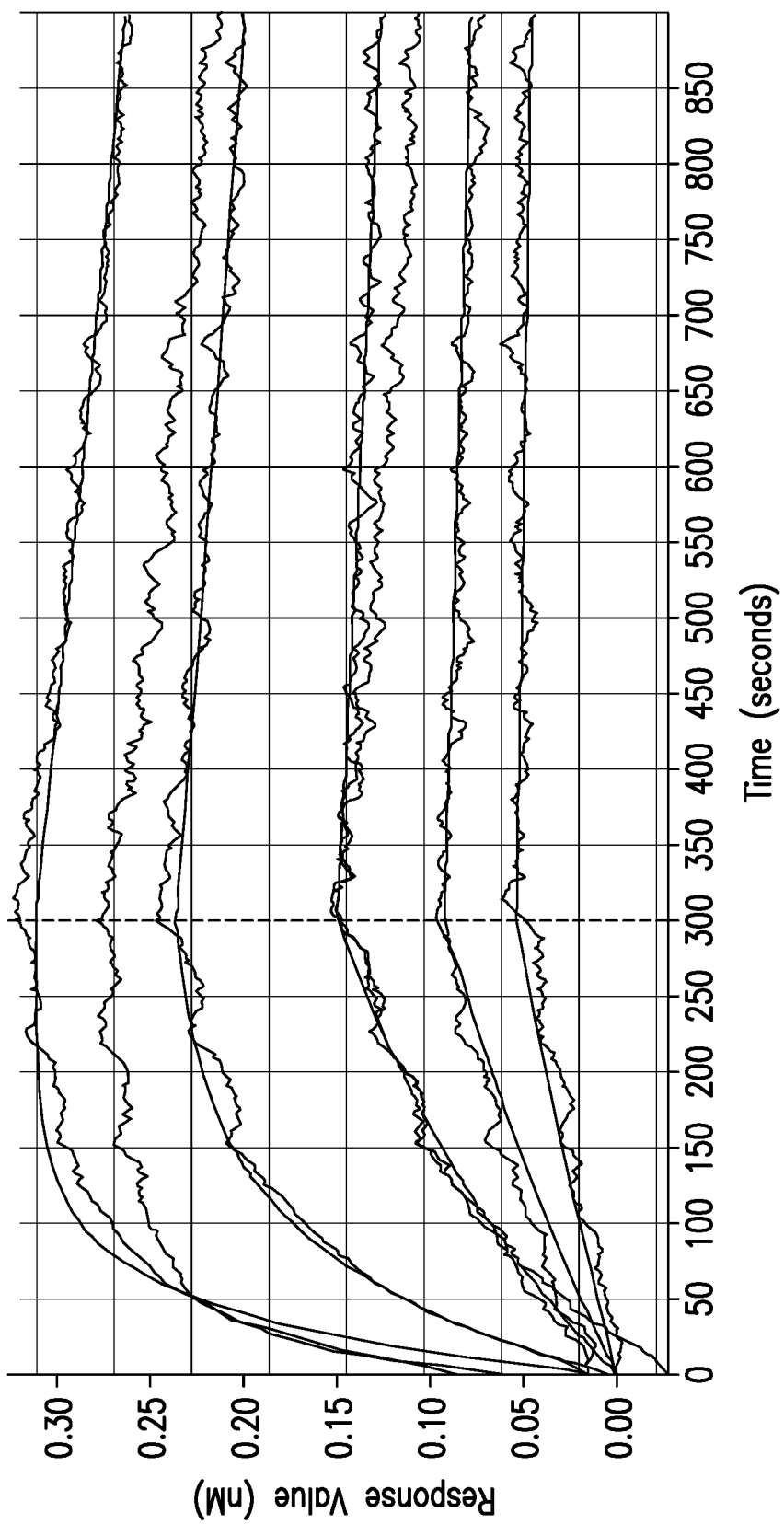
FIG. 3 shows results of determining the dynamic characteristic parameters of the 4G10H1L1 antibody.
Figure 4:
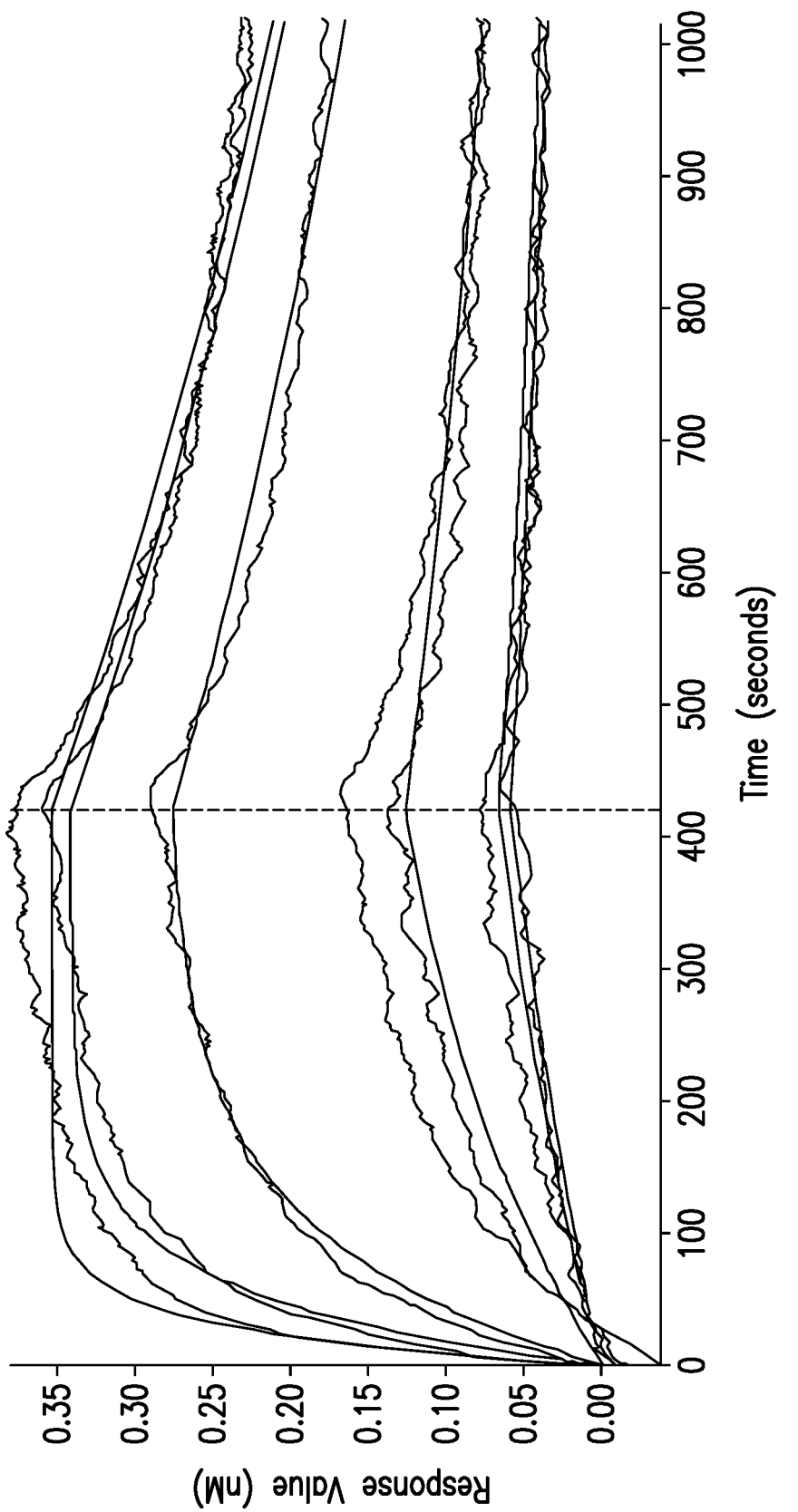
FIG. 4 shows results of determining the dynamic characteristic parameters of the 4G10H3L3 antibody.

The results of determining the dynamic parameters of the binding of the antibody 4G10 and its humanized antibodies 4G10H1L1, 4G10H3L3 and 4G10H4L3 to the antigen are provided in Table 1 below, and the results of determining the dynamic characteristic parameters are shown in FIG. 2, FIG. 3 and FIG. 4, respectively.

TABLE 1

Dynamic parameters of antigen -antibody binding

| Antibody | $K_D$ (M) | $k_{on}$(1/Ms) | error of $k_{on}$ | $k_{dis}$(1/s) | error of $k_{dis}$ |
|---|---|---|---|---|---|
| 4G10 | 3.01E−10 | 3.78E+05 | 4.36E+03 | 1.14E−04 | 5.33E−06 |
| 4G10 H1L1 | 1.52E−09 | 1.86E+05 | 3.26E+03 | 2.82E−04 | 9.23E−06 |
| 4G10 H3L3 | 4.14E−09 | 2.09E+05 | 3.81E+03 | 8.64E−04 | 1.11E−05 |
| 4G10H4L3 | 9.67E−10 | 1.37E+05 | 2.22E+03 | 1.32E−04 | 8.69E−06 |
| 10D1 | 1.21E−09 | 4.67E+05 | 1.15E+04 | 5.65E−04 | 1.51E−05 |

$K_D$, affinity constant; $k_{on}$, antigen—antibody association rate; $k_{dis}$, antigen—antibody dissociation rate; $K_D = k_{dis}/k_{on}$. Control antibody 10D1 was an anti-CTLA4 antibody (SEQ ID NO: 35 and SEQ ID NO: 36).

The results demonstrate that antibody 4G10 and its humanized antibodies 4G10H1L1 and 4G10H3L3 have a good affinity for the antigen, wherein the antibody 4G10 has a stronger affinity for the antigen than 4G10H1L1 and 4G10H3L3.

Example 6: Determination of the Activity of the Antibodies to Bind to the Antigens by ELISA The activity of the humanized antibodies 4G10H1L1 and 4G10H3L3 to bind to CTLA4 was determined by indirect ELISA, respectively. After addition of the antigen, the ELISA plate was incubated at 4° C. overnight. After blocking with 1% BSA at 37° C. for 2 h, the antibody was added, and the plate was incubated at 37° C. for 30 min. The HRP labeled goat-anti-human IgG (H+L) secondary antibody (Jackson, 109-035-088) was added, and TMB (Neogen, 308177) was added for development of 5 min. The absorbance at the wavelength of 450 nm was determined on an ELISA plate reader.

Figure 5:
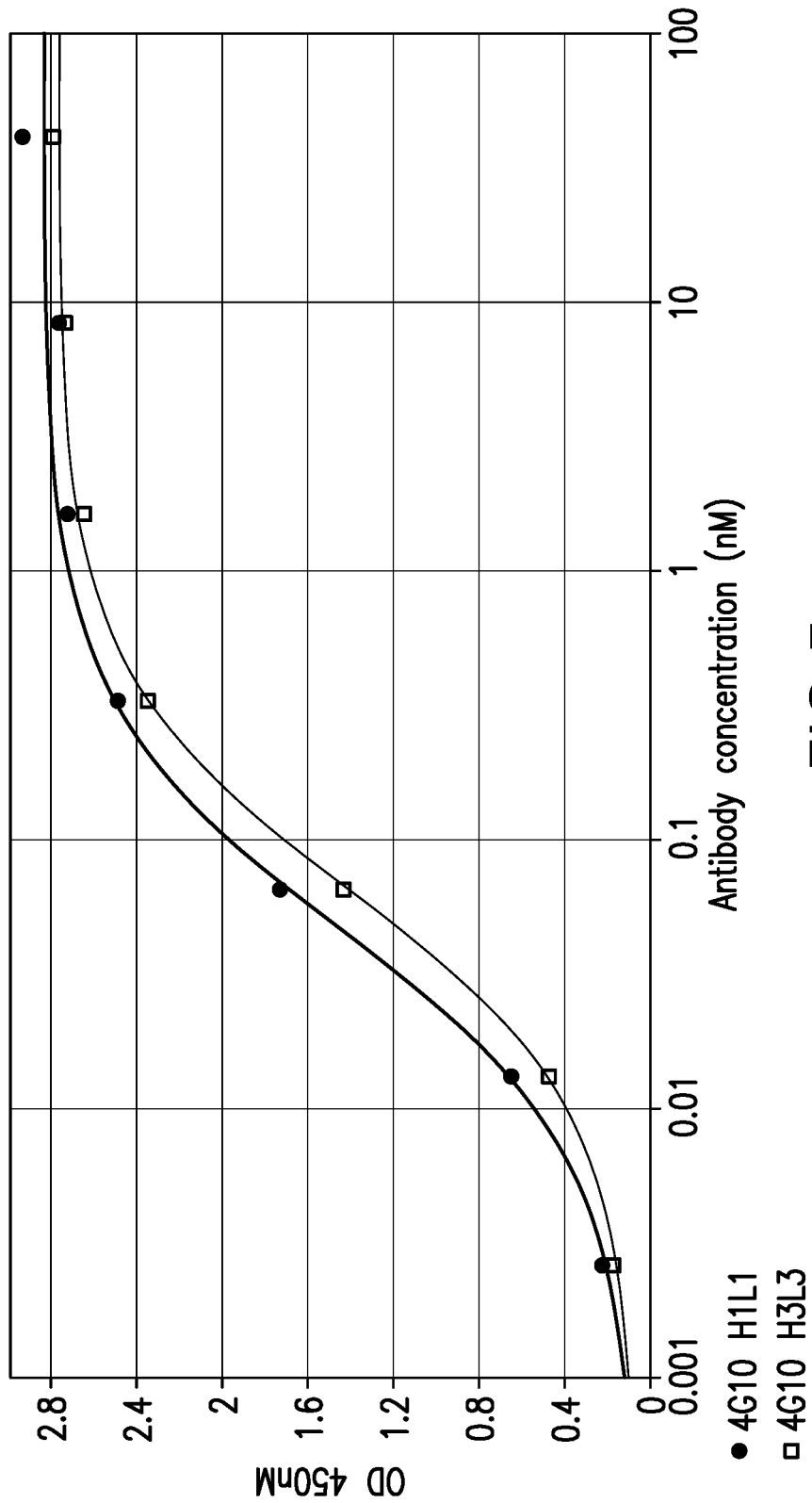
FIG. 5 shows determination of the binding of the antibodies 4G10H1L1 and 4G10H3L3 to the CTLA4 antigen using indirect ELISA.

The results are shown in FIG. 5. As shown in the figure, the humanized antibodies 4G10H1L1 and 4G10H3L3 both can effectively bind to the CTLA4 protein, and their binding efficiency is dose-dependent. The fluorescent intensities at each dose are provided in Table 2. The binding efficiency, EC50, of the antibodies 4G10H1L1 and 4G10H3L3 was obtained by curve simulation in the fluorescent quantitative analysis of the bound antibodies, which was 0.048 and 0.067 nM, respectively.

TABLE 2

Indirect ELISA determining the binding of 4G10H1L1 and 4G10H3L3 to CTLA4

| | CTLA4 | | CTLA4 2 µg/ml | | | |
|---|---|---|---|---|---|---|
| Antibody dilution | 0.5 µg/ml 4G10 H1L1 | | 4G10 H3L3 (20150717) | | PcAb (10D1) | |
| 1 µg/ml | 2.891 | 2.901 | 2.879 | 2.794 | 2.829 | 2.859 |
| 1:3 | 2.833 | 2.868 | 2.941 | 2.899 | 2.828 | 2.905 |
| 1:9 | 2.675 | 2.743 | 2.806 | 2.859 | 2.779 | 2.886 |
| 1:27 | 2.458 | 2.420 | 2.562 | 2.504 | 2.552 | 2.489 |
| 1:81 | 1.627 | 1.607 | 1.792 | 1.672 | 1.804 | 1.862 |
| 1:243 | 0.755 | 0.746 | 0.949 | 0.883 | 0.988 | 1.014 |
| 1:729 | 0.353 | 0.365 | 0.419 | 0.394 | 0.449 | 0.444 |
| 0 | 0.084 | 0.085 | 0.088 | 0.090 | 0.083 | 0.086 |
| Secondary antibody | Goat anti-Human IgG, HRP conjugated (1:5000) | | | | | |
| EC50 (nM) | 0.074 | | 0.063 | | 0.055 | |

1.2. Determination of the Activity of the Humanized Antibodies 4G10H1L1 and 4G10H3L3 to Compete with B7 for Binding to the CTLA4 Antigen by Competitive ELISA B7/1-hFc (Human B7/1 Genbank ID NP 005182.1) was made according to the method described in example 1. The ELISA plate was coated with B7/1-hFc at 4° C. overnight. After blocking with 1% BSA for 2 h, the mixture of the antibody and the CTLA4-mFc antigen was added (see Table 3 for the concentration of the diluents). After incubation at 37° C. for 30 min, the enzyme labeled secondary antibody was added for incubation of 1 h. Then, the substrate was added for incubation of 30 min at 37° C. The absorbance at 450 nm was determined on an ELISA plate reader (see Table 3).

Figure 6:
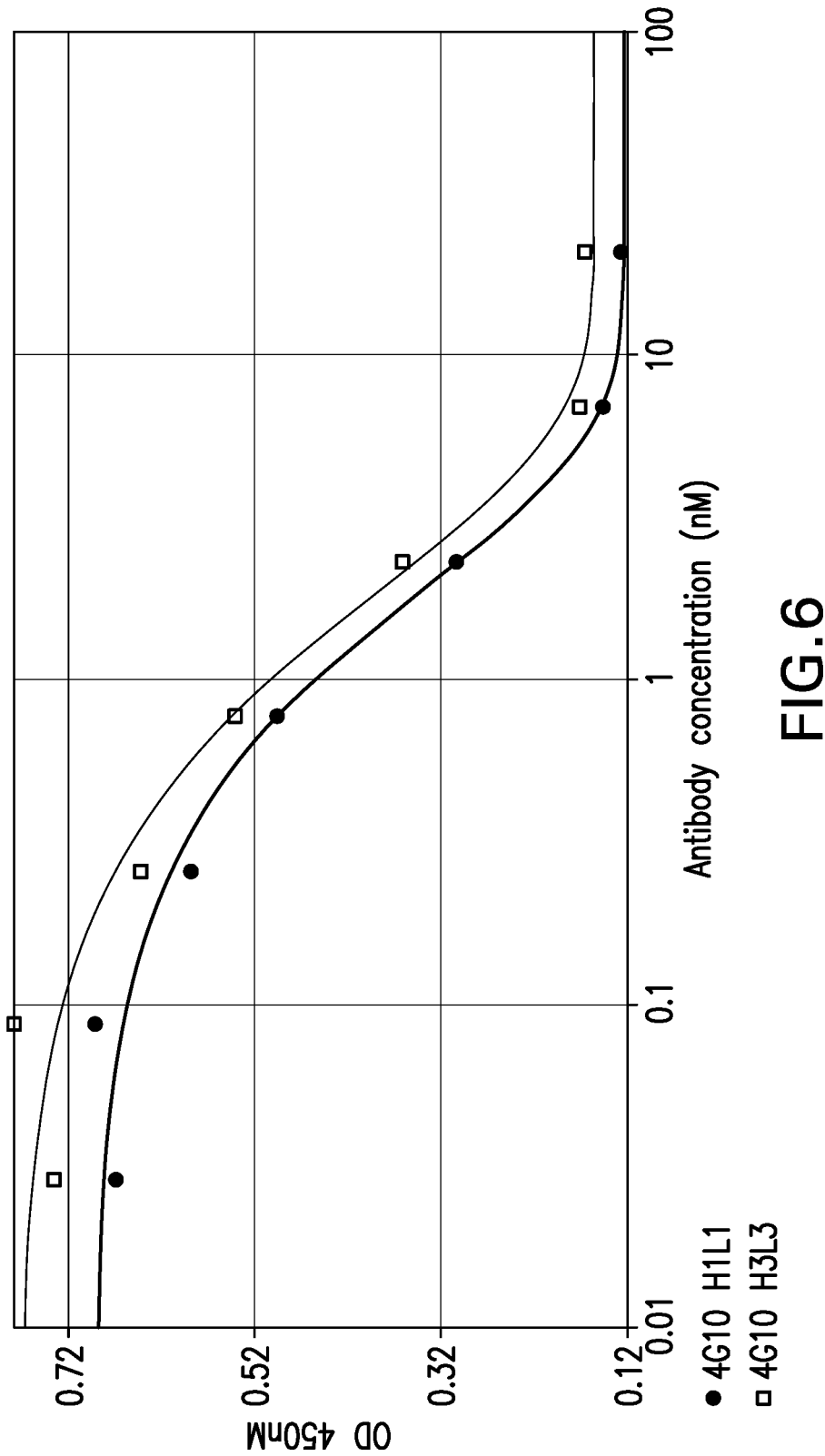
FIG. 6 shows determination of the activity of the antibodies 4G10H1L1 and 4G10H3L3 to compete with B7 for binding to the CTLA4 antigen using competitive ELISA.

The results of determining the competition of the antibodies with B7-1 for binding to the CTLA4 antigen are shown in FIG. 6. As shown in the figure, the antibodies 4G10H1L1 and 4G10H3L3 can effectively compete with B7-1 for binding to the CTLA4 protein, and their binding efficiency is dose-dependent. The fluorescent intensities at each dose are provided in Table 3. The binding efficiency, $EC_{50}$ was calculated by curve simulation in the fluorescent quantitative analysis of the bound antibodies 4G10H1L1 and 4G10H3L3, which was 1.297 nM and 1.229 nM, respectively.

TABLE 3

Competitive ELISA determining the efficiency of 4G10H1L1 and 4G10H3L3 to compete with B7 for binding to human CTLA4

| | B7-1-hFc | | B7-1-hFc 1 µg/ml | | | |
|---|---|---|---|---|---|---|
| Antibody dilution | 0.5 µg/ml 4G10 H1L1 | | 4G10 H3L3 (20150717) | | PcAb (10D1) | |
| 3 µg/ml | 0.132 | 0.121 | 0.117 | 0.120 | 0.147 | 0.140 |
| 1:3 | 0.120 | 0.170 | 0.142 | 0.136 | 0.144 | 0.133 |
| 1:9 | 0.260 | 0.343 | 0.251 | 0.252 | 0.351 | 0.312 |
| 1:27 | 0.399 | 0.593 | 0.313 | 0.284 | 0.442 | 0.365 |
| 1:81 | 0.565 | 0.614 | 0.600 | 0.734 | 0.572 | 0.663 |
| 1:243 | 0.628 | 0.753 | 0.670 | 0.736 | 0.556 | 0.554 |
| 1:729 | 0.573 | 0.760 | 0.745 | 0.802 | 0.726 | 0.692 |
| 0 | 0.610 | 0.665 | 0.763 | 0.761 | 0.888 | 0.732 |
| Receptor | CTLA4-mFc: 0.3 ug/ml | | | | | |
| Secondary antibody | Goat anti-Mouse IgG (H + L), HRP conjugated (1:5000) | | | | | |
| EC50 (nM) | 1.372 | | 0.481 | | 1.121 | |

Example 7: Flow Cytometry Determining the Activity of the Antibodies to Bind to the Antigens on the Surface of Cells First, 293T host cells expressing the CTLA4 were generated, and labeled with the humanized antibodies prepared in the present invention, respectively. Then, the ability of the antibodies to specifically bind to the antigens having native conformation on, the surface of cells was verified by flow cytometry.

1. Generation of 293T Host Cells Expressing the CTLA4

Cells of 293T were transfected with the plasmids pLenti6.3-CTLA4 for CTLA4 (the pLenti6.3 was purchased from Invitrogen Co.). After screening, a clonal cell population stably expressing CTLA4 (293T-CTLA4) was obtained.

2. Determination of the Binding of the Antibodies to the Antigens on the Surface of Cells The host cells expressing the antigens as generated above were digested with trypsin following a conventional method, and $2 \times 10^5$ cells were added to each collection tube. The antibodies were serially diluted in PBS containing 1% BSA. After incubation with 293T cells expressing the corresponding antigen on ice for 2 hours, 100 µL FITC labeled goat-anti-human IgG (1:500) was added to each tube, and the tubes were incubated on ice for 1 hour. After washing with PBS for 3 times, 300 µL PBS was added to resuspend the cells, and the fluorescent signal was detected using the FITC channel on the flow cytometer.

Figure 7:
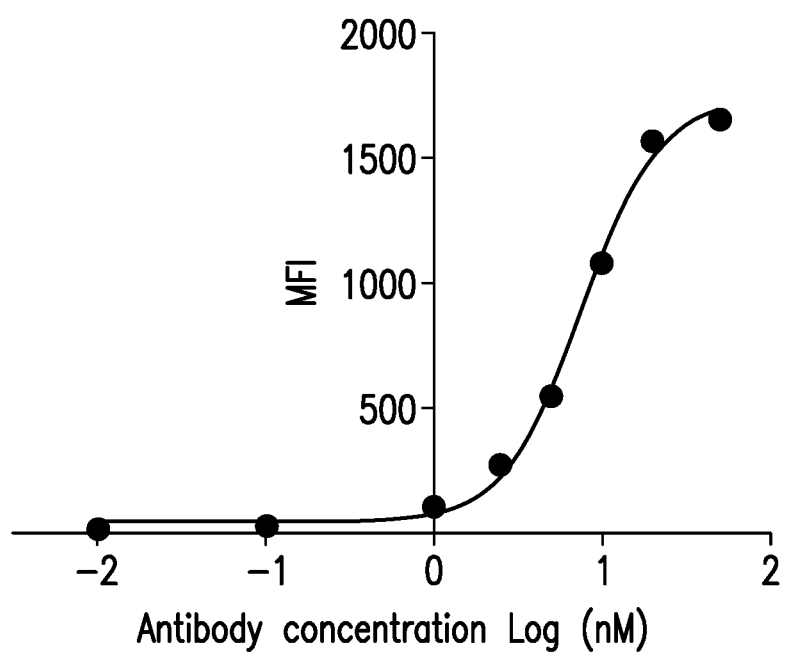
FIG. 7 shows $EC_{50}$ of the binding of the antibody 4G10H1L1 to the protein CTLA4 on the surface of the 293T-CTLA4 cells. MFI stands for Mean Fluorescent Intensity.
Figure 8:
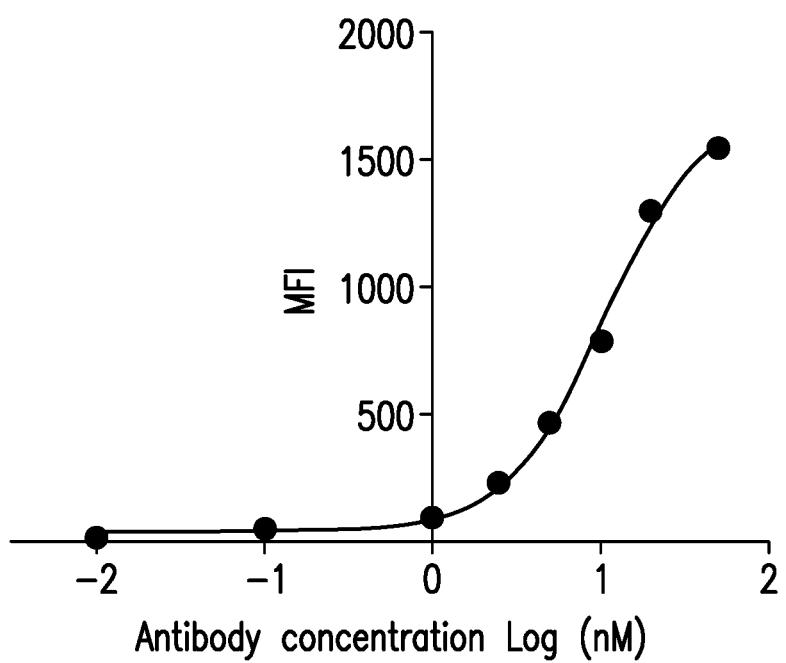
FIG. 8 shows $EC_{50}$ of the binding of the antibody 4G10H3L3 to the protein CTLA4 on the surface of the 293T-CTLA4 cells.

2.1 Results of Determining the Binding of the Antibodies to the Antigen on the Surface of Cells The results of the binding of the humanized antibodies 4G10H1L1 and 4G10H3L3 to 293T-CTLA4 cells are shown in FIG. 7 and FIG. 8, respectively. As shown in the figures, the 4G10H1L1 and 4G10H3L3 antibodies can effectively bind to the CTLA4 target protein on the surface of the 293T-CTLA4 host cell, and their binding efficiency is dose-dependent. The fluorescent intensities at each dose are provided in Table 4. The binding efficiency, $EC_{50}$, of the 4G10H1L1 and 4G10H3L3 antibodies was obtained by curve simulation in the fluorescent quantitative analysis of the bound antibodies 4G10H1L1 and 4G10H3L3, which were 7.58 nM and 5.4 nM, respectively.

TABLE 4

Fluorescent intensity analysis determining the binding of 4G10H1L1 and 4G10H3L3 to the antigen on the surface of the CTLA4 host cell 293T-CTLA4

| Antibody concentration (nM) | 4G10H1L1 | 4G10H2L3 |
|---|---|---|
| | Fluorescent intensity | |
| 0.01 | 14.93 | 15.13 |
| 0.1 | 24.79 | 47.05 |
| 1 | 106.77 | 97.27 |
| 2.5 | 272.24 | 236.66 |
| 5 | 547.76 | 465.54 |
| 10 | 1080.91 | 788 |
| 20 | 1568.19 | 1296.95 |
| 50 | 1652.26 | 1539.24 |

2. The Activity of the Antibodies to Bind to the CTLA4 on the Surface of T Cells Cells of PBMC were isolated using Ficoll-Paque Plus (GE Healthcare, LOT No.: 171440-02), and $CD4^+$ cells were isolated from PBMC. After stimulation with PHA (50 µl/ml) for 3 days, the cells were washed once with PBS. Then, the antibodies were added at different concentrations, wherein control antibody 10D1 was a human anti-CTLA4 antibody. After incubation on ice for 1.5 h, the cells were washed once with PBS. Then, FITC-labeled anti-human secondary antibody IgG (Jackson Immunoresearch, lot. 102155) was added. After incubation on ice for 1 h in the dark, the cells were washed once with PBS and detected on a flow cytometer.

Figure 9:
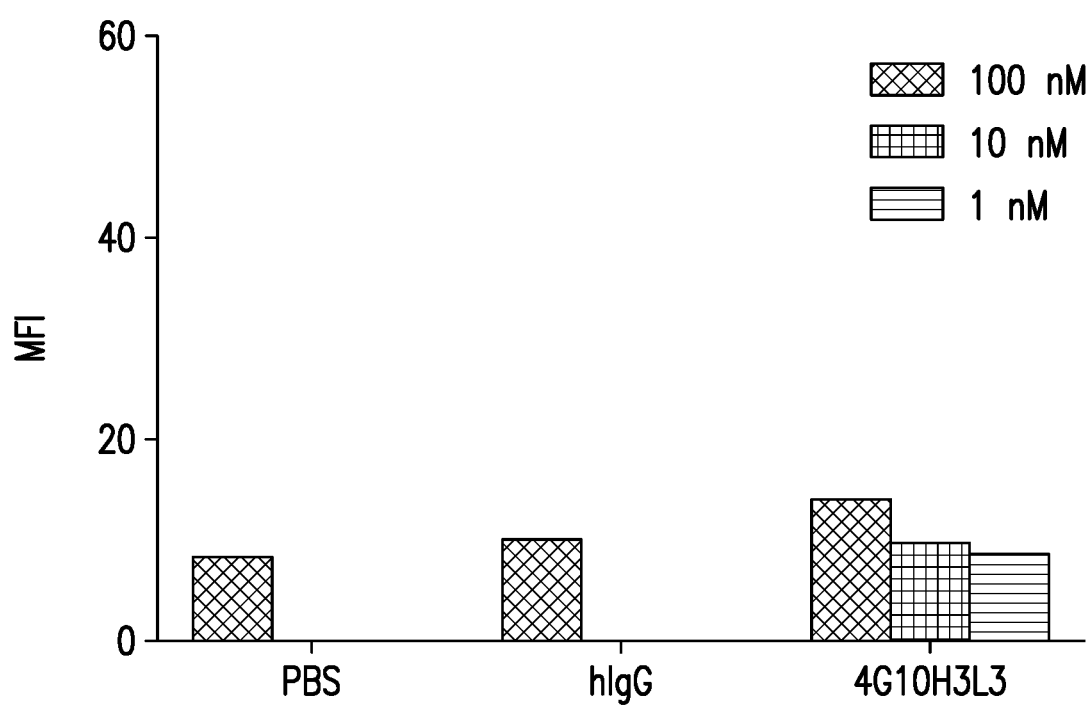
FIG. 9 shows activity of the antibody 4G10H3L3 to bind to the antigen CTLA4 on the surface of T cells.

The results of the binding of the humanized antibody 4G10H1L1 and 4G10H3L3 to T cells are shown in FIG. 9. As shown in the figure, the 4G10H1L1 and 4G10H3L3 antibodies can effectively bind to the CTLA-4 target protein on the surface of T cells, and their binding efficiency is dose-dependent.

Example 8: Mixed Lymphocyte Reaction: Secretion of the Cytokines IFN-γ and IL-2

Cells of PBMC were isolated using Ficoll-Paque Plus (GE Healthcare, LOT No.: 171440-02), and IL-4 (Peprotech, K2513, 1000 U/ml) and GM-CSF (Peprotech, H1513, 1000 U/ml) were added to the isolated cells. After induction of 6 days, TNF-α (Peprotech, G1513, 200 U/ml) was added to induce DC cells for 3 days.

T-cells were isolated from PBMC, and mixed with DC cells at a ratio of 10:1. The antibodies (or hIgG as control) were added at different concentrations. After incubation for 5-6 days, the amounts of IFN-γ and IL-2 secreted were determined using an ELISA kit for IFN-γ (purchased from Dakewe Co.) and IL-2 (purchased from Dakewe Co.), respectively.

Figure 10:
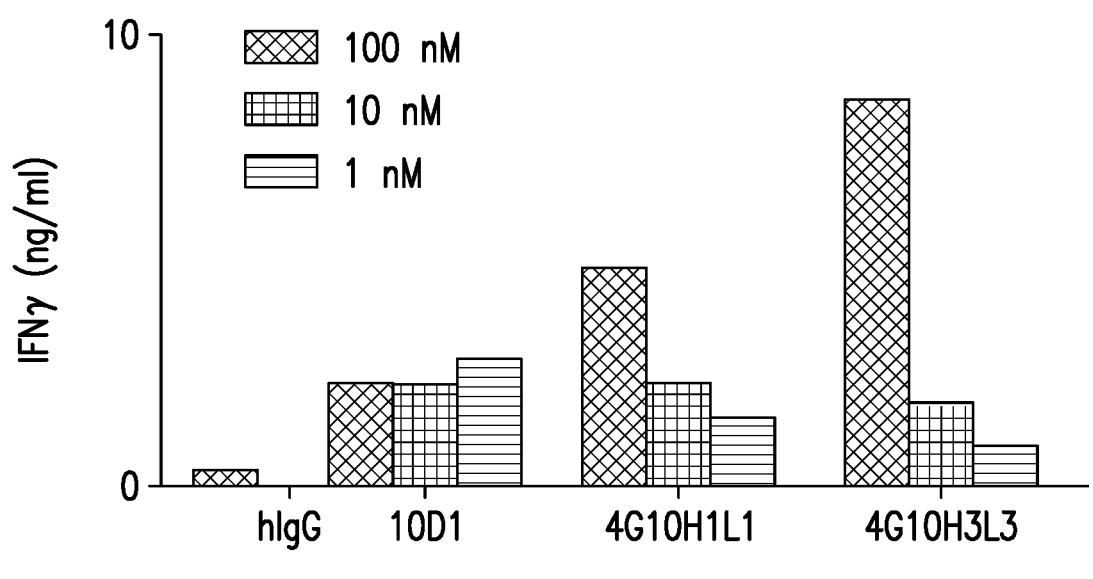
FIG. 10 shows effects of the antibodies 4G10H1L1 and 4G10H3L3 on the secretion of the cytokine IFN-γ in mixed lymphocytes.
Figure 11:
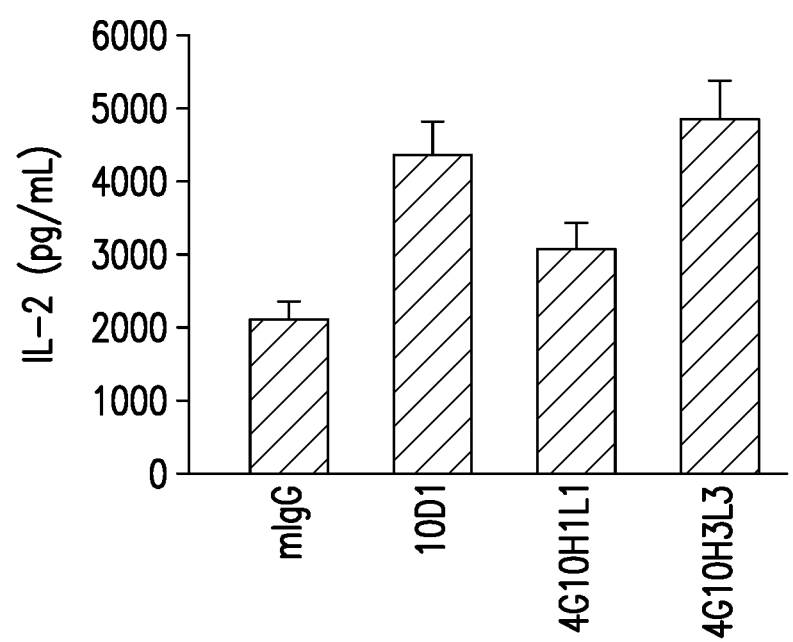
FIG. 11 shows effect of the antibody 4G10H1L1 and 4G10H3L3 on the secretion of the cytokine IL-2 in mixed lymphocytes.
Figure 12:
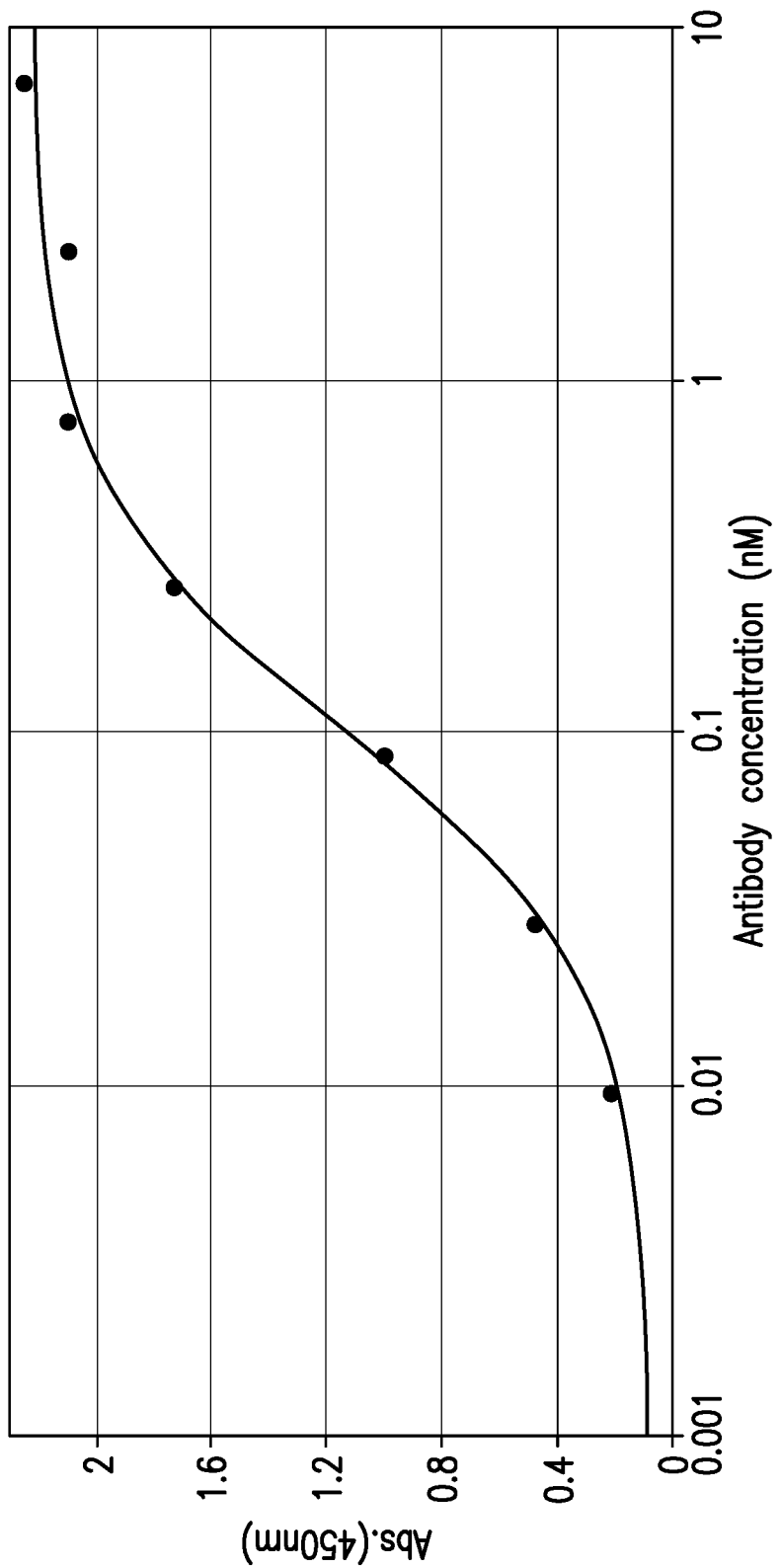
FIG. 12 shows binding of antibody 4G103L3 binding to cyno CTLA-4.

The results of determining the IFN-γ secretion after mixed culture of DC cells and T cells are shown in FIG. 10. The results of determining the IL-2 secretion after mixed culture of DC cells and T cells are shown in FIG. 11.

As shown in the figures, the antibodies 4G10H1L1 and 4G10H3L3, can effectively induce mixed lymphocytes to secrete IFN-γ and IL-2, wherein the effects of the anti-CTLA4 antibodies 4G10H1L1 and 4G10H3L3 in inducing IFN-γ secretion at the concentration of 100 nM were better than the effect of the control antibody 10D1 (FIG. 10).

While the specific embodiments of the invention have been described in details, those skilled in the art, in light of the teaching disclosed in the specification, will understand that various changes and modifications can be made to the details, all of which fall into the protection scope of the present invention. The full scope of the invention is set forth in the appended claims and equivalents thereof

TABLE 5

Summary of sequences

| SEQ ID NO | AA or NT | Description | Sequence |
|---|---|---|---|
| 1. | AA | CTLA4-mFc | In specification |
| 2. | NT | CTLA4-mFc | In specification |

TABLE 5-continued

Summary of sequences

| SEQ ID NO | AA or NT | Description | Sequence |
|---|---|---|---|
| 3. | NT | VH 4G10 | CAGGTCAAGCTGCAGGAGTCTGGACCTGAGCTGGTGAAGCC TGGAGCTTCAATGAAGATATCCTGCAAGGCTTCTGGTTACTC ATTCACTGGCTACACCATGAACTGGGTGAAGCAGAGCCATG GAAAGAACCTTGAATGGATTGGACTTATTAATCCTTACAATA ATATTACTAACTACAACCAGAAGTTCATGGGCAAGGCCACAT TTACTGTAGACAAGTCATCCAGCACAGCCTACATGGAACTCC TCAGACTGACATCTGAAGACTCTGGAGTCTATTTCTGTGCAA GACTCGACTATAGGTCTTATTGGGGCCAAGGGACTCTGGTCA CTGTCTCTGCAGCCAAAACGACACCCCCATCTGTCTAT |
| 4. | AA | VH 4G10 | QVKLQESGPELVKPGASMKISCKASGYSFTGYTMNWVKQSHG KNLEWIGLINPYNNITNYNQKFMGKATFTVDKSSSTAYMELLRL TSEDSGVYFCARLDYRSYWGQGTLVTVSA |
| 5. | NT | VL 4G10 | CAGGCTGTTGTGACTCAGGAATCTGCACTCACCACATCACCT GGTGAAACAGTCACACTCACTTGTCGCTCAAGTACTGGGGCT GTTACAACTAGTAACTTTGCCAACTGGGTCCAAGAAAAACCA GATCATTTATTCACTAGTCTAATAGGTGGTACCAACAACCGAG CTCCAGGTGTTCCTGCCAGATTCTCAGGCTCCCTGATTGGAG ACAAGGCTGCCCTCACCATCACAGGGGCACAGACTGAGGAT GAGGCAATATATTTCTGTGCTCTATGGTACAGCAACCATTGGG TGTTCGGTGGAGGAACCAAACTGACTGTCCTAGGCCAGCCCA AGTCTTCGCCATCAGTCACCCTGTTTCAAGGGCAATTCTGC |
| 6. | AA | VL 4G10 | QAVVTQESALTTSPGETVTLTCRSSTGAVTTSNFANWVQEKPDH LFTSLIGGTNNRAPGVPARFSGSLIGDKAALTITGAQTEDEAIYF CALWYSNHWVFGGGTKLTVLGQPKSSPSVTLFQGQFC |
| 7. | NT | VH 4G10H1 | CAGGTGCAGCTGGTGGAGTCTGGGGCCGAGCTGGTGAAGCC CGGCGCCTCCATGAAGATCTCTTGCAAGGCCAGCGGATACAG TTTCACTGGCTATACCATGAACTGGGTCAAACAGGCTCCAGG ACAGGGACTGGAGTGGATCGGGCTGATTAATCCTTACAACAA CATCACCAACTACAACCAGAAGTTCATGGGAAAAGCAACCTT TACAGTGGACAAGAGCATTTCCACAGCCTACATGGAACTGAG CCGGCTGACTTCAGACGATAGCGGGGTCTATTTTTGTGCAAG GCTGGATTATCGCTCTTACTGGGGGCAGGGAACTCTGGTCAC TGTCTCCGCT |
| 8. | AA | VH 4G10H1 | QVQLVESGAELVKPGASMKISCKASGYSFTGYTMNWVKQAPG QGLEWIGLINPYNNITNYNQKFMGKATFTVDKSISTAYMELSRL TSDDSGVYFCARLDYRSYWGQGTLVTVSA |
| 9. | NT | VL 4G10L1 | CAGGCTGTCGTCACTCAGGAACCTTCACTGACTGTGAGCCCA GGAGGAACTGTCACCCTGACATGCGGAAGCTCCACCGGAGC AGTGACCACATCCAACTTCGCCAATTGGGTCCAGGAAAAGCC AGGCCAGGCATTTCGATCCCTGATCGGAGGCACAAACAATCG GGCTTCTTGGGTGCCCGCAAGATTCTCAGGAAGCCTGCTGGG GGGAAAAGCCGCTCTGACCATTAGTGGCGCTCAGCCTGAGG ACGAAGCCGAGTACTTCTGCGCTCTGTGGTATAGCAACCACT GGGTGTTTGGCGGGGGAACAAAGCTGACTGTGCTG |
| 10. | AA | VL 4G10L1 | QAVVTQEPSLTVSPGGTVTLTCGSSTGAVTTSNFANWVQEKPGQ AFRSLIGGTNNRASWVPARFSGSLLGGKAALTISGAQPEDEAEY FCALWYSNHWVFGGGTKLTVL |
| 11. | NT | VH 4G10H3 | CAGGTGCAGCTGGTCGAGTCTGGGGCCGAAGTGAAGAAACC CGGCGCCTCAGTGAAGGTCAGCTGCAAGGCCAGCGGGTACA GTTTCACTGGATATACCATGAACTGGGTCCGACAGGCCCCTG GCCAGGGGCTGGAGTGGATCGGCCTGATTAACCCTTACAACA ACATCACTAACTACGCACAGAAGTTCCAGGGGAGAGTGACCT TTACAGTGGACACCAGCATTTCCACAGCCTACATGGAACTGT CCCGGCTGAGATCTGACGATACAGGCGTGTACTTCTGCGCTA GGCTGGATTACCGCAGCTATTGGGACAGGGCACACTGGTGA CTGTCAGCGCA |
| 12. | AA | VH 4G10H3 | QVQLVESGAEVKKPGASVKVSCKASGYSFTGYTMNWVRQAPG QGLEWIGLINPYNNITNYAQKFQGRVTFTVDTSISTAYMELSRLR SDDTGVYFCARLDYRSYWGQGTLVTVSA |
| 13. | NT | VL 4G10L3 | CAGGCTGTCGTCACTCAGGAACCTTCACTGACCGTGTCTCCT GGCGGGACTGTCACCCTGACATGCGGCAGCTCCACAGGGGC CGTGACCCAAGTAACTTCCCAAATTGGGTCCAGCAGAAGCC AGGACAGGCTCCCCGGAGTCTGATCGGAGGCACCAACAACA |

TABLE 5-continued

Summary of sequences

| SEQ ID NO | AA or NT | Description | Sequence |
|---|---|---|---|
| | | | AGGCCAGCTGGACACCCGCACGGTTCAGCGGCAGCCTGCTG GGCGGCAAGGCCGCTCTGACAATTAGCGGAGCCCAGCCTGA GGACGAAGCCGAGTACTATTGCGCTCTGTGGTACTCCAACCA CTGGGTGTTCGGCGGCGGCACCAAGCTGACTGTGCTG |
| 14. | AA | VL 4G10L3 | QAVVTQEPSLTVSPGGTVTLTCGSSTGAVTTSNFPNWVQQKPG QAPRSLIGGTNNKASWTPARFSGSLLGGKAALTISGAQPEDEA EYYCALWYSNHWVFGGGTKLTVL |
| 15. | NT | VH 4G10H4 | CAGGTGCAGCTGGTCGAGTCTGGGGCCGAAGTGAAGAAAC CCGGCGCCTCAGTGAAGGTCAGCTGCAAGGCCAGCGGGTAC AGTTTCACTGGATATACCATGAACTGGGTCCGACAGGCCCCT GGCCAGGGGCTGGAGTGGATCGGCCTGATTAACCCTTACAA CGACATCACTAACTACGCACAGAAGTTCCAGGGGAGAGTGA CCTTTACAGTGGACACCAGCATTTCCACAGCCTACATGGAAC TGTCCCGGCTGAGATCTGACGATACAGGCGTGTACTTCTGCG CTAGGCTGGATTACCGCAGCTATTGGGGACAGGGCACACTG GTGACTGTCAGCGCA |
| 16. | AA | VH 4G10H4 | QVQLVESGAEVKKPGASVKVSCKASGYSFTGYTMNWVRQAP GQGLEWIGLINPYNDITNYAQKFQGRVTFTVDTSISTAYMELSR LRSDDTGVYFCARLDYRSYWGQGTLVTVSA |
| 17. | NT | VH 4G10H5 | CAGGTGCAGCTGGTCGAGTCTGGGGCCGAAGTGAAGAAAC CCGGCGCCTCAGTGAAGGTCAGCTGCAAGGCCAGCGGGTAC AGTTTCACTGGATATACCATGAACTGGGTCCGACAGGCCCCT GGCCAGGGGCTGGAGTGGATCGGCCTGATTAACCCTTACAA CAACATCGATAACTACGCACAGAAGTTCCAGGGGAGAGTGA CCTTTACAGTGGACACCAGCATTTCCACAGCCTACATGGAAC TGTCCCGGCTGAGATCTGACGATACAGGCGTGTACTTCTGCG CTAGGCTGGATTACCGCAGCTATTGGGGACAGGGCACACTG GTGACTGTCAGCGCA |
| 18. | AA | VH 4G10H5 | QVQLVESGAEVKKPGASVKVSCKASGYSFTGYTMNWVRQAP GQGLEWIGLINPYNNIDNYAQKFQGRVTFTVDTSISTAYMELSR LRSDDTGVYFCARLDYRSYWGQGTLVTVSA |
| 19. | AA | 4G10 VH consensus (humanized) | QVQLVESGAEX$_1$KKPGASX$_2$KX$_3$SCKASGYSFTGYTX4NWVX$_5$ QAPGQGLEWIGLINPYNX$_6$IX$_7$NYX$_8$QKFX$_9$GX$_{10}$X$_{11}$TFTVDX$_{12}$SIS TAYMELSRLX$_{13}$SDDX$_{14}$GVYFCARLDYRSYWGQGTLVTVSA<br>X$_1$ = V or L<br>X$_2$ = V or M<br>X$_3$ = V or I<br>X$_4$ = M, V, L, I, G, A, S, T<br>X$_5$ = R or K<br>X$_6$ = N or D or E<br>X$_7$ = T or D or E or G or A<br>X$_8$ = A or N<br>X$_9$ = Q or M<br>X$_{10}$ = R or K<br>X$_{11}$ = V or A<br>X$_{12}$ = T or K<br>X$_{13}$ = R or T<br>X$_{14}$ = T or S |
| 20. | AA | 4G10 VL consensus (humanized) | QAVVTQEPSLTVSPGGTVTLTCGSSTGAVTTSNFX$_1$NWVQ X$_2$KPGQAX$_3$RSLIGGTNNX$_4$AX$_5$WX$_6$PARFSGSLLGGKAALTISG AQPEDEAEYX$_7$CALX$_8$YSNHX$_9$VFGGGTKLTVL<br>X$_1$ = P or A<br>X$_2$ = Q or E<br>X$_3$ = P or F<br>X$_4$ = K or R or any other amino acid except for M or C<br>X$_5$ = S or P<br>X$_6$ = T or V<br>X$_7$ = Y or F<br>X$_8$ = W or any amino acid except M or C<br>X$_9$ = W or any amino acid except M or C |
| 21. | AA | HCDR1 4G10 | GYTX$_1$N<br>X$_1$ = M, V, L, I, G, A, S, T |

TABLE 5-continued

Summary of sequences

| SEQ ID NO | AA or NT | Description | Sequence |
|---|---|---|---|
| 22. | AA | HCDR2 4G10 | LINPYNX$_1$IX$_2$NYX$_3$QKFX$_4$G<br>X$_1$ = N, D<br>X$_2$ = T, D, E, G or A<br>X$_3$ = A or N<br>X$_4$ = Q or M |
| 23. | AA | HCDR3 4G10 | LDYRSY |
| 24. | AA | LCDR1 4G10 | GSSTGAVTTSNFX$_1$N<br>X$_1$ = P or A |
| 25. | AA | LCDR2 4G10 | GTNNX$_1$AX$_2$<br>X$_1$ = K, R or any amino acid except M or C<br>X$_2$ = S or P |
| 26. | AA | LCDR3 4G10 | ALX$_1$YSNHX$_2$<br>X$_1$ = W or any amino acid except M or C<br>X$_2$ = W or any amino acid except M or C |
| 27. | AA | HCDR1 4G10 | GYSFTGYT |
| 28. | AA | HCDR2 4G10 | INPYNX$_1$IX$_2$<br>X$_1$ = N, D or E<br>X$_2$ = T, D, E, G or A |
| 29. | AA | HCDR3 4G10 | ARLDYRSY |
| 30. | AA | LCDR1 4G10 | TGAVTTSNF |
| 31. | AA | LCDR2 4G10 | GTN |
| 32. | AA | LCDR3 4G10 | ALX$_1$YSNHX$_2$V<br>X$_1$ = W or any amino acid except M or C<br>X$_2$ = W or any amino acid except M or C |
| 33. | AA | Exemplary heavy chain IgG1 constant domain | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKKVEPKSCDKTHTCPPCPAPELLGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALPAP IEKTISKAKGQPREPQVYTLPPSRDELTKNQVSLTCLVKGFYPS DIAVEWESNGQPENNYKTTPPVLDSDGSFFLYSKLTVDKSRWQ QGNVFSCSVMHEALHNHYTQKSLSLSPGK |
| 34. | AA | Exemplary human kappa chain constant domain | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| 35. | AA | 10D1 heavy chain | QVQLVESGGGVVQPGRSLRLSCAASGFTFSSYTMHWVRQAPG KGLEWVTFISYDGNNKYYADSVKGRFTISRDNSKNTLYLQMN SLRAEDTAIYYCARTGWLGPFDYWQGTLVTVSSASTKGPSVFP LAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPELLGPSVFLFPPPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQPRE PQVYTLPPSRDELTKNQVLTCLVKGFYPDIAVEWESNGQPENN YKTTPPVLDSDGSFFLYSKLTVDKSRWQQGNVFSCSVMHEAL HNHYTQKSLSLSPGK |
| 36. | AA | 10D1 Light chain | EIVLTQSPGTLSLSPGERATLSCRASQSVGSSYLAWYQQKPGQA PRLLIYGAFSRATGIPDRFSGSGSGTDFTLTISRLEPEDFAVYYC QQYGSSPWTFGQGTKVEIKTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC |

The invention claimed is:

1. An antibody or antigen binding fragment thereof that binds to human CTLA4, comprising a heavy chain variable region and a light chain variable region, wherein
   a) the heavy chain variable region comprises:
      an HCDR1 comprising the amino acid sequence of:
         (i) SEQ ID NO: 21, wherein the amino acid at position 4 is Met, or
         (ii) SEQ ID NO: 27,
      an HCDR2 comprising the amino acid sequence of:
         (i) SEQ ID NO: 22, wherein the amino acid at position 7 is Asp or Asn,
         the amino acid at position 9 is Thr or Asp,
         the amino acid at position 12 is Ala or Asn, and
         the amino acid at position 16 is Met or Gln, or
         (ii) SEQ ID NO: 28, wherein the amino acid at position 6 is Asn or Asp and
         the amino acid at position 8 is Thr or Asp; and
      an HCDR3 comprising the amino acid sequence of SEQ ID NO: 23 or SEQ ID NO: 29; and
   b) the light chain variable region comprises:
      an LCDR1 comprising the amino acid sequence of:
         (i) SEQ ID NO: 24, wherein the amino acid at position 13 is Pro or Ala, or
         (ii) SEQ ID NO: 30,
      an LCDR2 comprising the amino acid sequence of:
         (i) SEQ ID NO: 25, wherein amino acid at position 7 is Pro or Ser, and
         the amino acid at position 5 is Arg or Lys, or
         (ii) SEQ ID NO: 31, and
      an LCDR3 comprising the amino acid sequence of:
         (i) SEQ ID NO: 26, wherein the amino acids at position 3 and position 8 are Trp, or
         (ii) SEQ ID NO: 32, wherein the amino acid at position 3 and position 8 are Trp.

2. The antibody or antigen binding fragment thereof of claim 1, selected from the group consisting of:
   a) the heavy chain variable region comprising
      the HCDR1 comprising the amino acid sequence of SEQ ID NO: 21 wherein the amino acid at position 4 is Met,
      the HCDR2 comprising the amino acid sequence of SEQ ID NO: 22 wherein the amino acid at position 7 is Asp or Asn, the amino acid at position 9 is Thr or Asp, the amino acid at position 12 is Ala or Asn, and the amino acid at position 16 is Met or Gln, and
      the HCDR3 comprising the amino acid sequence of SEQ ID NO: 23; and the light chain variable region comprising
      the LCDR1 comprising the amino acid sequence of SEQ ID NO: 24 wherein the amino acid at position 13 is Pro or Ala,
      the LCDR2 comprising the amino acid sequence of SEQ ID NO: 25 wherein the amino acid at position 5 is Lys or Arg and the amino acid at position 7 is Ser or Pro, and
      the LCDR3 comprising the amino acid sequence of SEQ ID NO: 26 wherein the amino acids at positions 3 and 8 are Trp;
   b) the heavy chain variable region comprising
      the HCDR1 comprising the amino acid sequence of SEQ ID NO: 21 wherein the amino acid at position 4 is Met;
      the HCDR2 comprising the amino acid sequence of SEQ ID NO: 22 wherein when the amino acid at positions 7 and 12 is Asn then the amino acid at position 9 is Thr or Asp and the amino acid at position 16 is Met or when the amino acid at position 7 is Asp, then the amino acid at position 9 is Thr or Asp, the amino acid at position 12 is Ala, and the amino acid at position 16 is Gln; and
      the HCDR3 comprising the amino acid sequence of SEQ ID NO: 23; and the light chain variable region comprising
      the LCDR1 comprising the amino acid sequence of SEQ ID NO: 24 wherein the amino acid at position 13 is Pro,
      the LCDR2 comprising the amino acid sequence of SEQ ID NO: 25 wherein the amino acid at position 5 is Lys and the amino acid at position 7 is Ser, and
      the LCDR3 comprising the amino acid sequence of SEQ ID NO: 26 wherein the amino acids at positions 3 and 8 are Trp;
   c) the heavy chain variable region comprising
      the HCDR1 comprising the amino acid sequence of SEQ ID NO: 27,
      the HCDR2 comprising the amino acid sequence of SEQ ID NO: 28, and
      the HCDR3 comprising the amino acid sequence of SEQ ID NO: 29; and the light chain variable region comprising
      the LCDR1 comprising the amino acid sequence of SEQ ID NO: 30,
      the LCDR2 comprising the amino acid sequence of SEQ ID NO: 31, and
      the LCDR3 comprising the amino acid sequence of SEQ ID NO: 32; and
   d) the heavy chain variable region comprising
      the HCDR1 comprising the amino acid sequence of SEQ ID NO: 27, the HCDR2 comprising the amino acid sequence of SEQ ID NO: 28 wherein the amino acid at position 6 is Asn or Asp and the amino acid at position 8 is Thr, and the HCDR3 comprising the amino acid sequence of SEQ ID NO: 29; and a light chain variable region comprising the LCDR1 comprising the amino acid sequence of SEQ ID NO: 30, the LCDR2 comprising the amino acid sequence of SEQ ID NO: 31, and the LCDR3 comprising the amino acid sequence of SEQ ID NO: 32 wherein amino acids at positions 3 and 8 are Trp.

3. The antibody or antigen binding fragment thereof of claim 1, selected from the group consisting of:
  a) the antibody or antigen binding fragment thereof comprising a heavy chain variable region of SEQ ID NO: 4 and a light chain variable region of SEQ ID NO: 6;
  b) the antibody or antigen binding fragment thereof comprising a heavy chain variable region of SEQ ID NO: 8 and a light chain variable region of SEQ ID NO: 10;
  c) the antibody or antigen binding fragment thereof comprising the heavy chain variable region of SEQ ID NO: 12 and the light chain variable region of SEQ ID NO: 14; and
  d) the antibody or antigen binding fragment thereof comprising the heavy chain variable region of SEQ ID NO: 16 and the light chain variable region of SEQ ID NO: 14.

4. The antibody or antigen binding fragment thereof according to claim 1, wherein the antibody or antigen binding fragment thereof is a humanized antibody comprising two heavy chains and two light chains.

5. The antibody or antigen binding fragment thereof according to claim 1, wherein the antibody or antigen binding fragment thereof is a humanized antibody comprising a human IgG1 constant domain and a human kappa constant domain.

6. The antibody or antigen binding fragment thereof according to claim 1, wherein the antigen binding fragment thereof is selected from the group consisting of: a Fab, a Fab', a F(ab')2, a Fd, an Fv, a dAb, a single chain antibody, and a diabody.

7. The antibody or antigen binding fragment thereof according to claim 1, wherein the antibody is produced in a CHO cell.

8. The antibody or antigen binding fragment thereof according to claim 1, wherein the antibody binds to human CTLA4 with a KD less than $1\times10^{-9}$ M to $1\times10^{-12}$ M as determined by surface plasmon resonance or a similar technique.

9. A pharmaceutical composition comprising the antibody or antigen binding fragment thereof according to claim 1, and a pharmaceutically acceptable carrier and/or excipient.

10. The pharmaceutical composition of claim 9, further comprising an agent selected from the group consisting of:
  a. an anti-PD1 antibody or an antigen binding fragment thereof;
  b. an anti-LAG3 antibody or an antigen binding fragment thereof;
  c. an anti-VISTA antibody or an antigen binding fragment thereof;
  d. an anti-TIGIT antibody or an antigen binding fragment thereof;
  e. an anti-TIM3 antibody or an antigen binding fragment thereof;
  f. an anti-HVEM antibody or an antigen binding fragment thereof;
  g. an anti-CD27 antibody or an antigen binding fragment thereof;
  h. an anti-CD137 antibody or an antigen binding fragment thereof;
  i. an anti-OX40 antibody or an antigen binding fragment thereof;
  j. an anti-CD28 antibody or an antigen binding fragment thereof;
  k. an anti-PDL1 antibody or an antigen binding fragment thereof;
  l. an anti-PDL2 antibody or an antigen binding fragment thereof;
  m. an anti-GITR antibody or an antigen binding fragment thereof;
  n. an anti-ICOS antibody or an antigen binding fragment thereof;
  o. an anti-SIRPa antibody or an antigen binding fragment thereof;
  p. an anti-ILT2 antibody or an antigen binding fragment thereof;
  q. an anti-ILT3 antibody or an antigen binding fragment thereof;
  r. an anti-ILT4 antibody or an antigen binding fragment thereof;
  s. an anti-ILT5 antibody or an antigen binding fragment thereof;
  t. an anti-CD73 antibody or an antigen binding fragment thereof; and
  u. an anti-CD47 antibody or an antigen binding fragment thereof.

11. The pharmaceutical composition of claim 10, wherein the anti-PD1 antibody or the antigen binding fragment thereof is selected from the group consisting of: pembrolizumab or an antigen binding fragment thereof and nivolumab or an antigen binding fragment thereof.

12. A conjugate comprising the antibody or antigen binding fragment thereof according to claim 1 and a conjugated moiety, wherein the conjugated moiety is a detectable label.

13. A method of producing an antibody or antigen binding fragment comprising:
  a. culturing a host cell comprising a polynucleotide encoding at least one of the heavy chain variable region and the light chain variable region of claim 1; and
  b. recovering the antibody or antigen binding fragment from at least one of the host cell and culture medium.

14. A method of treating cancer in a human subject, comprising administering to the human subject an effective amount of the antibody or antigen binding fragment thereof of claim 1.

15. A method of treating an infection or infectious disease in a human subject, comprising administering to the human subject an effective amount of the antibody or antigen binding fragment thereof of claim 1.

16. A method for detecting the presence of a CTLA4 peptide or a fragment thereof in a sample comprising:
  contacting the sample with an antibody or antigen binding fragment thereof of claim 1; and
  detecting the presence of a complex between the antibody or antigen binding fragment thereof and the peptide; wherein detection of the complex indicates the presence of the CTLA4 peptide.

17. A method of increasing the activity of an immune cell, comprising administering to a subject in need thereof an effective amount of an antibody or antigen binding fragment thereof according to claim 1.

18. The method of claim 17, wherein said antibody or antigen binding fragment thereof is administered for:
   a) treatment of cancer;
   b) treatment of an infection or infectious disease; or
   c) a vaccine adjuvant.

19. A hybridoma cell line that secretes an antibody that binds to CTLA4, wherein the antibody comprises a heavy chain variable region of SEQ ID NO: 4 and a light chain variable region of SEQ ID NO: 6.

20. An isolated polypeptide comprising an amino acid sequence selected from the group consisting of SEQ ID NOs: 4, 6, 8, 10, 12, 14, and 16.

21. An isolated nucleic acid molecule encoding the antibody or antigen binding fragment thereof according to claim 1, or the polypeptide of claim 20.

22. A vector comprising the isolated nucleic acid molecule according to claim 21.

23. A host cell comprising the vector according to claim 22.

24. A host cell comprising the isolated nucleic acid according to claim 21, or the vector according to claim 22.

\* \* \* \* \*

SEQUENCE LISTING

<160> NUMBER OF SEQ ID NOS: 36

<210> SEQ ID NO 1
<211> LENGTH: 364
<212> TYPE: PRT
<213> ORGANISM: Artificial Sequence
<220> FEATURE:
<223> OTHER INFORMATION: CTLA4-mFc fusion protein

<400> SEQUENCE: 1

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45

Cys Ala Ala Thr Tyr Met Met Gly Asn Glu Leu Thr Phe Leu Asp Asp
        50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Asp Glu Asn Leu
            115                 120                 125

Tyr Phe Gln Gly Pro Arg Gly Pro Thr Ile Lys Pro Cys Pro Pro Cys
        130                 135                 140

Lys Cys Pro Ala Pro Asn Leu Leu Gly Gly Pro Ser Val Phe Ile Phe
145                 150                 155                 160

Pro Pro Lys Ile Lys Asp Val Leu Met Ile Ser Leu Ser Pro Ile Val
                165                 170                 175

Thr Cys Val Val Val Asp Val Ser Glu Asp Asp Pro Asp Val Gln Ile
                180                 185                 190

Ser Trp Phe Val Asn Asn Val Glu Val His Thr Ala Gln Thr Gln Thr
            195                 200                 205

His Arg Glu Asp Tyr Asn Ser Thr Leu Arg Val Val Ser Ala Leu Pro
        210                 215                 220

Ile Gln His Gln Asp Trp Met Ser Gly Lys Glu Phe Lys Cys Lys Val
225                 230                 235                 240

Asn Asn Lys Asp Leu Pro Ala Pro Ile Glu Arg Thr Ile Ser Lys Pro
                245                 250                 255

Lys Gly Ser Val Arg Ala Pro Gln Val Tyr Val Leu Pro Pro Pro Glu
                260                 265                 270

Glu Glu Met Thr Lys Lys Gln Val Thr Leu Thr Cys Met Val Thr Asp
            275                 280                 285

Phe Met Pro Glu Asp Ile Tyr Val Glu Trp Thr Asn Asn Gly Lys Thr
        290                 295                 300

Glu Leu Asn Tyr Lys Asn Thr Glu Pro Val Leu Asp Ser Asp Gly Ser
305                 310                 315                 320

Tyr Phe Met Tyr Ser Lys Leu Arg Val Glu Lys Asn Trp Val Glu
                325                 330                 335

Arg Asn Ser Tyr Ser Cys Ser Val Val His Glu Gly Leu His Asn His
                340                 345                 350

His Thr Thr Lys Ser Phe Ser Arg Thr Pro Gly Lys 355          360

<210> SEQ ID NO 2
<211> LENGTH: 1092
<212> TYPE: DNA
<213> ORGANISM: Artificial Sequence
<220> FEATURE:
<223> OTHER INFORMATION: CTLA4-mFC fusion

<400> SEQUENCE: 2

```
gcaatgcatg tcgcacagcc tgcagtggtc ctggcaagct ccaggggaat cgctagcttc      60
gtgtgcgaat acgcttcccc aggcaaggca accgaggtcc gggtgacagt cctgagacag     120
gccgacagcc aggtgacaga gtctgcgcc gctacttata tgatgggcaa cgagctgacc     180
tttctggacg atagcatttg taccgggaca tctagtggaa accaagtgaa tctgaccatc     240
cagggcctgc gcgctatgga cacagggctg tacatttgta aagtggagct gatgtatccc     300
cctccatact atctgggaat cggcaacggg acccagatct acgtgattga tcctgaacca     360
tgccccgact ccgatgagaa tctgtatttc agggaccac gaggcccac aattaagcca     420
tgtccccctt gcaaatgtcc tgcaccaaac ctgctgggag gaccaagcgt gttcatcttt     480
ccacccaaga tcaaggacgt gctgatgatc tcactgagcc ccattgtgac ctgcgtggtc     540
gtggacgtga gcgaggacga tcctgatgtg cagatcagtt ggttcgtcaa caatgtggaa     600
gtccacacag ctcagactca gacccatagg gaggattaca atagtactct gcgcgtcgtg     660
tcagcactgc ccattcagca ccaggactgg atgagcggca aggagttcaa gtgcaaagtg     720
aacaacaagg atctgcccgc acctatcgag agaactattt ccaagcctaa agggtctgtg     780
agggccccac aggtgtatgt cctgcctcca cccgaggaag agatgactaa gaaacaggtg     840
acactgactt gtatggtcac cgacttcatg cccgaagata tctacgtgga gtggactaac     900
aatgggaaga ccgaactgaa ctataaaaat acagagcctg tgctggactc agatggaagc     960
tactttatgt atagcaagct gcgagtggaa aagaaaaact gggtcgagcg gaacagctac    1020
tcttgtagtg tggtccacga agggctgcat aatcaccaca ccactaaatc attctcccga    1080
actccaggca aa                                                         1092
```

<210> SEQ ID NO 3
<211> LENGTH: 372
<212> TYPE: DNA
<213> ORGANISM: Mus musculus

<400> SEQUENCE: 3

```
caggtcaagc tgcaggagtc tggacctgag ctggtgaagc ctggagcttc aatgaagata      60
tcctgcaagg cttctggtta ctcattcact ggctacacca tgaactgggt gaagcagagc     120
catggaaaga accttgaatg gattggactt attaatcctt acaataatat tactaactac     180
aaccagaagt tcatgggcaa ggccacattt actgtagaca gtcatccag cacagcctac     240
atggaactcc tcagactgac atctgaagac tctggagtct atttctgtgc aagactcgac     300
tataggtctt attggggcca agggactctg gtcactgtct ctgcagccaa aacgacaccc     360
ccatctgtct at                                                         372
```

<210> SEQ ID NO 4
<211> LENGTH: 115
<212> TYPE: PRT
<213> ORGANISM: Mus musculus

<400> SEQUENCE: 4

Gln Val Lys Leu Gln Glu Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Asn Ile Thr Asn Tyr Asn Gln Lys Phe
50                  55                  60

Met Gly Lys Ala Thr Phe Thr Val Asp Lys Ser Ser Ser Thr Ala Tyr
65                  70                  75                  80

Met Glu Leu Leu Arg Leu Thr Ser Glu Asp Ser Gly Val Tyr Phe Cys
                85                  90                  95

Ala Arg Leu Asp Tyr Arg Ser Tyr Trp Gly Gln Gly Thr Leu Val Thr
                100                 105                 110

Val Ser Ala
        115

<210> SEQ ID NO 5
<211> LENGTH: 378
<212> TYPE: DNA
<213> ORGANISM: Mus musculus

<400> SEQUENCE: 5
caggctgttg tgactcagga atctgcactc accacatcac ctggtgaaac agtcacactc      60
acttgtcgct caagtactgg ggctgttaca actagtaact ttgccaactg gtccaagaa     120 aaaccagatc atttattcac tagtctaata ggtggtacca acaaccgagc tccaggtgtt    180
cctgccagat tctcaggctc cctgattgga gacaaggctg ccctcaccat cacaggggca    240
cagactgagg atgaggcaat atatttctgt gctctatggt acagcaacca ttgggtgttc    300
ggtggaggaa ccaaactgac tgtcctaggc cagcccaagt cttcgccatc agtcaccctg    360
tttcaagggc aattctgc                                                  378

<210> SEQ ID NO 6
<211> LENGTH: 126
<212> TYPE: PRT
<213> ORGANISM: Mus musculus

<400> SEQUENCE: 6

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Phe Ala Asn Trp Val Gln Glu Lys Pro Asp His Leu Phe Thr Ser
        35                  40                  45

Leu Ile Gly Gly Thr Asn Asn Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly Gln Pro
                100                 105                 110

Lys Ser Ser Pro Ser Val Thr Leu Phe Gln Gly Gln Phe Cys
            115                 120                 125

<210> SEQ ID NO 7
<211> LENGTH: 345
<212> TYPE: DNA
<213> ORGANISM: Artificial Sequence
<220> FEATURE:
<223> OTHER INFORMATION: humanized light chain variable region of 4G10H1L1

<400> SEQUENCE: 7

```
caggtgcagc tggtggagtc tggggccgag ctggtgaagc ccggcgcctc catgaagatc      60
tcttgcaagg ccagcggata cagtttcact ggctatacca tgaactgggt caaacaggct    120
ccaggacagg gactggagtg gatcgggctg attaatcctt acaacaacat caccaactac    180
aaccagaagt tcatgggaaa agcaaccttt acagtggaca gagcatttc cacagcctac    240
atggaactga ccggctgac ttcagacgat agcgggtct attttgtgc aaggctggat      300
tatcgctctt actgggggca gggaactctg gtcactgtct ccgct                     345
```

<210> SEQ ID NO 8
<211> LENGTH: 115
<212> TYPE: PRT
<213> ORGANISM: Artificial Sequence
<220> FEATURE:
<223> OTHER INFORMATION: humanized heavy chain variable region of 4G10H1L1

<400> SEQUENCE: 8

```
Gln Val Gln Leu Val Glu Ser Gly Ala Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ala Pro Gly Gln Gly Leu Glu Trp Ile
        35                  40                  45

Gly Leu Ile Asn Pro Tyr Asn Asn Ile Thr Asn Tyr Asn Gln Lys Phe
    50                  55                  60

Met Gly Lys Ala Thr Phe Thr Val Asp Lys Ser Ile Ser Thr Ala Tyr
65                  70                  75                  80

Met Glu Leu Ser Arg Leu Thr Ser Asp Asp Ser Gly Val Tyr Phe Cys
                85                  90                  95

Ala Arg Leu Asp Tyr Arg Ser Tyr Trp Gly Gln Gly Thr Leu Val Thr
            100                 105                 110

Val Ser Ala
        115
```

<210> SEQ ID NO 9
<211> LENGTH: 327
<212> TYPE: DNA
<213> ORGANISM: Artificial Sequence
<220> FEATURE:
<223> OTHER INFORMATION: humanized light chain variable region of 4G10H1L1

<400> SEQUENCE: 9

```
caggctgtcg tcactcagga accttcactg actgtgagcc caggaggaac tgtcaccctg      60
acatgcggaa gctccaccgg agcagtgacc acatccaact cgccaattg ggtccaggaa    120
aagccaggcc aggcatttcg atccctgatc ggaggcacaa caatcgggc ttcttgggtg    180
cccgcaagat tctcaggaag cctgctgggg ggaaaagccg ctctgaccat tagtggcgct    240
cagcctgagg acgaagccga gtacttctgc gctctgtggt atagcaacca ctgggtgttt    300
``` ggcggggaa caaagctgac tgtgctg                                              327

<210> SEQ ID NO 10
<211> LENGTH: 109
<212> TYPE: PRT
<213> ORGANISM: Artificial Sequence
<220> FEATURE:
<223> OTHER INFORMATION: humanized light chain variable region of
      4G10H1L1

<400> SEQUENCE: 10

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Phe Ala Asn Trp Val Gln Glu Lys Pro Gly Gln Ala Phe Arg Ser
        35                  40                  45

Leu Ile Gly Gly Thr Asn Asn Arg Ala Ser Trp Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 11
<211> LENGTH: 345
<212> TYPE: DNA
<213> ORGANISM: Artificial Sequence
<220> FEATURE:
<223> OTHER INFORMATION: humanized heavy chain variable region of
      4G10H3L3

<400> SEQUENCE: 11
caggtgcagc tggtcgagtc tggggccgaa gtgaagaaac ccggcgcctc agtgaaggtc     60
agctgcaagg ccagcgggta cagtttcact ggatatacca tgaactgggt ccgacaggcc    120
cctggccagg gctggagtg atcggcctg attaacccctt acaacaacat cactaactac    180
gcacagaagt tccaggggag agtgaccttt acagtggaca ccagcatttc cacagcctac    240
atggaactgt cccggctgag atctgacgat acaggcgtgt acttctgcgc taggctggat    300
taccgcagct attggggaca gggcacactg gtgactgtca gcgca                    345

<210> SEQ ID NO 12
<211> LENGTH: 115
<212> TYPE: PRT
<213> ORGANISM: Artificial Sequence
<220> FEATURE:
<223> OTHER INFORMATION: humanized heavy chain variable region of
      4G10H3L3

<400> SEQUENCE: 12

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Ile
        35                  40                  45

Gly Leu Ile Asn Pro Tyr Asn Asn Ile Thr Asn Tyr Ala Gln Lys Phe
    50                  55                  60

Gln Gly Arg Val Thr Phe Thr Val Asp Thr Ser Ile Ser Thr Ala Tyr
65                  70                  75                  80

Met Glu Leu Ser Arg Leu Arg Ser Asp Asp Thr Gly Val Tyr Phe Cys
                85                  90                  95

Ala Arg Leu Asp Tyr Arg Ser Tyr Trp Gly Gln Gly Thr Leu Val Thr
            100                 105                 110

Val Ser Ala
        115

<210> SEQ ID NO 13
<211> LENGTH: 327
<212> TYPE: DNA
<213> ORGANISM: Artificial Sequence
<220> FEATURE:
<223> OTHER INFORMATION: humanized light chain variable region of
      4G10H3L3

<400> SEQUENCE: 13
caggctgtcg tcactcagga accttcactg accgtgtctc ctggcgggac tgtcaccctg      60
acatgcggca gctccacagg ggccgtgacc acaagtaact tcccaaattg ggtccagcag     120
aagccaggac aggctccccg gagtctgatc ggaggcacca acaacaaggc cagctggaca     180
cccgcacggt tcagcggcag cctgctgggc ggcaaggccg ctctgacaat tagcggagcc     240
cagcctgagg acgaagccga gtactattgc gctctgtggt actccaacca ctgggtgttc     300
ggcggcggca ccaagctgac tgtgctg                                         327

<210> SEQ ID NO 14
<211> LENGTH: 109
<212> TYPE: PRT
<213> ORGANISM: Artificial Sequence
<220> FEATURE:
<223> OTHER INFORMATION: humanized light chain variable region of
      4G10H3L3

<400> SEQUENCE: 14

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Phe Pro Asn Trp Val Gln Gln Lys Pro Gly Gln Ala Pro Arg Ser
        35                  40                  45

Leu Ile Gly Gly Thr Asn Asn Lys Ala Ser Trp Thr Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 15
<211> LENGTH: 345
<212> TYPE: DNA
<213> ORGANISM: Artificial Sequence
<220> FEATURE:
<223> OTHER INFORMATION: humanized heavy chain variable region 4G10H4

<400> SEQUENCE: 15
caggtgcagc tggtcgagtc tggggccgaa gtgaagaaac ccggcgcctc agtgaaggtc      60

```
agctgcaagg ccagcgggta cagtttcact ggatatacca tgaactgggt ccgacaggcc      120
cctggccagg ggctggagtg gatcggcctg attaacccct acaacgacat cactaactac      180
gcacagaagt tccaggggag agtgaccttt acagtggaca ccagcatttc cacagcctac      240
atggaactgt cccggctgag atctgacgat acaggcgtgt acttctgcgc taggctggat      300
taccgcagct attggggaca gggcacactg gtgactgtca gcgca                      345
```

<210> SEQ ID NO 16
<211> LENGTH: 115
<212> TYPE: PRT
<213> ORGANISM: Artificial Sequence
<220> FEATURE:
<223> OTHER INFORMATION: humanized heavy chain variable region 4G10H4

<400> SEQUENCE: 16

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Ile
        35                  40                  45

Gly Leu Ile Asn Pro Tyr Asn Asp Ile Thr Asn Tyr Ala Gln Lys Phe
    50                  55                  60

Gln Gly Arg Val Thr Phe Thr Val Asp Thr Ser Ile Ser Thr Ala Tyr
65                  70                  75                  80

Met Glu Leu Ser Arg Leu Arg Ser Asp Asp Thr Gly Val Tyr Phe Cys
                85                  90                  95

Ala Arg Leu Asp Tyr Arg Ser Tyr Trp Gly Gln Gly Thr Leu Val Thr
            100                 105                 110

Val Ser Ala
        115
```

<210> SEQ ID NO 17
<211> LENGTH: 345
<212> TYPE: DNA
<213> ORGANISM: Artificial Sequence
<220> FEATURE:
<223> OTHER INFORMATION: humanized heavy chain variable region 4G10H5

<400> SEQUENCE: 17

```
caggtgcagc tggtcgagtc tggggccgaa gtgaagaaac ccggcgcctc agtgaaggtc       60
agctgcaagg ccagcgggta cagtttcact ggatatacca tgaactgggt ccgacaggcc      120
cctggccagg ggctggagtg gatcggcctg attaacccct acaacaacat cgataactac      180
gcacagaagt tccaggggag agtgaccttt acagtggaca ccagcatttc cacagcctac      240
atggaactgt cccggctgag atctgacgat acaggcgtgt acttctgcgc taggctggat      300
taccgcagct attggggaca gggcacactg gtgactgtca gcgca                      345
```

<210> SEQ ID NO 18
<211> LENGTH: 115
<212> TYPE: PRT
<213> ORGANISM: Artificial Sequence
<220> FEATURE:
<223> OTHER INFORMATION: humanized heavy chain variable region 4G10H5

<400> SEQUENCE: 18

```
Gln Val Gln Leu Val Glu Ser Gly Ala Glu Val Lys Lys Pro Gly Ala
1               5                   10                  15
```

```
Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Ile
            35                  40                  45

Gly Leu Ile Asn Pro Tyr Asn Asn Ile Asp Asn Tyr Ala Gln Lys Phe
 50                  55                  60

Gln Gly Arg Val Thr Phe Thr Val Asp Thr Ser Ile Ser Thr Ala Tyr
 65                  70                  75                  80

Met Glu Leu Ser Arg Leu Arg Ser Asp Asp Thr Gly Val Tyr Phe Cys
                 85                  90                  95

Ala Arg Leu Asp Tyr Arg Ser Tyr Trp Gly Gln Gly Thr Leu Val Thr
            100                 105                 110

Val Ser Ala
        115

<210> SEQ ID NO 19
<211> LENGTH: 115
<212> TYPE: PRT
<213> ORGANISM: Artificial Sequence
<220> FEATURE:
<223> OTHER INFORMATION: humanized 4G10 variable heavy chain region
      consensus sequence
<220> FEATURE:
<221> NAME/KEY: X
<222> LOCATION: (11)..(11)
<223> OTHER INFORMATION: Val or Leu
<220> FEATURE:
<221> NAME/KEY: X
<222> LOCATION: (18)..(18)
<223> OTHER INFORMATION: Val or Met
<220> FEATURE:
<221> NAME/KEY: X
<222> LOCATION: (20)..(20)
<223> OTHER INFORMATION: Val or Ile
<220> FEATURE:
<221> NAME/KEY: X
<222> LOCATION: (34)..(34)
<223> OTHER INFORMATION: Met or Val or Leu or Ile or Gly or Ala or Ser
      or Thr
<220> FEATURE:
<221> NAME/KEY: X
<222> LOCATION: (38)..(38)
<223> OTHER INFORMATION: Arg or Lys
<220> FEATURE:
<221> NAME/KEY: X
<222> LOCATION: (56)..(56)
<223> OTHER INFORMATION: Asn or Asp or Glu
<220> FEATURE:
<221> NAME/KEY: X
<222> LOCATION: (58)..(58)
<223> OTHER INFORMATION: Thr or Asp or Glu or Gly or Ala
<220> FEATURE:
<221> NAME/KEY: X
<222> LOCATION: (61)..(61)
<223> OTHER INFORMATION: Ala or Asn
<220> FEATURE:
<221> NAME/KEY: X
<222> LOCATION: (65)..(65)
<223> OTHER INFORMATION: Gln or Met
<220> FEATURE:
<221> NAME/KEY: X
<222> LOCATION: (67)..(67)
<223> OTHER INFORMATION: Arg or Lys
<220> FEATURE:
<221> NAME/KEY: X
<222> LOCATION: (68)..(68)
<223> OTHER INFORMATION: Val or Ala
<220> FEATURE:
<221> NAME/KEY: X
<222> LOCATION: (74)..(74)
<223> OTHER INFORMATION: Thr or Lys
```

-continued

```
<220> FEATURE:
<221> NAME/KEY: X
<222> LOCATION: (87)..(87)
<223> OTHER INFORMATION: Arg or Thr
<220> FEATURE:
<221> NAME/KEY: X
<222> LOCATION: (91)..(91)
<223> OTHER INFORMATION: Thr or Ser

<400> SEQUENCE: 19

Gln Val Gln Leu Val Glu Ser Gly Ala Glu Xaa Lys Lys Pro Gly Ala
1               5                   10                  15

Ser Xaa Lys Xaa Ser Cys Lys Ala Ser Gly Tyr Ser Phe Thr Gly Tyr
        20                  25                  30

Thr Xaa Asn Trp Val Xaa Gln Ala Pro Gly Gln Gly Leu Glu Trp Ile
        35                  40                  45

Gly Leu Ile Asn Pro Tyr Asn Xaa Ile Xaa Asn Tyr Xaa Gln Lys Phe
50                  55                  60

Xaa Gly Xaa Xaa Thr Phe Thr Val Asp Xaa Ser Ile Ser Thr Ala Tyr
65                  70                  75                  80

Met Glu Leu Ser Arg Leu Xaa Ser Asp Xaa Gly Val Tyr Phe Cys
                85                  90                  95

Ala Arg Leu Asp Tyr Arg Ser Tyr Trp Gly Gln Gly Thr Leu Val Thr
                100                 105                 110

Val Ser Ala
        115

<210> SEQ ID NO 20
<211> LENGTH: 109
<212> TYPE: PRT
<213> ORGANISM: Artificial Sequence
<220> FEATURE:
<223> OTHER INFORMATION: humanized 4G10 variable light chain region
      consensus sequence
<220> FEATURE:
<221> NAME/KEY: X
<222> LOCATION: (35)..(35)
<223> OTHER INFORMATION: Pro or Ala
<220> FEATURE:
<221> NAME/KEY: X
<222> LOCATION: (40)..(40)
<223> OTHER INFORMATION: Gln or Glu
<220> FEATURE:
<221> NAME/KEY: X
<222> LOCATION: (46)..(46)
<223> OTHER INFORMATION: Pro or Phe
<220> FEATURE:
<221> NAME/KEY: X
<222> LOCATION: (56)..(56)
<223> OTHER INFORMATION: Lys or Arg or any other amino acid except Met
      or Cys
<220> FEATURE:
<221> NAME/KEY: X
<222> LOCATION: (58)..(58)
<223> OTHER INFORMATION: Ser or Pro
<220> FEATURE:
<221> NAME/KEY: X
<222> LOCATION: (60)..(60)
<223> OTHER INFORMATION: Thr or Val
<220> FEATURE:
<221> NAME/KEY: X
<222> LOCATION: (89)..(89)
<223> OTHER INFORMATION: Tyr or Phe
<220> FEATURE:
<221> NAME/KEY: X
<222> LOCATION: (93)..(93)
<223> OTHER INFORMATION: Trp or any amino acid except Met or Cys
<220> FEATURE:
<221> NAME/KEY: X
<222> LOCATION: (98)..(98)
```

-continued

<223> OTHER INFORMATION: Trp or any amino acid except Met or Cys

<400> SEQUENCE: 20

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Phe Xaa Asn Trp Val Gln Xaa Lys Pro Gly Gln Ala Xaa Arg Ser
        35                  40                  45

Leu Ile Gly Gly Thr Asn Asn Xaa Ala Xaa Trp Xaa Pro Ala Arg Phe
50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Xaa Cys Ala Leu Xaa Tyr Ser Asn
                85                  90                  95

His Xaa Val Phe Gly Gly Gly Thr Lys Leu Thr Val Leu
            100                 105
```

<210> SEQ ID NO 21
<211> LENGTH: 5
<212> TYPE: PRT
<213> ORGANISM: Artificial Sequence
<220> FEATURE:
<223> OTHER INFORMATION: 4G10 HCDR1 consensus
<220> FEATURE:
<221> NAME/KEY: X
<222> LOCATION: (4)..(4)
<223> OTHER INFORMATION: Met or Val or Leu or Ile or Gly or Ala or Ser or Thr

<400> SEQUENCE: 21

```
Gly Tyr Thr Xaa Asn
1               5
```

<210> SEQ ID NO 22
<211> LENGTH: 17
<212> TYPE: PRT
<213> ORGANISM: Artificial Sequence
<220> FEATURE:
<223> OTHER INFORMATION: 4G10 HCDR2 consensus sequence
<220> FEATURE:
<221> NAME/KEY: X
<222> LOCATION: (7)..(7)
<223> OTHER INFORMATION: Asn or Asp
<220> FEATURE:
<221> NAME/KEY: X
<222> LOCATION: (9)..(9)
<223> OTHER INFORMATION: Thr or Asp or Glu or Gly or Ala
<220> FEATURE:
<221> NAME/KEY: X
<222> LOCATION: (12)..(12)
<223> OTHER INFORMATION: Ala or Asn
<220> FEATURE:
<221> NAME/KEY: X
<222> LOCATION: (16)..(16)
<223> OTHER INFORMATION: Gln or Met

<400> SEQUENCE: 22

```
Leu Ile Asn Pro Tyr Asn Xaa Ile Xaa Asn Tyr Xaa Gln Lys Phe Xaa
1               5                   10                  15

Gly
```

<210> SEQ ID NO 23
<211> LENGTH: 6
<212> TYPE: PRT
<213> ORGANISM: Artificial Sequence

```
<220> FEATURE:
<223> OTHER INFORMATION: 4G10 HCDR3 sequence

<400> SEQUENCE: 23

Leu Asp Tyr Arg Ser Tyr
1               5

<210> SEQ ID NO 24
<211> LENGTH: 14
<212> TYPE: PRT
<213> ORGANISM: Artificial Sequence
<220> FEATURE:
<223> OTHER INFORMATION: 4G10 LCDR1 consensus sequence
<220> FEATURE:
<221> NAME/KEY: X
<222> LOCATION: (13)..(13)
<223> OTHER INFORMATION: Pro or Ala

<400> SEQUENCE: 24

Gly Ser Ser Thr Gly Ala Val Thr Thr Ser Asn Phe Xaa Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: 4G10 LCDR2 consensus sequence
<220> FEATURE:
<221> NAME/KEY: X
<222> LOCATION: (5)..(5)
<223> OTHER INFORMATION: Lys or Arg or any amino acid except Met or Cys
<220> FEATURE:
<221> NAME/KEY: X
<222> LOCATION: (7)..(7)
<223> OTHER INFORMATION: Ser or Pro

<400> SEQUENCE: 25

Gly Thr Asn Asn Xaa Ala Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: 4G10 LCDR3 consensus sequence
<220> FEATURE:
<221> NAME/KEY: X
<222> LOCATION: (3)..(3)
<223> OTHER INFORMATION: Trp or any amino acid except Met or Cys
<220> FEATURE:
<221> NAME/KEY: X
<222> LOCATION: (8)..(8)
<223> OTHER INFORMATION: Trp or any amino acid except Met or Cys

<400> SEQUENCE: 26

Ala Leu Xaa Tyr Ser Asn His Xaa
1               5

<210> SEQ ID NO 27
<211> LENGTH: 8
<212> TYPE: PRT
<213> ORGANISM: Artificial Sequence
<220> FEATURE:
<223> OTHER INFORMATION: 4G10 HCDR1 sequence

<400> SEQUENCE: 27

Gly Tyr Ser Phe Thr Gly Tyr Thr
1               5
```

```
<210> SEQ ID NO 28
<211> LENGTH: 8
<212> TYPE: PRT
<213> ORGANISM: Artificial Sequence
<220> FEATURE:
<223> OTHER INFORMATION: 4G10 HCDR2
<220> FEATURE:
<221> NAME/KEY: X
<222> LOCATION: (6)..(6)
<223> OTHER INFORMATION: Asn or Asp or Glu
<220> FEATURE:
<221> NAME/KEY: X
<222> LOCATION: (8)..(8)
<223> OTHER INFORMATION: Thr or Asp or Glu or Gly or Ala

<400> SEQUENCE: 28

Ile Asn Pro Tyr Asn Xaa Ile Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: 4G10 HCDR3

<400> SEQUENCE: 29

Ala Arg Leu Asp Tyr Arg Ser Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: 4G10 LCDR1

<400> SEQUENCE: 30

Thr Gly Ala Val Thr Thr Ser Asn Phe
1               5

<210> SEQ ID NO 31
<211> LENGTH: 3
<212> TYPE: PRT
<213> ORGANISM: Artificial Sequence
<220> FEATURE:
<223> OTHER INFORMATION: 4G10 LCDR2

<400> SEQUENCE: 31

Gly Thr Asn
1

<210> SEQ ID NO 32
<211> LENGTH: 9
<212> TYPE: PRT
<213> ORGANISM: Artificial Sequence
<220> FEATURE:
<223> OTHER INFORMATION: 4G10 LCDR3
<220> FEATURE:
<221> NAME/KEY: X
<222> LOCATION: (3)..(3)
<223> OTHER INFORMATION: Trp or any amino acid except Met or Cys
<220> FEATURE:
<221> NAME/KEY: X
<222> LOCATION: (8)..(8)
<223> OTHER INFORMATION: Trp or any amino acid except Met or Cys

<400> SEQUENCE: 32
```

Ala Leu Xaa Tyr Ser Asn His Xaa Val
1               5

<210> SEQ ID NO 33
<211> LENGTH: 330
<212> TYPE: PRT
<213> ORGANISM: Artificial Sequence
<220> FEATURE:
<223> OTHER INFORMATION: Exemplary heavy chain IgG1 constant domain

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 107

```
<212> TYPE: PRT
<213> ORGANISM: Artificial Sequence
<220> FEATURE:
<223> OTHER INFORMATION: Exemplary human kappa chain constant domain

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 443
<212> TYPE: PRT
<213> ORGANISM: Artificial Sequence
<220> FEATURE:
<223> OTHER INFORMATION: 10D1 heavy chain

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Pro Ser Val Phe
225                 230                 235                 240

Leu Phe Pro Pro Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Leu Thr Cys Leu Val Lys Gly
        355                 360                 365

Phe Tyr Pro Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 36
<211> LENGTH: 214
<212> TYPE: PRT
<213> ORGANISM: Artificial Sequence
<220> FEATURE:
<223> OTHER INFORMATION: 10D1 Light chain

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```